(12) United States Patent
Stayton et al.

(10) Patent No.: US 9,006,193 B2
(45) Date of Patent: Apr. 14, 2015

(54) POLYMERIC CARRIER

(75) Inventors: Patrick S. Stayton, Seattle, WA (US); Allan S. Hoffman, Seattle, WA (US); Anthony J. Convertine, Seattle, WA (US); Craig L. Duvall, Nashville, TN (US); Danielle Benoit, Rochester, NY (US); Robert W. Overell, Shoreline, WA (US); Paul H. Johnson, Snohomish, WA (US); Anna S. Gall, Woodinville, WA (US); Mary G. Prieve, Lake Forest Park, WA (US); Amber E. E. Paschal, Redmond, WA (US); Charbel Diab, Seattle, WA (US); Priyadarsi De, Mohanpur (IN)

(73) Assignees: University of Washington, Seattle, WA (US); PhaseRx, Inc., Seattle, WA (US)

( * ) Notice: Subject to any disclaimer, the term of this patent is extended or adjusted under 35 U.S.C. 154(b) by 0 days.

(21) Appl. No.: 12/992,536

(22) PCT Filed: May 13, 2009

(86) PCT No.: PCT/US2009/043837
§ 371 (c)(1),
(2), (4) Date: Feb. 25, 2011

(87) PCT Pub. No.: WO2009/140421
PCT Pub. Date: Nov. 19, 2009

(65) Prior Publication Data
US 2011/0143435 A1    Jun. 16, 2011

Related U.S. Application Data

(60) Provisional application No. 61/052,914, filed on May 13, 2008, provisional application No. 61/052,908, filed on May 13, 2008, provisional application No. 61/091,294, filed on Aug. 22, 2008, provisional application No. 61/112,054, filed on Nov. 6, 2008, provisional application No. 61/140,779, filed on Dec. 24, 2008, provisional application No. 61/171,358, filed on Apr. 21, 2009.

(51) Int. Cl.
| | | |
|---|---|---|
| A61K 47/48 | (2006.01) |
| A01N 43/04 | (2006.01) |
| A61K 48/00 | (2006.01) |
| A61K 47/30 | (2006.01) |
| C12Q 1/68 | (2006.01) |
| C12N 15/00 | (2006.01) |
| C08F 120/18 | (2006.01) |
| C12N 15/87 | (2006.01) |
| A61K 9/107 | (2006.01) |
| C08F 293/00 | (2006.01) |

(52) U.S. Cl.
CPC .............. *C12N 15/87* (2013.01); *A61K 9/1075* (2013.01); *A61K 47/48092* (2013.01); *A61K 47/48176* (2013.01); *A61K 47/48215* (2013.01); *C08F 293/005* (2013.01)

(58) Field of Classification Search
None
See application file for complete search history.

(56) References Cited

U.S. PATENT DOCUMENTS

| | | |
|---|---|---|
| 4,699,784 A | 10/1987 | Shih |
| 5,057,313 A | 10/1991 | Shih |
| 6,306,994 B1 | 10/2001 | Donald |
| 6,359,054 B1 | 3/2002 | Lemieux |
| 6,383,811 B2 | 5/2002 | Wolff |
| 6,410,057 B1 | 6/2002 | Kweon-Choi |
| 6,780,428 B2 | 8/2004 | Ranger |
| 6,835,393 B2 | 12/2004 | Hoffman |
| 6,919,091 B2 | 7/2005 | Trubetskoy |
| 6,939,564 B2 | 9/2005 | Ranger |
| 7,033,607 B2 | 4/2006 | Trubetskoy |
| 7,094,810 B2 | 8/2006 | Sant |
| 7,098,032 B2 | 8/2006 | Trubetskoy |
| 7,217,776 B1 | 5/2007 | Mallapragada |
| 7,374,778 B2 | 5/2008 | Hoffman |
| 7,510,731 B2 | 3/2009 | Ranger |
| 7,524,680 B2 | 4/2009 | Wolff |
| 7,718,193 B2 | 5/2010 | Stayton |
| 7,737,108 B1 | 6/2010 | Hoffman |
| 8,367,113 B2 | 2/2013 | Gu |
| 2001/0007666 A1 | 7/2001 | Hoffman |
| 2003/0134420 A1 | 7/2003 | Lollo |
| 2003/0191081 A1 | 10/2003 | Lemieux |
| 2003/0211167 A1 | 11/2003 | Gustavsson |
| 2004/0054127 A1 | 3/2004 | Jin |
| 2004/0072784 A1 | 4/2004 | Sant |

(Continued)

FOREIGN PATENT DOCUMENTS

| | | |
|---|---|---|
| EP | 0 321 233 A1 | 6/1989 |
| EP | 1 621 569 A1 | 2/2006 |

(Continued)

OTHER PUBLICATIONS

Jeong et al., Novel Polymer-DNA Hybrid Polymeric Micelles Composed of Hydrophobic Poly(D,L-lactic-co-glycolic Acid) and Hydrophilic Oligonucleotides; Bioconjugate Chem, vol. 12, pp. 917-923, 2001.*

(Continued)

*Primary Examiner* — Jennifer Dunston
*Assistant Examiner* — Addison D Ault
(74) *Attorney, Agent, or Firm* — Christensen O'Connor Johnson Kindness PLLC

(57) ABSTRACT

Provided herein are polymeric carriers suitable for the delivery of polynucleotides (e.g. oligonucleotides) and/or other therapeutic agents into a living cell.

13 Claims, 18 Drawing Sheets

(56) References Cited

U.S. PATENT DOCUMENTS

| | | | |
|---|---|---|---|
| 2004/0151775 | A1 | 8/2004 | Rozema |
| 2004/0162235 | A1 | 8/2004 | Trubetskoy |
| 2005/0136102 | A1* | 6/2005 | Hoffman et al. ............ 424/449 |
| 2005/0220880 | A1 | 10/2005 | Lewis |
| 2005/0260276 | A1 | 11/2005 | Yang |
| 2006/0134221 | A1 | 6/2006 | Geall |
| 2006/0165810 | A1 | 7/2006 | Discher |
| 2006/0171980 | A1 | 8/2006 | Helmus |
| 2006/0235161 | A1 | 10/2006 | Heller |
| 2007/0003609 | A1 | 1/2007 | Collin-Djangone |
| 2007/0010632 | A1 | 1/2007 | Kaplan |
| 2007/0037891 | A1 | 2/2007 | Esfand |
| 2007/0059271 | A1 | 3/2007 | Kataoka |
| 2007/0110709 | A1 | 5/2007 | Ranger |
| 2007/0134188 | A1 | 6/2007 | Collin-Djangone |
| 2007/0207966 | A1* | 9/2007 | Kim et al. ............ 514/15 |
| 2007/0224241 | A1 | 9/2007 | Stayton |
| 2008/0069902 | A1 | 3/2008 | Zhao |
| 2008/0081075 | A1 | 4/2008 | Hsiue |
| 2008/0171067 | A1 | 7/2008 | Govindan |
| 2008/0243049 | A1 | 10/2008 | Hardy |
| 2009/0036625 | A1 | 2/2009 | Chang |
| 2010/0150952 | A1 | 6/2010 | Stayton |
| 2011/0123636 | A1 | 5/2011 | Stayton |
| 2011/0143434 | A1 | 6/2011 | Stayton |
| 2011/0281354 | A1 | 11/2011 | Stayton |
| 2011/0281934 | A1 | 11/2011 | Johnson |
| 2011/0286957 | A1 | 11/2011 | Prieve |
| 2012/0021514 | A1 | 1/2012 | Johnson |
| 2014/0228516 | A1 | 8/2014 | Stayton |

FOREIGN PATENT DOCUMENTS

| | | |
|---|---|---|
| EP | 2 180 004 A1 | 4/2010 |
| FR | 2 767 829 A1 | 3/1999 |
| WO | 99/29303 A1 | 6/1999 |
| WO | 01/87227 A2 | 11/2001 |
| WO | 03/087188 A1 | 10/2003 |
| WO | 2005/108614 A2 | 11/2005 |
| WO | 2006016166 A1 | 2/2006 |
| WO | 2007/008300 A2 | 1/2007 |
| WO | 2007/109584 A1 | 9/2007 |
| WO | 2008/004978 A1 | 1/2008 |
| WO | 2008/022309 A2 | 2/2008 |
| WO | 2008/071009 A1 | 6/2008 |
| WO | 2008/085556 A2 | 7/2008 |
| WO | 2008/148174 A1 | 12/2008 |
| WO | 2008/153940 A1 | 12/2008 |
| WO | 2009/009025 A1 | 1/2009 |
| WO | 2009/021728 A2 | 2/2009 |
| WO | 2009/140421 A2 | 11/2009 |
| WO | 2009/140423 A2 | 11/2009 |
| WO | 2009/140427 A2 | 11/2009 |
| WO | 2009/140429 A2 | 11/2009 |
| WO | 2009/140432 A2 | 11/2009 |
| WO | 2010/021770 A1 | 2/2010 |
| WO | 2010/053596 A1 | 5/2010 |
| WO | 2010/053597 A2 | 5/2010 |
| WO | 2010/054266 A2 | 5/2010 |
| WO | 2010/077678 A2 | 7/2010 |

OTHER PUBLICATIONS

Convertine et al., pH-Responsive Polymeric Micelle Carriers for siRNA Drugs; Biomacromolecules, vol. 11, pp. 2904-2911, 2010.*

Cheng et al., Multifunctional Triblock Copolymers for Intracellular Messenger RNA Delivery; Biomaterials, vol. 22, pp. 6868-6876, 2012.*

Bulmus et al., A new pH-responsive and glutathione-reactive, endosomal membrane-disruptive polymeric carrier for intracellular delivery of biomolecular drugs; J Controlled Release, vol. 93, pp. 105-120, 2003.*

Benoit, D.S.W., et al., "Resensitizing Multidrug Resistant Cells to Doxorubicin Through plk1 Knockdown Using a Novel pH-Responsive Micelle siRNA Delivery System," Abstracts of Society for Biomaterials Meeting, Apr. 22, 2009, 1 page.

Bulmus, V., et al., "A New pH-Responsive and Glutathione-Reactive, Endosomal Membrane-Disruptive Polymeric Carrier for Intracellular Delivery of Biomolecular Drugs," Journal of Controlled Release 93(2):105-120, Dec. 2003.

Convertine, A.J., et al., "Development of a Novel Endosomolytic Diblock Copolymer for siRNA Delivery," Journal of Controlled Release 133(3):221-229, Feb. 2009.

Dufresne, M.-H., et al., "Characterization of Polyion Complex Micelles Designed to Address the Challenges of Oligonucleotide Delivery," Pharmaceutical Research 25(9):2083-2093, Sep. 2008.

Duvall, C.L., et al., "Polymer Enhanced Intracellular Delivery of a Pro-Apoptotic Peptide for Cancer Therapy," Abstracts of Society for Biomaterials Meeting, Apr. 22, 2009, 1 page.

El-Sayed, M.E.H., et al., "Smart Polymeric Carriers for Enhanced Intracellular Delivery of Therapeutic Macromolecules," Expert Opinion on Biological Therapy 5(1):23-32, Jan. 2005.

El-Sayed, M.E.H., et al., "Rational Design of Composition and Activity Correlations for pH-Sensitive and Glutathione-Reactive Polymer Therapeutics," Journal of Controlled Release 101(1-3):47-58, Jan. 2005.

Funhoff, A.M., et al., "Endosomal Escape of Polymeric Gene Delivery Complexes Is Not Always Enhanced by Polymers Buffering at Low pH," Biomacromolecules 5(1):32-39, Jan.-Feb. 2004.

Gaucher, G., et al., "Block Copolymer Micelles: Preparation, Characterization and Application in Drug Delivery," Journal of Controlled Release 109(1-3):169-188, Dec. 2005.

Henry, S.M., et al., "pH-Responsive Poly(styrene-alt-maleic anhydride) Alkylamide Copolymers for Intracellular Drug Delivery," Biomacromolecules 7(8):2407-2414, Aug. 2006.

Heredia, K.L., et al., "Reversible siRNA-Polymer Conjugates by RAFT Polymerization," Chemical Communications 28(28):3245-3247, Jul. 2008.

Inoue, T., et al., "An AB Block Copolymer of Oligo(methyl methacrylate) and Poly(acrylic acid) for Micellar Delivery of Hydrophobic Drugs," Journal of Controlled Release 51(2-3):221-229, Feb. 1998.

Jensen, K.D., et al., "Antisense Oligonucleotides Delivered to the Lysosome Escape and Actively Inhibit the Hepatitis B Virus," Bioconjucate Chemistry 13(5):975-984, Sep.-Oct. 2002.

Kataoka, K., et al., "Smart Polymeric Micelles as Nanocarriers for Oligonucleotides and siRNA Delivery," Nucleic Acids Symposium Series 49(1):17-18, Sep. 2005.

Kulkarni, S., et al, "Controlling the Aggregation of Conjugates of Streptavidin With Smart Block Copolymers Prepared Via the RAFT Copolymerization Technique," Biomacromolecules 7(10):2736-2741, Oct. 2006.

Murthy, N., et al., "Bioinspired pH-Responsive Polymers for the Intracellular Delivery of Biomolecular Drugs," Bioconjugate Chemistry 14(2):412-419, Mar.-Apr. 2003.

Murthy, N., et al., "The Design and Synthesis of Polymers for Eukaryotic Membrane Disruption," Journal of Controlled Release 61(1-2):137-143, Aug. 1999.

Peppas, N.A., "Is There a Future in Glucose-Sensitive, Responsive Insulin Delivery Systems?" Drug Delivery Science and Technology 14(4):247-256, Sep. 2004.

Read, M.L., et al., "Physicochemical and Biological Characterisation of an Antisense Oligonucleotide Targeted Against the bcl-2 mRNA Complexed With Cationic-Hydrophilic Copolymers," European Journal of Pharmaceutical Sciences 10(3):169-177, May 2000.

Segura, T., and J.A. Hubbell, "Synthesis and In Vitro Characterization of an ABC Triblock Copolymer for siRNA Delivery," Bioconjugate Chemistry 18(3):736-745, May 2007.

Stayton, P.S., and A.S. Hoffman, "'Smart' pH-Responsive Carriers for Intracellular Delivery of Biomolecular Drugs," in V. Torchilin (ed.), "Fundamental Biomedical Technologies: Multifunctional Pharmaceutical Nanocarriers," Springer Science+Business Media, LLC, New York, May 2008, vol. 4, pp. 143-159.

(56) References Cited

OTHER PUBLICATIONS

Stayton, P.S., et al., "Intelligent Biohybrid Materials for Therapeutic and Imaging Agent Delivery," Proceedings of the IEEE 93(4):726-736, Apr. 2005.
Torchilin, V.P., "Micellar Nanocarriers: Pharmaceutical Perspectives," Pharmaceutical Research 24(1):1-16, Jan. 2007.
Wang, L., et al., "Delivery of Antisense Oligonucleotides Using HPMA Polymer: Synthesis of a Thiol Polymer and Its Conjugation to Water-Soluble Molecules," Bioconjugate Chemistry 9(6):749-757, Nov.-Dec. 1998.
Yamamoto, S.-I., et al., "Temperature- and pH-Responsive Dense Copolymer Brushes Prepared by ATRP," Macromolecules 41(19):7013-7020, Oct. 2008.
Yessine, M.-A., et al., "Proton-Actuated Membrane-Destabilizing Polyion Complex Micelles," Bioconjugate Chemistry 18(3):1010-1014, May-Jun. 2007.
International Search Report and Written Opinion, mailed Jan. 4, 2010, issued in corresponding International Application No. PCT/US2009/043837, filed May 13, 2009, 14 pages.
Search Report and Written Opinion mailed Jan. 31, 2012, issued in corresponding Singapore Application No. 201008329-3, filed May 13, 2009, 18 pages.
Jeong, J.H., et al., "siRNA Conjugate Delivery Systems," Bioconjugate Chemistry 20(1):5-14, Jan. 2009.
Meyer, M., et al., "Synthesis and Biological Evaluation of a Bioresponsive and Endosomolytic siRNA—Polymer Conjugate," Molecular Pharmaceutics 6(3):752-762, May-Jun. 2009.
Oishi, M., et al., "Lactosylated Poly(ethylene glycol)-siRNA Conjugate Through Acid-Labile β-Thiopropionate Linkage to Construct pH-Sensitive Polyion Complex Micelles Achieving Enhanced Gene Silencing in Hepatoma Cells," Journal of the American Chemical Society 127(6):1624-1625, Feb. 2005.
Fishbein, I., et al., "Local Delivery of Gene Vectors From Bare-Metal Stents by Use of a Biodegradable Synthetic Complex Inihibits In-Stent Restenosis in Rat Carotid Arteries," Circulation 117(16):2096-2103, Apr. 2008.
Invitiation to Pay Additional Fees and Partial International Search Report mailed Apr. 26, 2011, issued in corresponding International Application No. PCT/US2010/056993, filed Nov. 17, 2010, 6 pages.
Varghese, O.P., et al., "In Situ Cross-Linkable High Molecular Weight Hyaluronan—Bisphosphonate Conjugate for Localized Delivery and Cell-Specific Targeting: A Hydrogel Linked Prodrug Approach," Journal of the American Chemical Society 131(25):8781-8783, Jul. 2009.
Cho, Y.W., et al., "Polycation Gene Delivery Systems: Escape From Endosomes to Cytosol," Journal of Pharmacy and Pharmacology 55(6):721-734, Jun. 2003.
International Search Report and Written Opinion mailed Mar. 7, 2011, issued in corresponding International Application No. PCT/US2010/056565, filed Nov. 12, 2010, 12 pages.
Extended European Search Report mailed Sep. 27, 2011, issued in corresponding European Application No. 09 74 7504, filed May 13, 2009, 5 pages.
Patent Examination Report No. 1, issued Sep. 6, 2012, in corresponding Australian Application No. 2009246321, filed May 13, 2009, 4 pages.
Extended European Search Report mailed Feb. 5, 2014, issued in corresponding European Application No. 09 825 146.5, filed May 13, 2009, 9 pages.
Cheung, C.Y., et al., "A pH-Sensitive Polymer That Enhances Cationic Lipid-Mediated Gene Transfer," Bioconjugate Chemistry 12(6):906-910, Oct. 2001.
Hood, J.D., et al., "Tumor Regression by Targeted Gene Delivery to the Neovasculature," Science, New Series 296 (5577):2404-2407, Jun. 2002.

Jeong, Y.-I., et al., "Cellular Recognition of Paclitaxel-Loaded Polymeric Nanoparticles Composed of Poly(y-benzyl L-glutamate) and Poly(ethylene glycol) Diblock Copolymer Endcapped With Galactose Moiety," International Journal of Pharmaceutics 296(2005):151-161, Apr. 2005.
Joralemon, M.J., et al., "Synthesis, Characterization, and Bioavailability of Mannosylated Shell Cross-Linked Nanoparticles," Biomacromolecules 5(3):903-913, May-Jun. 2004.
Kabanov, A.V., et al., "Pluronic Micelles as a Tool for Low-Molecular Compound Vector Delivery Into a Cell: Effect of *Staphylococcus-aureus* Enterotoxin B on Cell Loading With Micelle Incorporated Fluorescent Dye," Biochemistry International 26(6):1035-1042, May 1992.
Kyriakides, T.R., et al., "pH-Sensitive Polymers That Enhance Intracellular Drug Delivery In Vivo," Journal of Controlled Release 78(1-3):295-303, Jan. 2002.
Le Garrec, D., et al., "Micelles in Anticancer Drug Delivery," American Journal of Drug Delivery 2(1):15-42, Mar. 2004.
Lee, E.S., et al., "Super pH-Sensitive Multifunctional Polymeric Micelle," Nano Letters 5(2):325-329, Feb. 2005.
Nagasaki, Y. et al., "Sugar-Installed Block Copolymer Micelles: Their Preparation and Specific Interaction With Lectin Molecules," Biomacromolecules 2(4):1067-1070, Winter 2001.
Raso, V., "Intracellular Targeting Using Bispecific Antibodies," Methods in Molecular Medicine 25:37-49, Jan. 2000.
Sawant, R.M., et al., "'SMART' Drug Delivery Systems: Double-Targeted pH-Responsive Pharmaceutical Nanocarriers," Bioconjugate Chemistry 17:943-949, Jun. 2006.
Turk, M.J., et al., "Characterization of a Novel pH-Sensitive Peptide That Enhances Drug Release From Folate-Targeted Liposomes at Endosomal pHs," Biochimica et Biophysica Acta 1559(1):56-68, Feb. 2002.
Wakebayashi, D., et al., "Lactose-Conjugated Polyion Complex Micelles Incorporating Plasmid DNA as a Targetable Gene Vector System: Their Preparation and Gene Transfecting Efficiency Against Cultured HepG2 Cells," Journal of Controlled Release 95(3):653-664, Mar. 2004.
Yasugi, K., et al., "Sugar-Installed Polymer Micelles: Synthesis and Micellization of Poly(ethylene glycol)-Poly(D,L-lactide) Block Copolymers Having Sugar Groups at the PEG Chain End," Macromolecules 32:8024-8032, Nov. 1999.
Yoo, H.S., and T.G. Park, "Folate Receptor Targeted Biodegradable Polymeric Doxorubicin Micelles," Journal of Controlled Release 96(2):273-283, Apr. 2004.
Cheng, Z., et al., "Brush-Type Amphiphilic Diblock Copolymers From 'Living'/Controlled Radical Polymerizations and Their Aggregation Behavior," Langmuir 21(16):7180-7185, Jul. 2005.
Finne-Wistrand, A., and A.-C. Albertson, "The Use of Polymer Design in Resorbable Colloids," Annual Review of Materials Research 36:369-395, Aug. 2006.
Oishi, M., et al., "pH-Responsive Oligodeoxynucleotide (ODN)-Poly(Ethylene Glycol) Conjugate Through Acid-Labile β-Thiopropionate Linkage: Preparation and Polyion Complex Micelle Formation," Biomacromolecules 4(5):1426-1432, Aug. 2003.
Wei, J.-S., et al., "Temperature- and pH-Sensitive Core-Shell Nanoparticles Self-Assembled From Poly(N-isopropylacrylamide-co-acrylic acid-co-cholesteryl acrylate) for Intracellular Delivery of Anticancer Drugs," Frontiers in Bioscience 10:3058-3067, Sep. 2005.
York, A.W. et al., "Advances in the Synthesis of Amphiphilic Block Copolymers via RAFT Polymerization: Stimuli-Responsive Drug and Gene Delivery," Advanced Drug Delivery Reviews 60(9):1018-1036, Jun. 2008.

\* cited by examiner

FIG. 1A

| Polymer | Structure $[D]_{MW_1}\text{-}[B_x\text{-}P_y\text{-}D_z]_{MW_2}$ | Mn Kda | Block Ratio $MW_2/MW_1$ |
|---|---|---|---|
| P7v1 | $[D]_{9.1K}\text{-}[B_{48}\text{-}P_{29}\text{-}D_{23}]_{11.37K}$ | 19 | 1.2 |
| P7v2 | $[D]_{10K}\text{-}[B_{46}\text{-}P_{18}\text{-}D_{37}]_{8.9K}$ | 19 | 0.9 |
| P7v3 | $[D]_{6.5K}\text{-}[B_{41}\text{-}P_{39}\text{-}D_{20}]_{9.5K}$ | 16 | 1.5 |
| P7v6 | $[D]_{9.1K}\text{-}[B_{52}\text{-}P_{26}\text{-}D_{22}]_{21.9K}$ | 31 | 2.4 | x, y, z ARE MOLE %. MOLECULAR WEIGHTS WERE DETERMINED BY GEL PERMEATION CHROMATOGRAPHY USING PMMA STANDARDS. COMPOSITIONS WERE DETERMINED BY NMR SPECTROSCOPY

FIG. 1B

| Polymer | Mn (kDa) | PDI | % PEGMA | % DMAEMA | Mn (kDa) | PDI | % BMA | % DMAEMA | %PAA |
|---|---|---|---|---|---|---|---|---|---|
| | | | FIRST BLOCK | | | | SECOND BLOCK | | |
| P7-PEGMA100 | 22.24 | 1.34 | 100 | 0 | 45.5 | 1.48 | 50 | 28 | 22 |
| P7-PEGMA20 | 11.44 | 1.33 | 17 | 83 | 41.0 | 1.52 | 56 | 23 | 21 |
| P7-PEGMA10 | 11.01 | 1.31 | 10 | 90 | 42.0 | 1.42 | 51 | 23 | 26 |
| P7-PEGMA5 | 10.60 | 1.17 | 5 | 95 | 27.1 | 1.27 | - | - | - |
| P7-PEGMA-50- | 14.50 | 1.35 | 46 | 54 | 38.1 | 1.44 | 55 | 25 | 20 |
| P7-PEGMA-50- | 24.25 | 1.23 | 47 | 53 | 38.4 | 1.45 | 52 | 23 | 25 |

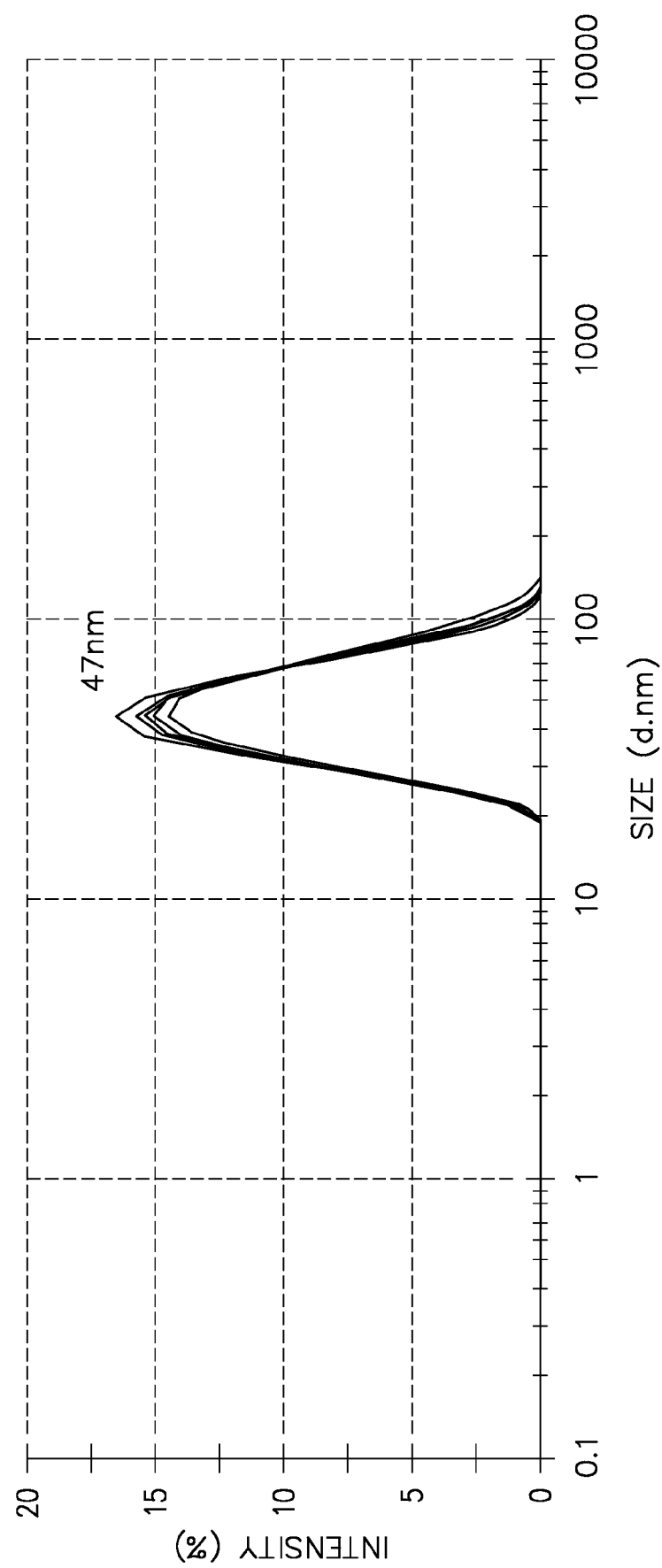

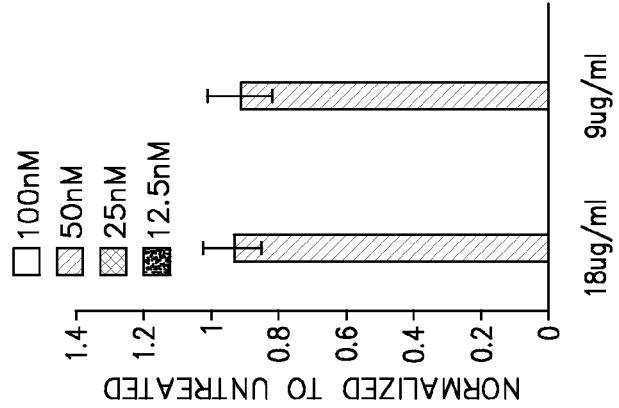
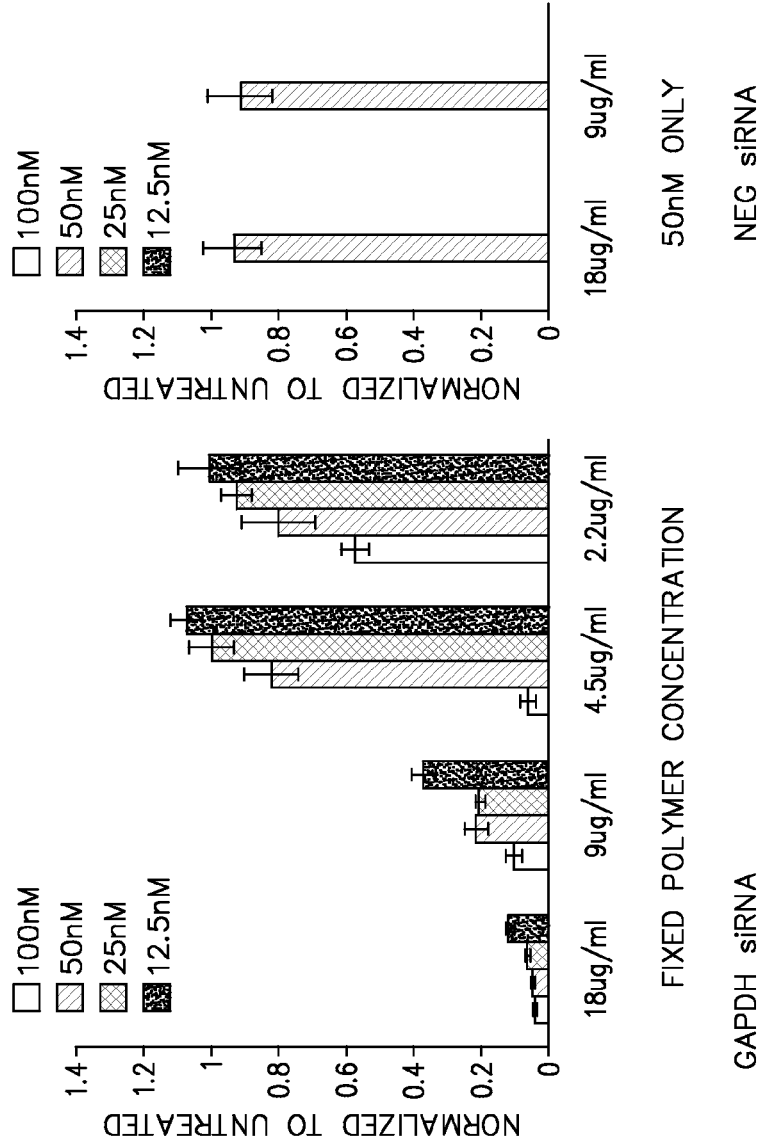
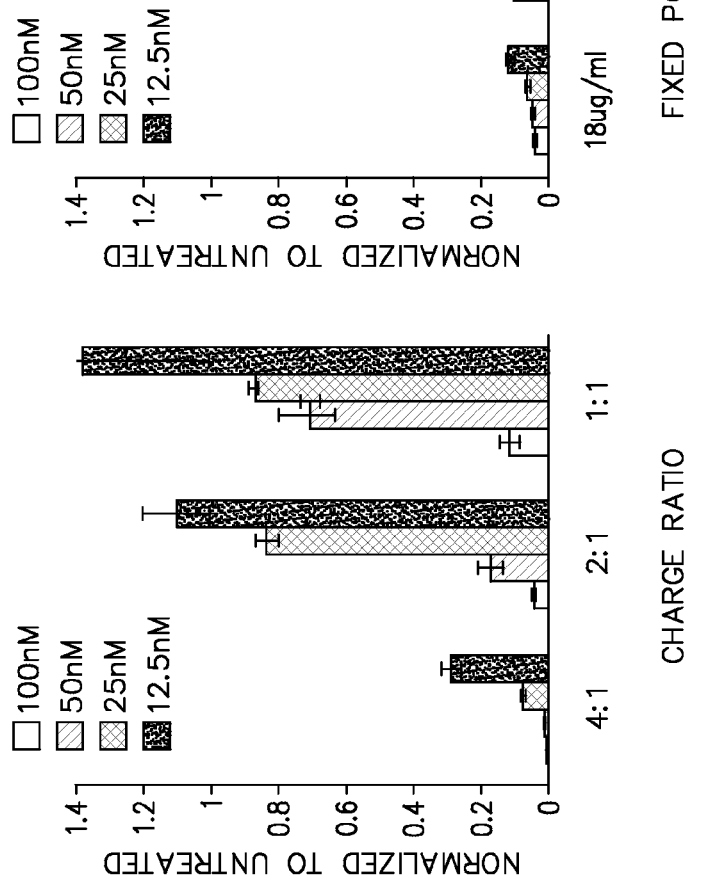

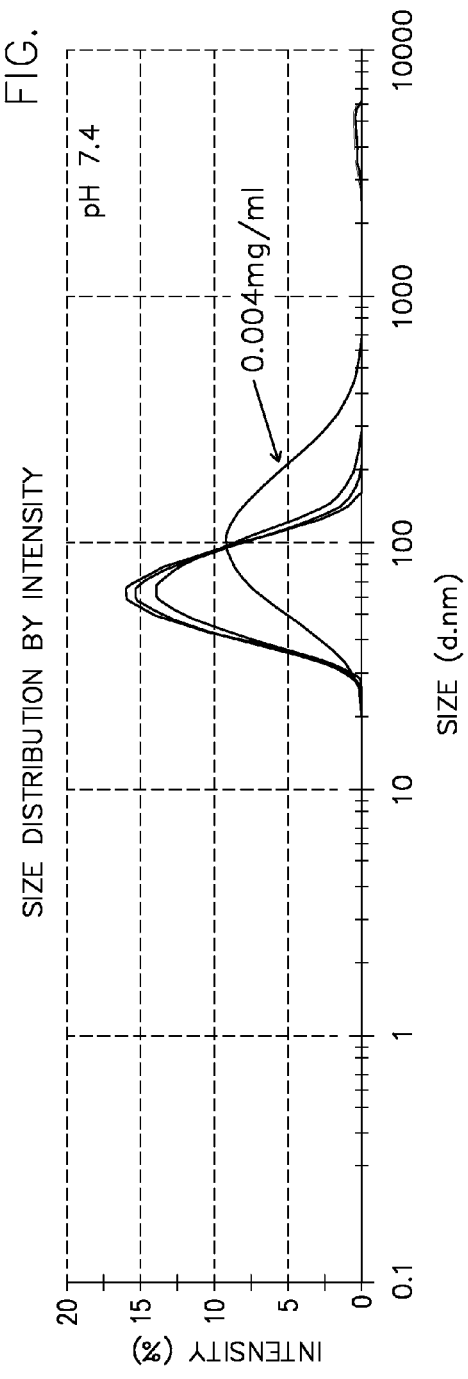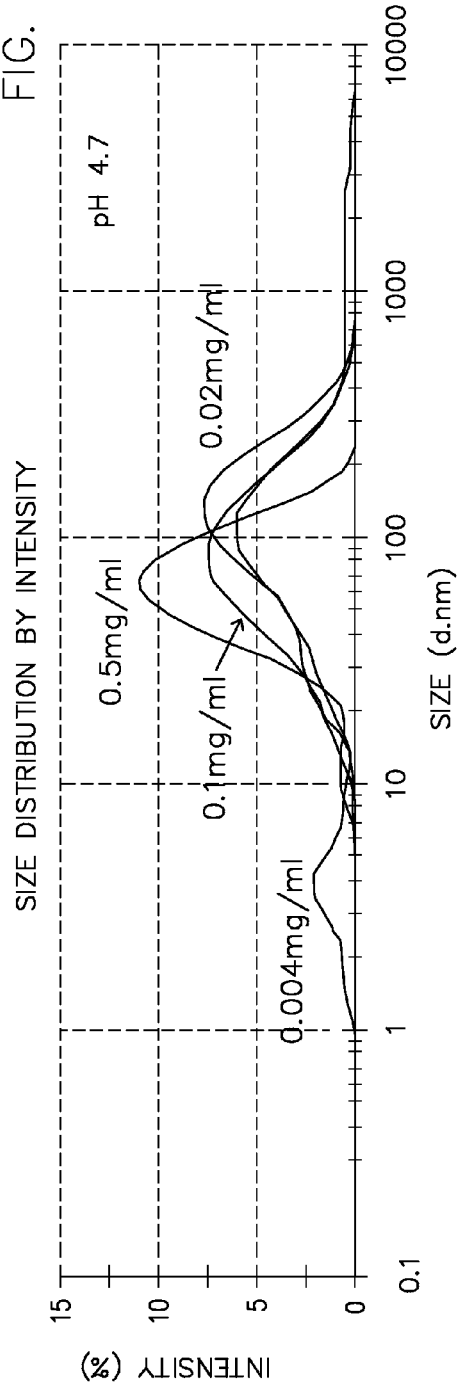

FIG. 12A

Polymer concentrations and charge ratios

|  | 100 nM | 50 nM | 25 nM | 12.5 nM |
|---|---|---|---|---|
| 4:1 | 36 ug/ml | 18 ug/ml | 9 ug/ml | 4.5 ug/ml |
| 2:1 | 18 ug/ml | 9 ug/ml | 4.5 ug/ml | 2.2 ug/ml |
| 1:1 | 9 ug/ml | 4.5 ug/ml | 2.2 ug/ml | 1.1 ug/ml |
| 18 ug/ml | 2:1 | 4:1 | 8:1 | 16:1 |
| 9 ug/ml | 1:1 | 2:1 | 4:1 | 8:1 |
| 4.5 ug/ml | 0.5:1 | 1:1 | 2:1 | 4:1 |
| 2.2 ug/ml | 0.25:1 | 0.5:1 | 1:1 | 2:1 |

FIG. 12B

% Knockdown Results

| 100 nM | 50 nM | 25 nM | 12.5 nM |
|---|---|---|---|
| 99% | 98% | 92% | 71% |
| 95% | 82% | 16% | -10% |
| 88% | 28% | 13% | -38% |
| 96% | 95% | 93% | 88% |
| 89% | 78% | 79% | 63% |
| 94% | 18% | 0% | -7% |
| 43% | 19% | 7% | 0% |

GALACTOSE END FUNCTONALIZED POLY[DMAEMA]-macro CTA

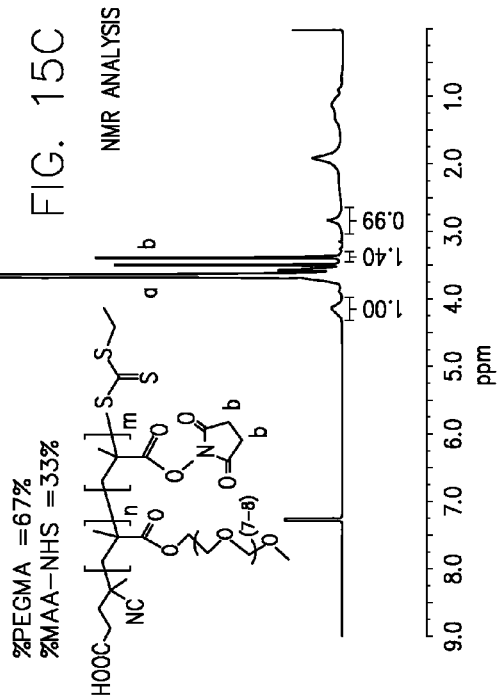

FIG. 15A

[PEGMA]:[MAA-NHS]=75:25

| NAME | FW(g/mol) | EQUIV. | mol | WEIGHT | ACTUAL WEIGHT |
|---|---|---|---|---|---|
| PEGMA | 475 | 112.5 | $5.5958 \times 10^{-3}$ | 2.658g | 2.6641g |
| MAA-NHS | 183.16 | 37.5 | $1.8672 \times 10^{-3}$ | 0.342g | 0.3422g |
| ECT | 263.4 | 1 | $4.9740 \times 10^{-5}$ | 13.1mg | 13.8mg |
| AIBN | 164.21 | 0.04 | $1.9896 \times 10^{-6}$ | 0.33mg | 0.34mg |

DMF=3.0g; $N_2$ PURGING: 30 min; CONDUCT POLYMERIZATION AT 68°C. POLYM.TIME=2h 5m COPOLYMERS WERE DIALYZED AGAINST METHANOL (1L × 8) FOR 50h, USING MWCO MEMBRANE 2K; METHANOL WAS REMOVED UNDER THE HOOD, DRIED UNDER VACUUM 3h, FINALLY LYOPHILIZED FOR 3h.

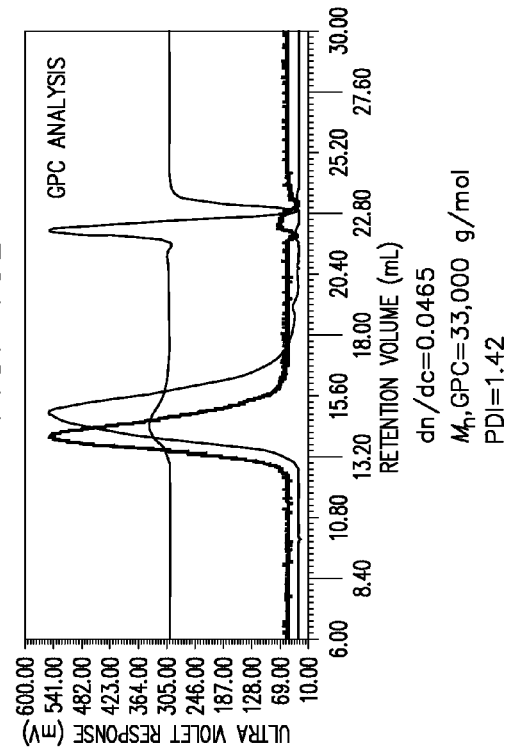

FIG. 15B — GPC ANALYSIS
$dn/dc = 0.0465$
$M_n$, GPC = 33,000 g/mol
PDI = 1.42

FIG. 15C — NMR ANALYSIS
%PEGMA = 67%
%MAA-NHS = 33%

RAFT CO-POLYMERIZATION OF PEGMA AND MAA-NHS

STRUCTURES OF CONJUGATABLE siRNAs, PEPTIDES AND PYRIDYL DISULFIDE AMINE

PEPTIDE

SEQUENCE LISTING

<160> NUMBER OF SEQ ID NOS: 7

<210> SEQ ID NO 1
<211> LENGTH: 25
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (1)..(25)
<223> OTHER INFORMATION: Sequence is DNA/RNA hybrid
<220> FEATURE:
<221> NAME/KEY: misc_feature
<222> LOCATION: (1)..(23)
<223> OTHER INFORMATION: Nucleotide at positions 1-23 is RNA
<220> FEATURE:
<221> NAME/KEY: misc_feature
<222> LOCATION: (24)..(25)
<223> OTHER INFORMATION: Nucleotide at positions 24-25 is DNA

<400> SEQUENCE: 1
ggucauccau gacaacuuug guatc                                          25

<210> SEQ ID NO 2
<211> LENGTH: 27
<212> TYPE: RNA
<213> ORGANISM: Artificial Sequence
<220> FEATURE:
<223> OTHER INFORMATION: Synthetic

<400> SEQUENCE: 2
gauaccaaag uugucaugga ugaccuu                                        27

<210> SEQ ID NO 3
<211> LENGTH: 21
<212> TYPE: RNA
<213> ORGANISM: Artificial Sequence
<220> FEATURE:
<223> OTHER INFORMATION: Synthetic

<400> SEQUENCE: 3
gaaugugggu ggcaacuuua g                                              21

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
aaaguugcca cccacauuca g                                              21

<210> SEQ ID NO 5
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(25)
<223> OTHER INFORMATION: Sequence is DNA/RNA hybrid
<220> FEATURE:
<221> NAME/KEY: misc_feature
<222> LOCATION: (1)..(23)
<223> OTHER INFORMATION: Nucleotide at positions 1-23 is RNA
<220> FEATURE:
<221> NAME/KEY: misc_feature
<222> LOCATION: (24)..(25)
<223> OTHER INFORMATION: Nucleotide at positions 24-25 is DNA

<400> SEQUENCE: 5
gaaugugggu ggcaacuuua aagga                                          25
```

```
<210> SEQ ID NO 6
<211> LENGTH: 27
<212> TYPE: RNA
<213> ORGANISM: Artificial Sequence
<220> FEATURE:
<223> OTHER INFORMATION: Synthetic

<400> SEQUENCE: 6
uccuuuaaag uugccaccca cauucag                                            27

<210> SEQ ID NO 7
<211> LENGTH: 38
<212> TYPE: PRT
<213> ORGANISM: Artificial Sequence
<220> FEATURE:
<223> OTHER INFORMATION: Synthetic

<400> SEQUENCE: 7

Arg Gln Ile Lys Ile Trp Phe Gln Asn Arg Arg Met Lys Trp Lys Lys
1               5                   10                  15

Met Gly Gln Val Gly Arg Gln Leu Ala Ile Ile Gly Asp Asp Ile Asn
            20                  25                  30

Arg Arg Tyr Asp Ser Cys
        35
```

POLYMERIC CARRIER

CROSS-REFERENCE

This application claims the benefit of U.S. Provisional Application No. 61/052,908, filed May 13, 2008, U.S. Provisional Application No. 61/052,914, filed May 13, 2008, U.S. Provisional Application No. 61/091,294, filed Aug. 22, 2008, U.S. Provisional Application No. 61/112,054, filed Nov. 6, 2008, U.S. Provisional Application No. 61/140,779, filed Dec. 24, 2008, U.S. Provisional Application No. 61/171,358 filed Apr. 21, 2009, which applications are incorporated herein by reference.

STATEMENT AS TO FEDERALLY SPONSORED RESEARCH

This invention was made with Government support under Contract No. NIH1RO1EB002991, awarded by the National Institutes of Health. The Government has certain rights in the invention.

BACKGROUND OF INVENTION

In certain instances, it is beneficial to provide polynucleotides (e.g., oligonucleotides) to living cells. In some instances, delivery of such polynucleotides to a living cell provides a therapeutic benefit.

SUMMARY OF THE INVENTION

Described herein are compositions for delivering at least one nucleotide and/or other therapeutic agent into a cell (i.e., intracellular delivery). In certain embodiments, such intracellular delivery is in vitro and in other embodiments, such intracellular delivery is in vivo. In certain embodiments the compositions for delivery comprise polymers, including polymeric carriers. Such polymeric carriers are optionally in the form of micelles, and in particular, true micelles. Thus, described herein are polymeric carriers (e.g., micelles) in combination with at least one nucleotide and/or other therapeutic agent. Such combinations are optionally in the form of covalent and/or non-ovalent interactions. Such combinations optionally further include additional agents, such as agents for targeting the combinations to a desired cell. Further described herein are uses of such intracellular delivery compositions for therapeutic and/or diagnostic purposes. Such uses include altering gene expression in the cell, for example, the knock-down or activation of a gene in the cell.

Provided in certain embodiments herein is a polymeric carrier comprising (i) a plurality of polymers assembled into a polymeric carrier, the polymeric carrier comprising a core and a shell, the polymers comprising: at least one hydrophobic portion; a plurality of monomeric units comprising a first anionic species at about neutral pH; and (ii) at least one nucleotide (e.g., at least one polynucleotide). In certain embodiments, the polymers include copolymers, block copolymers, or the like. When the pH is at about the $pK_a$ of the chargeable species, there will exist an equilibrium distribution of chargeable species in both forms. In the case of an anionic species, about 50% of the population will be anionic and about 50% will be non-charged when the pH is at the $pK_a$ of the anionic species. The further the pH is from the $pK_a$ of the chargeable species, there will be a corresponding shift in this equilibrium such that at higher pH values, the anionic form will predominate and at lower pH values, the uncharged form will predominate. The embodiments described herein include the form of the copolymers at any pH value.

Provided in certain embodiments herein is a polymeric carrier comprising:
a. a plurality of polymers that are block copolymers assembled into a polymeric carrier, the polymeric carrier comprising a core and a shell, the block copolymers comprising:
  i. at least one hydrophobic block;
  ii. a plurality of monomeric units comprising a plurality of anionic species at about neutral pH; and
b. at least one nucleotide (e.g., at least one polynucleotide).

In specific embodiments, the at least one nucleotide (e.g., at least one polynucleotide) is not present in the core of the polymeric carrier.

Provided in some embodiments herein is a polymeric carrier (polymeric composition) comprising:
a. a plurality of polymers that are block copolymers assembled into a polymeric carrier, the polymeric carrier comprising a core and a shell, the copolymers comprising:
  i. at least one hydrophobic block, the hydrophobic block comprising a plurality of anionic species at about neutral pH;
  ii. a polynucleotide carrier block, the polynucleotide carrier block being hydrophilic at about neutral pH;
b. at least one polynucleotide.

In some embodiments, the polynucleotide carrier block is polycationic at about neutral pH, is polyanionic at about neutral pH, is non-charged (e.g., substantially non-charged) at about neutral pH, or is zwitterionic at about neutral pH. In some embodiments, about neutral pH is a pH of about 7 (e.g., about 7.2 to about 7.4).

Provided in some embodiments herein is a polymeric carrier (polymeric composition) comprising:
a. a plurality of polymers that are block copolymers assembled into a polymeric carrier, the polymeric carrier comprising a core and a shell, the copolymers comprising:
  i. at least one hydrophobic block, the hydrophobic block comprising a plurality of anionic species at about neutral pH;
  ii. a polynucleotide carrier block, the polynucleotide carrier block being polycationic at about neutral pH;
b. at least one polynucleotide.

In specific embodiments, the polynucleotide is not in the core of the polymeric carrier. In some specific embodiments, the at least one hydrophobic block comprises a plurality of cationic species at about neutral pH.

Provided in certain embodiments herein is a polymeric carrier (or polymeric composition) comprising:
a. a plurality of polymers that are block copolymers assembled into a polymeric carrier, the polymeric carrier comprising a core and a shell, the block copolymers comprising:
  i. at least one hydrophobic block, the hydrophobic block comprising a plurality of anionic species at about neutral pH;
  ii. a polynucleotide carrier block;
b. at least ten polynucleotides, the polynucleotides not being in the core of the polymeric carrier.

In specific embodiments, the polymeric carrier (a polymeric composition) comprises at least twenty polynucleotides.

Provided in some embodiments herein is a polymeric carrier comprising:
  a. a plurality of polymers that are block copolymers assembled into a polymeric carrier, the polymeric carrier comprising a core and a shell, the block copolymers comprising:
    i. at least one hydrophobic block;
    ii. a plurality of anionic species at about neutral pH; and
  b. at least one polynucleotide, In specific embodiments, the polymeric carrier having a hydrodynamic diameter of about 10 nm to about 200 nm in an aqueous medium with a pH of about 7.4.

In some embodiments, the at least one nucleotide of any polymeric carrier described herein is attached to the polymeric carrier (or a component polymer thereof), wherein such attachment is achieved in any suitable manner (e.g., non-covalent interactions, such as electrostatic interactions, hydrophobic interactions, hydrophilic interactions, or the like; covalent interactions; or the like; or combinations thereof). In certain embodiments, at least one nucleotide of any of the polymeric carriers described herein is a polynucleotide (e.g., a first polynucleotide). In some embodiments, the polymeric carrier comprises a plurality of polynucleotides (e.g., a plurality of first polynucleotides and/or a plurality of second polynucleotides, and as many additional different polynucleotides as desired). In specific embodiments, the polynucleotide is a gene expression modulator. In more specific embodiments, gene expression modulators include knockdown agents (e.g., a knockdown oligonucleotide). In more specific embodiments, the knockdown agent is an siRNA, an antisense oligonucleotide, an miRNA, or an shRNA. In still more specific embodiments, the knockdown agent is an siRNA.

In some embodiments, any polymeric carrier described herein comprises a targeting moiety. In specific embodiments, the targeting moiety is attached to the shell portion of the polymeric carrier. In more specific embodiments, the targeting moiety is attached to the shell portion by a covalent bond to a polynucleotide.

In certain embodiments, the polymer of any polymeric carrier provided herein is a block copolymer, a monoblock copolymer, or a gradient polymer. In some embodiments, any polymeric carrier described herein further comprises an additional polymer that is not attached to a polynucleotide. In some embodiments, the additional polymer is a diluent polymer or a targeting moiety carrier polymer. In certain embodiments, any polymeric carrier provided herein further comprises an additional polymer that is attached to at least one second nucleotide (e.g., a second polynucleotide). In certain embodiments, the at least one second nucleotide (e.g., second polynucleotide) is different from the at least one nucleotide (e.g., a first polynucleotide).

In some embodiments, any polymeric carrier described herein comprises a plurality of polymers, each (all) having a core portion in the polymeric carrier are substantially identical.

In certain embodiments, a polymeric carrier provided herein is membrane destabilizing In specific embodiments, the polymeric carrier is membrane destabilizing at acidic pH (e.g., endosomal pH), but not at about neutral pH.

In specific embodiments, provided herein is a polymeric carrier that is a micelle, and in particular a true micelle.

In certain embodiments, any of the polymeric carriers provided herein comprise polymers having a hydrophobic block, wherein the hydrophobic block comprises a plurality of first chargeable species. In some embodiments, the plurality of first chargeable species are substantially anionic at about neutral pH. In certain embodiments, the plurality of first chargeable species are substantially non-charged at an acidic pH, or an endosomal pH. In some embodiments, the plurality of first chargeable species are substantially non-charged at a pH of about 7 or less, about 6.8 or less, about 6.6 or less, about 6.4 or less, about 6.2 or less, about 6 or less, about 5.8 or less, or about 5.6 or less. In specific embodiments, the plurality of first chargeable species are substantially non-charged at a pH of about 6 or less. In specific embodiments, the form of the polynucleotide carrier block (e.g., polycationic, polyanionic, neutral or zwitterionic is substantially identical at an acidic pH (e.g., an endosomal pH) as it is about neutral pH.

In some embodiments, any of the polymeric carriers provided herein further comprises a plurality of hydrophobic monomeric units having a $\pi$ value of >1, the hydrophobic monomeric units being a part of the hydrophobic block or in addition to the hydrophobic block. A compound's $\pi$ value is a measure of its relative hydrophilic-lipophilic value (see, e.g., Cates, L. A., "Calculation of Drug Solubilities by Pharmacy Students" *Am. J. Pharm. Educ.* 45:11-13 (1981)).

In certain embodiments, any of the polymeric carriers provided herein comprise a plurality of polymers that have spontaneously self-assembled into the polymeric carrier. In some embodiments, any of the polymeric carriers provided herein comprise one or more polymer wherein the at least one nucleotide (e.g., polynucleotide) is a block of the polymer. In some embodiments, the polynucleotide forms or is present in the shell of the polymeric carrier. In certain embodiments, any of the polymeric carriers provided herein comprise at least one polynucleotide in the shell of the polymeric carrier. In some embodiments, any of the polymeric carriers provided herein comprises a membrane-destabilizing chargeable hydrophobic block.

In some embodiments, any of the polymeric carriers provided herein comprises at least one polymer that comprises a polynucleotide carrier block. In certain embodiments, the shell of the polymeric carrier comprises the polynucleotide carrier block. In some embodiments, the polynucleotide carrier block is non-peptidic (i.e., is not a poly-amino acid). In certain embodiments, the at least one nucleotide of a polymeric carrier provided herein is attached to the polynucleotide carrier block by a covalent bond, a non-covalent interaction, or a combination thereof. In some embodiments, the polynucleotide carrier block of any polymeric carrier described herein is polycationic. In certain embodiments, the polynucleotide carrier block is an siRNA carrier block. In some embodiments, the polynucleotide carrier block (e.g., siRNA carrier block) is not PEGylated. In more specific embodiments, the backbone of the polynucleotide carrier block is not PEGylated. In certain embodiments the at least one nucleotide (e.g., polynucleotide, including oligonucleotide) is a polyanion comprising x anions, and wherein the polynucleotide carrier block (e.g., siRNA carrier block) comprises about 0.7·x cations, or more. In certain embodiments, the polynucleotide carrier block of any polymeric carrier provided herein is a homopolymeric block. In specific embodiments, the homopolymeric block is poly-N,N-di($C_1$-$C_6$)alkyl-amino($C_1$-$C_6$)alkyl-ethacrylate, poly-N,N-di($C_1$-$C_6$)alkyl-amino($C_1$-$C_6$)alkyl-methacrylate, or poly-N,N-di($C_1$-$C_6$)alkyl-amino($C_1$-$C_6$)alkyl-acrylate. In some embodiments, a polynucleotide carrier block is a copolymer comprising, e.g., (i) at least one N,N-di($C_1$-$C_6$)alkyl-amino($C_1$-$C_6$)alkyl-ethacrylate monomeric unit, at least one N,N-di($C_1$-$C_6$)alkyl-amino($C_1$-$C_6$)alkyl-methacrylate, at least one N,N-di($C_1$-$C_6$)alkyl-amino($C_1$-$C_6$)alkyl-acrylate, or a combination thereof; and (ii) at least one spacer monomeric unit.

In some embodiments, a polymeric carrier provided herein comprises a first chargeable species that is a carboxylic acid group, a sulfonamide group, a sulfonic acid group, a sulfinic acid group, a sulfuric acid group, a phosphoric acid group, a phosphinic acid group, or a phosphorous acid group. In certain embodiments, a polymer of any polymeric carrier provided herein comprises a spacer monomeric unit in any block (e.g., a hydrophobic block, a hydrophilic block, a shell block, a core block, or the like). In some embodiments, any polymeric carrier provided herein comprising a hydrophobic block that comprises at least one spacer monomeric unit.

In certain embodiments, a polymeric carrier provided herein comprises a hydrophobic block comprising a first and a second chargeable species. In some embodiments, the first chargeable species is as described herein and the second chargeable species is a cationic species upon protonation. In specific embodiments, the pKa of the second chargeable species is about 6.5 to about 9. In some embodiments, the second chargeable species is an acyclic amine or imine, a cyclic amine or imine, or a nitrogen containing heteroaryl. In certain embodiments, at least one of the first chargeable species and at least one of the second chargeable species are present on a single monomeric unit. In some embodiments, the first chargeable species is found on a first chargeable monomeric unit and the second chargeable species is on a second chargeable monomeric unit. In certain embodiments, the first chargeable species is an anionic species upon deprotonation, the second chargeable species is a cationic species upon protonation, and wherein the ratio of the anionic species to the cationic species is between about 1:4 and about 4:1 at about a neutral pH. In some embodiments, the ratio of the first chargeable monomeric unit to the second chargeable monomeric unit is about 1:4 to about 4:1. In certain embodiments, the first chargeable monomeric unit is a $(C_2-C_8)$alkylacrylic acid. In some embodiments, less than 50% of the second chargeable monomeric unit is charged to a cationic species at a pH of about 8. In certain embodiments, the second chargeable monomeric unit is N,N-di$(C_1-C_6)$alkyl-amino$(C_1-C_6)$alkyl-ethacrylate, N,N-di$(C_1-C_6)$alkyl-amino$(C_1-C_6)$alkyl-methacrylate, or N,N-di$(C_1-C_6)$alkyl-amino$(C_1-C_6)$alkyl-acrylate.

In certain embodiments, the polymeric carrier comprises more than 5, more than 20, more than 50, or more than 100 chargeable species that are charged or chargeable to anionic species. In some embodiments, the polymeric carrier comprises more than 5, more than 20, more than 50, or more than 100 chargeable species that are charged or chargeable to cationic species. In certain embodiments, the polymeric carrier comprises more than 5, more than 20, more than 50, or more than 100 first chargeable species. In specific embodiments, each first chargeable species is charged or chargeable to an anionic species. In certain embodiments, the polymeric carrier comprises more than 5, more than 20, more than 50, or more than 100 second chargeable species. In specific embodiments, each second chargeable species is charged or chargeable to a cationic species. In certain embodiments, the hydrophobic block of the block copolymers present in the polymeric carrier provided herein comprises more than 5, more than 20, more than 50, or more than 100 first chargeable species. In specific embodiments, each first chargeable species is charged or chargeable to an anionic species. In some embodiments, the hydrophobic block of the block copolymers present in the polymeric carrier provided herein comprise more than 5, more than 20, more than 50, or more than 100 second chargeable species. In specific embodiments, each second chargeable species is charged or chargeable to a cationic species.

Provided in certain further or alternative embodiments of any polymeric carrier embodiment described herein is a polymeric carrier comprising a membrane-destabilizing chargeable hydrophobic block comprising a plurality of non-chargeable monomeric units. In some instances, the non-chargeable monomeric unit comprises the hydrophobic species. In other instances, first and/or second chargeable species comprise or also comprise the hydrophobic species. In some embodiments, the non-chargeable monomeric unit is a $(C_2-C_8)$alkyl-ethacrylate, a $(C_2-C_8)$alkyl-methacrylate, or a $(C_2-C_8)$alkyl-acrylate.

In some embodiments, any polymeric carrier provided herein has an average hydrodynamic diameter in an aqueous medium at a pH of about 7.4 of about 10 nm to about 200 nm. In some embodiments, the polymeric carrier has an average hydrodynamic diameter in an aqueous medium at a pH of about 7.4 of about 20 nm to about 100 nm. In certain embodiments, the polymeric carrier has an average hydrodynamic diameter in an aqueous medium at a pH of about 7.4 of about 30 nm to about 80 nm.

In some embodiments, provided herein is a polymeric carrier comprising at least 1, at least 2, at least 5, at least 20, at least 25, at least 30, at least 40, at least 50, at least 100, at least 200, or least 250 polynucleotides (e.g., oligonucleotides or siRNA). In some embodiments, provided herein is a polymeric carrier comprising between 1 and about 250, between 2 and about 250, between 5 and about 250, between 20 and about 250, between about 25 and about 250, between about 30 and about 250, between 40 and about 250, between 50 and about 250, between about 100 and about 250, and between 200 and about 250 individual polynucleotides (e.g., oligonucleotides or siRNA). In certain embodiments, provided herein is a polymeric carrier comprising at least 2 polynucleotides (e.g., oligonucleotides or siRNA). In certain embodiments, such polynucleotides are attached in any suitable manner to the polymeric carriers and/or the polymers therein. In some embodiments, the polynucleotide is an siRNA.

In certain embodiments, any polymeric carrier provided herein comprises a block copolymer wherein the ratio of the number average molecular weight of the hydrophobic block to the number average molecular weight of the polynucleotide carrier block is about 1:5 to about 5:1, or about 1:1 to about 5:1 (or, e.g., about 5:4 to 5:1). In some embodiments, the ratio of the number average molecular weight of the hydrophobic block to the number average molecular weight of the polynucleotide carrier block is about 3:2 to about 3:1. In specific embodiments, the ratio of the number average molecular weight of the hydrophobic block to the number average molecular weight of the polynucleotide carrier block is about 2:1.

In certain embodiments, any polymeric carrier provided herein comprises a polynucleotide carrier block that is an siRNA carrier block. In some embodiments, the siRNA carrier block has a number average molecular weight (Mn) of about 7,000 dalton to about 50,000 dalton. In some embodiments, the siRNA carrier block has a number average molecular weight (Mn) of about 7,000 dalton to about 20,000 dalton. In certain embodiments, the siRNA carrier block has a number average molecular weight (Mn) of about 10,000 dalton to about 20,000 dalton. In some embodiments, the siRNA carrier block has a number average molecular weight (Mn) of about 10,000 dalton. In certain embodiments, the siRNA carrier block has a number average molecular weight (Mn) of about 20,000 dalton. In some embodiments, the hydrophobic block has a number average molecular weight (Mn) of about 2,000 dalton to about 200,000 dalton, about 2,000 dalton to about 200,000 dalton, about 2,000 dalton to about 100,000 dalton, or about 10,000 dalton to about 100,000 dalton. In some embodiments, the hydrophobic block has a number average molecular weight (Mn) of about 10,000 dalton to about 50,000 dalton. In certain embodiments, the hydrophobic block has a number average molecular weight (Mn) of about 20,000 dalton to about 50,000 dalton. In some embodiments, the polymeric carrier provided herein comprises a plurality of membrane destabilizing block copolymers with a core block having a number average molecular weight (Mn) of greater than 100,000 dalton. In some embodiments, the polymeric carrier provided herein comprises a plurality of membrane destabilizing block copolymers with a shell block having a number average molecular weight (Mn) of greater than 50,000 dalton.

In some embodiments, the block copolymers of any polymeric carrier provided herein have a polydispersity index of less than 2, less than 1.8, less than 1.6, less than 1.5, less than 1.4, or less than 1.3.

In some embodiments, any polymeric carrier provided herein is stable at a pH of about 7.4. In certain embodiments, the polymeric carrier is substantially less stable at a pH of about 5.8 than at a pH of about 7.4. In some embodiments, greater than 90% of the polymeric carrier is destabilized at a pH of about 5.8 and a concentration of about 18 µg/mL and less than 10% of the polymeric carrier is destabilized at a pH of about 7.4 and a concentration of about 18 µg/mL.

In certain embodiments, any polymeric carrier provided herein is stable in 50% human serum for at least 2 hours, at least 4 hours, at least 6 hours, at least 8 hours, at least 12 hours, at least 18 hours, at least 24 hours, at least 48 hours, or more. In some embodiments, any polymeric carrier provided herein is stable in at least 50% human plasma for at least 2 hours, at least 4 hours, at least 6 hours, at least 8 hours, at least 12 hours, at least 18 hours, at least 24 hours, at least 48 hours, or more. In certain embodiments, any polymeric carrier provided herein is stable in 50% mouse serum for at least 2 hours, at least 4 hours, at least 6 hours, at least 8 hours, at least 12 hours, at least 18 hours, at least 24 hours, at least 48 hours, or more. In certain embodiments, any polymeric carrier provided herein is stable in 50% mouse plasma for at least 2 hours, at least 4 hours, at least 6 hours, at least 8 hours, at least 12 hours, at least 18 hours, at least 24 hours, at least 48 hours, or more. In some embodiments, any polymeric carrier provided herein is stable in 50% human serum for at least 2 hours, in at least 50% human plasma for at least 2 hours, in 50% mouse serum for at least 2 hours, in 50% mouse plasma for at least 2 hours, or a combination thereof.

In certain embodiments described herein are any of the polymers that make up the polymeric carriers described herein. That is, the polymeric subunits (e.g., the membrane-destabilizing block copolymers) or the individual polymers (whether or not in the form of a polymeric carrier) are also embodiments described herein. To be explicit, each and every membrane-destabilizing block copolymer that is presented herein is within the scope of the inventions described herein, both as an individual polymer, or as a polymeric unit/strand/component of the polymeric carriers described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A: An illustrative example of the composition and properties of RAFT synthesized polymers FIG. 1B: An illustrative example of the composition and properties of PEGMA-DMAEMA copolymers

FIG. 3: An illustrative example of the dynamic light scattering (DLS) determination of particle size of polymer PRx0729v6 complexed to siRNA.

FIG. 7: An illustrative example of the knock-down activity of siRNA—micelle complexes in cultured mammalian cells.

FIG. 11: An illustrative example of the effect of pH on polymer structure.

FIG. 12: An illustrative summary of knock-down data for siRNA—micelle complexes in cultured mammalian cells.

FIG. 15: An illustrative example of the RAFT Co-polymerization of PEGMA and MAA-NHS

DETAILED DESCRIPTION OF THE INVENTION

Figure 2A:
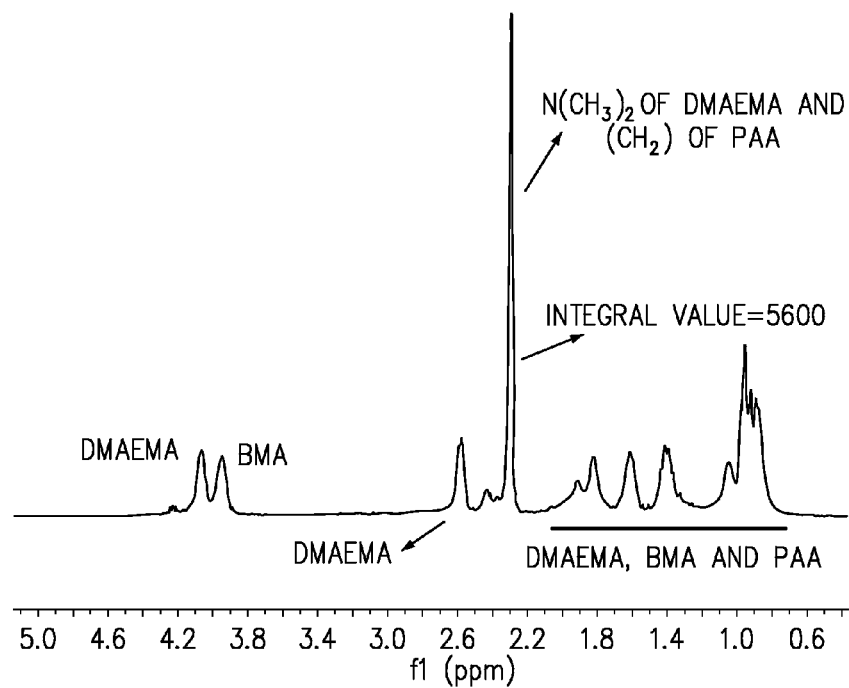
FIG. 2: An illustrative example of the NMR spectroscopy of block copolymer PRx0729v6.

Provided herein are polymeric carriers suitable for the delivery of polynucleotides (including, e.g., oligonucleotides) to a living cell. In some embodiments, the polymeric carriers comprise a plurality of polymeric units and, optionally, at least one polynucleotide. In certain embodiments, the polymeric carriers provided herein are biocompatible, stable (including chemically and/or physically stable), and/or reproducibly synthesized. Additionally, in some embodiments, the carriers provided herein are non-toxic (e.g., exhibit low toxicity), protect the polynucleotide (e.g., oligonucleotide) payload from degradation, enter living cells via a naturally occurring process (e.g., by endocytosis), and/or deliver the polynucleotide (e.g., oligonucleotide) payload into the cytoplasm of a living cell after being contacted with the cell. In certain instances, the polynucleotide (e.g., oligonucleotide) is an siRNA and/or another 'nucleotide-based' agent that alters the expression of at least one gene in the cell. Accordingly, in certain embodiments, the carriers provided herein are useful for delivering siRNA into a cell. In certain instances, the cell is in vitro, and in other instances, the cell is in vivo. In some embodiments, a therapeutically effective amount of the polymeric carrier comprising an siRNA is administered to an individual in need thereof (e.g., in need of having a gene knocked down, wherein the gene is capable of being knocked down by the siRNA administered). In specific instances, the polymeric carriers are useful for or are specifically designed for delivery of siRNA to specifically targeted cells of the individual.

Specifically, provided in certain embodiments herein is a polymeric carrier with a core-shell structure comprising: (i) a plurality of block copolymers assembled into a polymeric carrier; and (ii) at least one oligonucleotide which is in the shell of the carrier. In certain embodiments, the polymeric carrier is a nanoparticle. In specific embodiments, the polymeric carrier is a micelle, and in particular a true micelle. In some embodiments, a polymeric carrier provided herein comprises a.) a plurality of polymers that are block copolymers assembled into a polymeric carrier, the polymeric carrier comprising a core and a shell, the block copolymers comprising (i.) at least one hydrophobic block, and (ii.) a plurality of monomeric units comprising a first anionic species at about neutral pH, and b.) at least one polynucleotide.

In one embodiment, polymeric carriers (e.g., micelles) provided herein, or the component parts thereof, are membrane-destabilizing (e.g., comprise a membrane destabilizing block, group, moiety, or the like). In further or alternative embodiments, the plurality of block copolymers form a shell and a core of a polymeric carrier (e.g., micelle). In specific embodiments, the polymeric carrier comprises a hydrophilic and/or charged shell. In further or alternative embodiments, the polymeric carrier comprises a substantially hydrophobic core (e.g., the core comprises hydrophobic groups, monomeric units, moieties, blocks, or the like). In specific embodiments, one or more of the block copolymers each comprise (1) a hydrophilic, charged block forming the shell of the polymeric carrier (e.g., micelle); and (2) a substantially hydrophobic block forming the core of the polymeric carrier (e.g., micelle). In some embodiments, one or more of the block copolymers comprise a plurality of first chargeable species and a plurality of hydrophobicity enhancers. In specific embodiments, the first chargeable species are anionic chargeable species (e.g., are or become charged at a specific pH). In further embodiments, the one or more of the block copolymers comprise a second chargeable species. (i.e., the hydrophilic block may have more than one different type of anionic species) In certain embodiments, the polymeric carrier (e.g., micelle) comprises at least one polynucleotide (e.g., oligonucleotide). In specific embodiments, the polynucleotide (e.g., oligonucleotide) is not in the core of the polymeric carrier (e.g., micelle).

In certain embodiments, any of the polymeric carriers provided herein comprise polymers having a hydrophobic block, wherein the hydrophobic block comprises a plurality of first chargeable species. In some embodiments, the plurality of first chargeable species are substantially anionic at about neutral pH. In certain embodiments, the plurality of first chargeable species are substantially non-charged at an acidic pH, or an endosomal pH. In some embodiments, the plurality of first chargeable species are substantially non-charged at a pH of about 7 or less, about 6.8 or less, about 6.6 or less, about 6.4 or less, about 6.2 or less, about 6 or less, about 5.8 or less, or about 5.6 or less. In specific embodiments, the plurality of first chargeable species are substantially non-charged at a pH of about 6 or less. In certain embodiments, a polymeric carrier provided herein comprises a hydrophobic block comprising a first and a second chargeable species. In some embodiments, the first chargeable species is as described herein and the second chargeable species is a cationic species upon protonation. In specific embodiments, the pKa of the second chargeable species is about 6.5 to about 9, about 5 to about 9, about 6 to about 9, about 6 to about 8, or about 6.5 to about 8.

In some embodiments, any of the polymeric carriers provided herein further comprises a plurality of hydrophobic monomeric units, the hydrophobic monomeric units being a part of the hydrophobic block or in addition to the hydrophobic block.

In some embodiments, the polymeric carrier (e.g., a micelle) and/or the polymers therein are non-peptidic.

In some embodiments, a polymeric carrier (e.g., micelles) provided herein comprises a plurality of monoblock polymers. In certain embodiments, the monoblock polymers and/or the polymeric carrier (e.g., monomeric units, moieties, species and/or groups thereof) are membrane-destabilizing. In certain embodiments, at least one of the monoblock polymers comprises a plurality of anionic chargeable species, and a plurality of hydrophobic species. The polymeric carrier (e.g., micelle) comprises at least one polynucleotide (e.g., oligonucleotide). In specific embodiments, the polynucleotide (e.g., oligonucleotide) is not in the core of the polymeric carrier (e.g., micelle).

In one embodiment, membrane-destabilizing polymeric carriers (e.g., micelles) provided herein comprise a plurality of block copolymers. In some embodiments, these block copolymers form a shell and a core of the polymeric carrier (e.g., micelle). In certain embodiments, the shell and/or the shell block is hydrophilic and/or charged. In some embodiments, the core and/or the core block is substantially hydrophobic. In specific embodiments, the substantially hydrophobic core comprises positive and/or negative charges. In more specific embodiments, the hydrophobic core and/or core block comprises a substantially equal number of positive and negative charges (i.e., the charge of the core and/or core block is substantially net neutral). In some embodiments, one or more or all of the block copolymers each comprise (1) a hydrophilic, charged block forming the shell of the polymeric carrier (e.g., micelle); and (2) a substantially hydrophobic block forming the core of the polymeric carrier (e.g., micelle). In some embodiments, the block copolymers comprise a plurality of anionic chargeable species, a plurality of hydrophobic moieties, and are membrane destabilizing. The core of the polymeric carrier (e.g., micelle) or a core block of a block copolymer optionally comprises cationic species. In some embodiments, the polymeric carrier (e.g., micelle) or core block of a block copolymer optionally comprises an anionic species. In specific embodiments, the polymeric carrier (e.g., micelle) or core block of a block copolymer comprises at least one cationic species and at least one anionic species. The micelles also comprise at least one polynucleotide (e.g., oligonucleotide). In specific embodiments, the at least one polynucleotide (e.g., oligonucleotide) is not in the core of the micelle.

In some instances, the polymeric carriers (e.g., micelles) are formed from a plurality of block copolymers which self-associate through the interactions of the hydrophobic blocks (e.g., core blocks) of the block copolymers, and/or are stabilized through their hydrophobic interactions in the core. In some embodiments, the polymeric carriers (e.g., micelles) comprise two or more different species of block copolymers having different structures and functions.

In certain embodiments, the polymeric carriers provided herein are useful for delivering polynucleotides (e.g., oligonucleotides) to an individual in need thereof. In some embodiments, the polymer (e.g., block copolymer or monoblock polymer) of a polymeric carrier described herein comprises a polynucleotide carrier block (or polynucleotide carrier section in the case of a monoblock polymer). In some embodiments, the hydrophilic block or shell block of the block copolymer is or comprises the polynucleotide carrier block. The polynucleotide carrier block comprises one or more types of monomeric units (e.g., is a homopolymeric block or a heteropolymeric block). In some embodiments, the polymeric carrier comprises a polynucleotide (e.g., oligonucleotide) that is non-covalently and/or covalently attached to the polynucleotide carrier block of one or more block copolymers of the polymeric carrier. In specific embodiments, an siRNA is covalently attached to a block copolymer of the polymeric carrier (e.g., micelle). In some specific embodiments, an siRNA is non-covalently attached to a block copolymer of the polymeric carrier (e.g., micelle). In specific embodiments, an siRNA is non-covalently and covalently attached to a block copolymer of the polymeric carrier (e.g., micelle). In some specific embodiments, the siRNA forms (e.g., is present in) at least a portion of the shell of the polymeric carrier. In some specific embodiments, the siRNA is covalently attached to the hydrophobic block.

In certain embodiments, any polymeric carrier provided herein comprises a block copolymer wherein the ratio of the number average molecular weight of the hydrophobic block and/or core block to the number average molecular weight of the polynucleotide carrier block and/or shell block is about 1:10 to about 5:1, about 1:5 to about 5:1, or about 1:1 to about 5:1 (or, e.g., about 5:4 to 5:1). In some embodiments, the ratio of the number average molecular weight of the hydrophobic block and/or core block to the number average molecular weight of the polynucleotide carrier block and/or shell block is about 3:2 to about 3:1. In specific embodiments, the ratio of the number average molecular weight of the hydrophobic block and/or core block to the number average molecular weight of the polynucleotide carrier block and/or shell block is about 2:1.

In certain embodiments, the polymeric carriers provided herein comprise a plurality of membrane-destabilizing block copolymers. As such, the polymeric carriers are also described herein as membrane destabilizing because, at least in part, they are comprised of membrane-destabilizing block copolymers.

In some embodiments, a membrane-destabilizing block copolymer comprises (i) a plurality of hydrophobic monomeric residues, (ii) a plurality of anionic monomeric residues having a chargeable species, the chargeable species being anionic at serum physiological pH, and being substantially neutral or non-charged at an endosomal pH and (iii) optionally a plurality of cationic monomeric residues. In some embodiments, modification of the ratio of anionic to cationic species in a block copolymer allows for modification of membrane destabilizing activity of a polymeric carrier described herein. In some of such embodiments, the ratio of anionic:cationic species in a block copolymer ranges from about 4:1 to about 1:4 at serum physiological pH. In some of such embodiments, modification of the ratio of anionic to cationic species in a hydrophobic block of a block copolymer allows for modification of membrane destabilizing activity of a polymeric carrier described herein. In some of such embodiments, the ratio of anionic:cationic species in a hydrophobic block of a block copolymer described herein ranges from about 1:2 to about 3:1, or from about 1:1 to about 2:1 at serum physiological pH.

In some embodiments, the polymeric carriers described herein destabilize an endosomal membrane in a pH-dependent manner. In various embodiments, the membrane-destabilizing block copolymers destabilize a membrane when assembled in the polymeric carrier and/or when present independent of the assembled polymeric carrier form (e.g., when the polymeric carrier is disassociated and/or destabilized). In some embodiments, at or near physiological pH (e.g., circulating physiological pH), the polymers making up the polymeric carrier are minimally membrane-destabilizing, but upon exposure to decreased pH (e.g., endosomal pH), the polymer is membrane-destabilizing. In certain instances, this transition to a membrane-destabilizing state occurs via the protonation of weakly acidic residues that are incorporated into the polymers, such protonation leading to an increase in the hydrophobicity of the polymers. In certain instances, the increased hydrophobicity of the polymer results in a conformational change of the polymeric carrier, making the polymeric carrier membrane-destabilizing (e.g., causing destabilization of the membrane). In some embodiments, the mechanism of membrane destabilization of the polymeric carriers provided herein does not rely on a purely proton-sponge membrane destabilizing mechanism of polycations such as PEI or other polycations.

In certain embodiments, polymeric carriers provided herein comprise one or more polynucleotide, e.g., one or more oligonucleotide, one or more RNAi agent, one or more RNA, one or more DNA, one or more cDNA, one or more miRNA, one or more siRNA, one or more shRNA, one or more RNAa, one or more dicer substrate, or the like, or combinations thereof.

Polymeric Carriers.

In certain embodiments, the polymeric carrier is a nanoparticle. In specific embodiments, the polymeric carrier is a micelle. In yet further embodiments, the polymeric carrier is a micelle with the size of approximately 10 nm to about 200 nm, about 10 nm to about 100 nm, or about 30-80 nm. Particle size can be determined in any manner, including, but not limited to, by gel permeation chromatography (GPC), dynamic light scattering (DLS), electron microscopy techniques (e.g., TEM), and other methods.

In some embodiments, the polymeric carriers (e.g., micelles) provided herein are prepared by spontaneous self-assembly of the polymers described herein. In certain embodiments, the polymers described herein assemble into the polymeric carriers provided herein (a) upon dilution of a solution of the polymer in water-miscible organic solvent into aqueous media, or (b) being dissolved directly in an aqueous solution. In some embodiments, the polymers described herein assemble into the polymeric carriers provided herein in the absence of polynucleotides.

In some embodiments, the polymeric carriers (e.g., micelles) are stable to dilution in an aqueous solution. In specific embodiments, the polymeric carriers (e.g., micelles) are stable to dilution at about neutral pH with a critical stability concentration (e.g., a critical micelle concentration (CMC)) of approximately 50 to approximately 100 µg/mL, or approximately 10 to approximately 50 µg/mL, less than 10 µg/mL, less than 5 µg/mL, less than 2 µg/mL, less than 0.5 µg/mL, or less than 0.1 µg/mL. As used herein, "destabilization of a micelle" means that the polymeric chains forming a micelle at least partially disaggregate, structurally alter (e.g., expand in size and/or change shape), and/or may form amorphous supramolecular structures (e.g., non-micellic supramolecular structures). The terms critical stability concentration (CSC) and critical micelle concentration (CMC) are used interchangeably herein.

In specific embodiments, the polymeric carrier (e.g., micelle) comprises a plurality of block copolymers forming a shell and a core of the polymeric carrier (e.g., a micelle). In certain embodiments, the shell and/or shell block is hydrophilic and/or charged (e.g., cationic, polycationic, or zwitterionic). In specific embodiments, the shell and/or shell block comprises a net positive charge. In some embodiments, the core and/or core block is hydrophobic and/or comprises hydrophobic groups, moieties, monomeric units, species, or the like. In specific embodiments, the hydrophobic core and/or core block comprise a plurality of hydrophobic groups, moieties, monomeric units, species, or the like and a plurality of chargeable species or monomeric units. In more specific embodiments, the plurality of chargeable monomeric units or species comprises a plurality of anionic chargeable monomeric units or species. In still more specific embodiments, the plurality of chargeable monomeric units or species comprises a plurality of cationic and a plurality of anionic chargeable monomeric units or species. In some embodiments, the block copolymers each have (1) a hydrophilic, charged block (e.g., cationic or polycationic) forming the shell of the polymeric carrier (e.g., micelle), (2) a hydrophobic block, and (3) a plurality of anionic chargeable species, and are membrane destabilizing (e.g., become membrane destabilizating in a pH dependent manner). In certain embodiments, the hydrophobic core and/or core block optionally comprise spacer monomeric units which may or may not comprise hydrophobic groups, chargeable groups, or a combination thereof. In some embodiments, a polymer block forming or present in the core of the polymeric carrier (e.g., micelle) (e.g., one or more core block of the copolymer) is chargeable (e.g., contains cationic and/or anionic species at a physiological pH). As used herein, chargeable species and/or monomeric units include species and monomeric units in both the charged and non-charged states. In some instances, the polymeric carriers (e.g., micelles) provided herein are formed from a plurality of block copolymers which self-associate. In certain instances, the self-association occurs through the interactions of the hydrophobic blocks of the block copolymers and the resulting polymeric carriers (e.g., micelles) are stabilized through hydrophobic interactions of the hydrophobic blocks present in the core of the polymeric carrier.

In some embodiments, the polymeric carrier provided herein is stable at a pH of about 7.4 and is substantially less stable at a pH of about 5.8 than at a pH of about 7.4. In some instances, greater than 90% of the polymeric carrier is destabilized at a pH of about 5.8 and a concentration of about 10 µg/mL and less than 10% of the polymeric carrier is destabilized at a pH of about 7.4 and a concentration of about 10 µg/mL.

In some embodiments, the polymeric carriers (e.g., micelles) provided herein retain activity (e.g., the activity of the polymeric carrier to deliver a polynucleotide) in 50% human serum for at least 2 hours, at least 4 hours, at least 6 hours, at least 8 hours, at least 12 hours, or at least 24 hours. In further or alternative embodiments, the polymeric carriers (e.g., micelles) provided herein retain activity (e.g., the activity of the polymeric carrier to deliver a polynucleotide) in at least 50% human plasma for at least 2 hours, at least 4 hours, at least 6 hours, at least 8 hours, at least 12 hours, or at least 24 hours. In further or alternative embodiments, the polymeric carriers (e.g., micelles) provided herein retain activity (e.g., the activity of the polymeric carrier to deliver a polynucleotide) in 50% mouse serum for at least 2 hours, at least 4 hours, at least 6 hours, at least 8 hours, at least 12 hours, or at least 24 hours. In still further or alternative embodiments, the polymeric carriers (e.g., micelles) provided herein retain activity (e.g., the activity of the polymeric carrier to deliver a polynucleotide) in at least 50% mouse plasma for at least 2 hours, at least 4 hours, at least 6 hours, at least 8 hours, at least 12 hours, or at least 24 hours. In specific embodiments, the polymeric carriers (e.g., micelles) provided herein retain activity (e.g., the activity of the polymeric carrier to deliver a polynucleotide) in 50% human serum for at least 2 hours, in at least 50% human plasma for at least 2 hours, in 50% mouse serum for at least 2 hours, in at least 50% mouse plasma for at least 2 hours, or a combination thereof.

In some embodiments, a polymeric carrier (e.g., micelle) provided herein is characterized by one or more of the following: (1) the polymeric carrier (e.g., micelle) is formed by spontaneous self association of block copolymers to form organized assemblies (e.g., micelles) upon dilution from a water-miscible solvent (such as but not limited to ethanol) to aqueous solvents (for example phosphate-buffered saline, pH 7.4); (2) the polymeric carrier (e.g., micelle) is stable to dilution (e.g., down to a polymer concentration of 100 ug/ml, 50 ug/ml, 10 µg/ml, 5 µg/mL, 2 µg/mL, 0.5 µg/mL, or 0.1 µg/mL which constitutes the critical stability concentration or the critical micelle concentration (CMC)); (3) the polymeric carrier (e.g., micelle) is stable to high ionic strength of the surrounding media (e.g. 0.5M NaCl); and/or (4) the polymeric carrier (e.g., micelle) has an increasing instability as the concentration of organic solvent increases, such organic solvents including, but not limited to dimethylformamide (DMF), dimethylsulfoxide (DMS), and dioxane. In some embodiments, a polymeric carrier (e.g., micelle) provided herein is characterized by having at least two of the aforementioned properties. In some embodiments, a polymeric carrier (e.g., micelle) provided herein is characterized by having at least three of the aforementioned properties. In some embodiments, a polymeric carrier (e.g., micelle) provided herein is characterized by having all of the aforementioned properties.

In certain embodiments, polymeric carriers (e.g., micelles) provided herein are further or alternatively characterized by other criteria: (1) the molecular weight of the individual blocks and their relative length ratios is decreased or increased in order to govern the size of the micelle formed and its relative stability and (2) the size of the polymer cationic block that forms the shell is varied in order to provide effective complex formation with and/or charge neutralization of the oligonucleotide drug.

In certain embodiments, micelles of the present invention selectively uptake small hydrophobic molecules such as pyrene into the hydrophobic core of the micelle.

Polymeric Carriers Comprising Polynucleotides.

In some embodiments, the polymeric carriers provided herein are useful for delivering polynucleotides (e.g., oligonucleotides) to an individual in need thereof. In certain embodiments, provided herein is a polymeric carrier comprising at least one polynucleotide. In more specific embodiments, the polymeric carrier comprises at least 2, at least 4, at least 5, at least 10, at least 20, at least 30, at least 40, at least 50, at least 100 polynucleotides. In some embodiments, the polymeric carrier provided herein comprises 2-50 polynucleotides, 5-40 polynucleotides, 5-30 polynucleotides, 5-25 polynucleotides, 20-40 polynucleotides, or the like. In certain embodiments, the polynucleotide is an oligonucleotide gene expression modulator. In further embodiments, the polynucleotide is an oligonucleotide knockdown agent. In specific embodiments, the polynucleotide is an RNAi agent, dicer substrate, or siRNA. In other specific embodiments, the polynucleotide is an aiRNA (Asymmetric RNA duplexes mediate RNA interference in mammalian cells. Xiangao Sun, Harry A Rogoff, Chiang J Li *Nature Biotechnology* 26, 1379-1382 (2008)). In certain embodiments, the polymeric carrier is a nanoparticle (e.g., a micelle) comprising a core, a shell and one or more polynucleotides, wherein the polynucleotide is not in the core of the micelle. In specific embodiments, the polynucleotide is incorporated into (e.g., is present in and/or forms a portion of) the shell of the polymeric carrier. In some embodiments, one or more polynucleotide (e.g., oligonucleotide or siRNA) is attached to siRNA polynucleotide carrier block of the polymeric carrier-forming multi-block copolymers. In various embodiments, attachment is achieved through one or more covalent bond, one or more non-covalent interaction, or a combination thereof. In some embodiments, the siRNA is covalently attached to a hydrophobic block of the block copolymer (e.g., a core block). In specific embodiments, the siRNA is covalently attached to a hydrophobic block (e.g., a core block) of the block copolymer and forms at least a portion of the shell of the polymeric carrier. In more specific embodiments, the siRNA is a hydrophilic block (e.g., a shell block) of the block copolymer. In other embodiments, the siRNA is attached to the hydrophilic block of a block copolymer, or to an optional polymer block.

In some embodiments, one or more polynucleotide (e.g., oligonucleotide or siRNA) is attached to a block copolymer provided herein in any manner suitable, e.g., by non-covalent association. Non-covalent association between (i) a polymer and/or an assembly of polymers provided herein (e.g., a micelle formed by a plurality of polymers) and (ii) one or more polynucleotide (e.g., oligonucleotide) is achieved in any suitable manner, including, but not limited to, electrostatic interaction (including electrostatic interaction with a polymer having cationic groups and a polynucleotide having anionic groups), hydrophobic interaction, affinity interaction, or a combination thereof. In certain embodiments, the one or more polynucleotide and/or the polymers of the polymeric carrier (e.g., micelle) is modified with chemical moieties that afford one or more polynucleotide and/or polymers that have an affinity for one another (e.g., and are commercially viable), such as arylboronic acid-salicylhydroxamic acid, leucine zipper or other peptide motifs, ionic interactions between positive and negative charges on the micelle and polynucleotide, or other types of non-covalent chemical affinity linkages. Additionally, in some embodiments, a double-stranded polynucleotide is associated with (e.g., complexed to) a polymer or polymeric carrier (e.g., micelle) described herein. In some embodiments, a polymer or polymeric carrier (e.g., micelle) is associated (e.g., complexed) with a nucleic acid minor groove binding agent or an intercalating agent that is attached (e.g., covalently) to a component (e.g., a polymer) of the polymeric carrier (e.g., micelle).

In some embodiments, the polynucleotide (e.g., oligonucleotide) comprises at least one negative charge (e.g., comprises a negatively charged backbone) and is associated with a cationic shell of the polymeric carrier (e.g., micelle) and/or a cationic shell block of a block copolymer of the polymeric carrier. In specific embodiments, the cationic shell or shell block at least partially neutralizes the negative charges present in the one or more polynucleotides (e.g., oligonucleotides) attached to or present in the polymeric carrier. In certain embodiments, one or more polynucleotide (e.g., one or more oligonucleotide, one or more siRNA, or a combination thereof) forms an association (e.g., a complex) with the polycationic polynucleotide carrier blocks of the polymeric carrier (e.g., micelle). In some embodiments, the association (e.g., complex) between the polymeric carrier (e.g., micelle) and polynucleotide (e.g., oligonucleotide or siRNA) forms at any desired charge ratio of block copolymer forming the polymeric carrier (e.g., micelle) to polynucleotide (e.g., oligonucleotide or siRNA), e.g., between 1:1 and 16:1. In specific embodiments, the complex between the micelle and siRNA forms at the charge ratio of 2:1, 4:1 or 8:1. In other words, in some embodiments, the ratio of the number of cationic charges present in the shell of the polymeric carrier to the number of anionic charges present in the polynucleotide is any desired value, e.g., about 1:1 to about 16:1, about 2:1 to about 8:1, about 4:1 to about 12:1, about 2:1, about 4:1, or about 8:1. In some embodiments, siRNA is charge-neutralized by a polycationic block of a block copolymer forming the micelle. For example, in some specific embodiments, a 20-base pair polynucleotide (e.g., oligonucleotide or siRNA) comprising 40 negative charges at physiologic pH is associated (e.g., complexed) with a polymeric carrier (e.g., micelle) comprising a polyDMAEMA polynucleotide carrier block (80 monomeric units in length, MW=11,680) with a pKa of about 7.4. At this pH, polyDMAEMA contains 40 negative charges, thereby resulting in a polynucleotide-polynucleotide carrier block association (e.g., complex) that is substantially net neutral in charge. In certain instances, avoiding a large number of excess positive charges helps to reduce in vitro and in vivo toxicity. In some embodiments, a polynucleotide (e.g., oligonucleotide or siRNA) spontaneously associates with a positively charged shell of a polymeric carrier (e.g., micelle) provided herein.

In some embodiments, a polynucleotide (e.g., oligonucleotide) is chemically conjugated to the polymeric carrier (e.g., micelle) and/or to one or more polymer of the polymeric carrier (e.g., micelle) by any suitable chemical conjugation technique. In some embodiments, polymeric carriers (e.g., micelles) containing an RNAi agent are formed by conjugation of the RNAi agent with an already formed polymeric carrier (e.g., micelle) comprising a plurality of polymers (e.g., block copolymers). In other embodiments, polymeric carriers (e.g., micelles) containing an RNAi agent are formed by conjugation of the RNAi agent with a polymer (e.g., a block copolymer) and subsequently forming the polymeric carrier (e.g., micelle) in any suitable manner, e.g., by self assembly of the resulting conjugates into a polymeric carrier (e.g., micelle) comprising the RNAi agent. In various embodiments, such a polymeric carrier optionally further comprises unconjugated polymers (e.g., block copolymers) that are similar, identical, or different than those conjugated to the RNAi agent. The covalent bond between a polymer and a polynucleotide of a polymeric carrier described herein is, optionally, non-cleavable, or cleavable. In certain embodiments, a precursor of one or more RNAi agent (e.g. a dicer substrate) is attached to the polymeric carrier (e.g., micelle) or to the polymeric units of polymeric carrier (e.g., the micelle by a non-cleavable bond). In some embodiments, one or more RNAi agent is attached through a cleavable bond. In certain embodiments, the cleavable bonds utilized in the polymeric carriers described herein include, by way of non-limiting example, disulfide bonds (e.g., disulfide bonds that dissociate in the reducing environment of the cytoplasm). In some embodiments, covalent association between a polymeric carrier (including the components thereof) and a polynucleotide (e.g., an oligonucleotide or siRNA) is achieved through any suitable chemical conjugation method, including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, conjugation is also performed with pH-sensitive bonds and linkers, including, but not limited to, hydrazone and acetal linkages. Any other suitable conjugation method is optionally utilized as well, for example a large variety of conjugation chemistries are available (see, for example, *Bioconjugation*, Aslam and Dent, Eds, Macmillan, 1998 and chapters therein).

In certain embodiments, a conjugate of one or more polynucleotide (e.g., oligonucleotide) with a polymer (e.g., block copolymer), wherein the polymer is a unimer or present in an assembled polymeric carrier, provided herein is prepared according to a process comprising the following two steps: (1) activating a modifiable end group (for example, 5'- or 3'-hydroxyl or) of an oligonucleotide using any suitable activation reagents, such as but not limited to 1-ethyl-3,3-dimethylaminopropyl carbodiimide (EDAC), imidazole, N-hydrosuccinimide (NHS) and dicyclohexylcarbodiimide (DCC), HOBt (1-hydroxybenzotriazole), p-nitrophenylchloroformate, carbonyldiimidazole (CDI), and N,N'-disuccinimidyl carbonate (DSC); and (2) covalently linking a block copolymer to the end of the oligonucleotide. In some embodiments, the 5'- or 3'-end modifiable group of an oligonucleotide is substituted by other functional groups prior to conjugation with the block copolymer. For example, hydroxyl group (—OH) is optionally substituted with a linker carrying sulfhydryl group (—SH), carboxyl group (—COOH), or amine group (—NH$_2$).

In yet another embodiment, an oligonucleotide comprising a functional group introduced into one or more of the bases (for example, a 5-aminoalkylpyrimidine), is conjugated to a polymer (e.g., block copolymer), wherein the polymer is a unimer or present in an assembled polymeric carrier, provided herein using a an activating agent or a reactive bifunctional linker according to any suitable procedure. A variety of such activating agents and bifunctional linkers is available commercially from such suppliers as Sigma, Pierce, Invitrogen and others.

In some embodiments, the polymeric carrier (e.g., micelle) comprising an oligonucleotide or a plurality of oligonucleotides is formed by a spontaneous self assembly. Spontaneous self assembly of the polymeric carrier is achieved, in some embodiments, in a single pot. For example, in some embodiments, a polymeric carrier (e.g., a micelle) self-assembled by diluting a solution of a polymer (e.g., block copolymer) described herein in an organic solvent (e.g., ethanol) with an aqueous media (e.g., water or PBS) is combined with one or more polynucleotide (e.g., oligonucleotide or siRNA), the polymeric carrier comprising the polymers and one or more polynucleotide spontaneously forming thereby. In other embodiments, spontaneous self assembly occurs by (1) contacting one or more polynucleotide (e.g., oligonucleotide or siRNA) of interest with a polymer (e.g., block copolymer or monoblock polymer) described herein so as to form a polymer-polynucleotide conjugate; and (2) subjecting the polymer-polynucleotide conjugates to conditions suitable to afford self assembly of the polymer-polynucleotide conjugates into a polymeric carrier described herein Polymer Structure In specific embodiments, the polymeric carrier provided herein comprises block copolymers, e.g., copolymers having distinct blocks and gradient copolymers. In certain embodiments, gradient copolymers are those having a hydrophilic segment (which is to be understood as a species of a hydrophilic block of a block copolymer described herein) and a hydrophobic segment (which is to be understood as a species of a hydrophobic block of a block copolymer described herein). In certain embodiments, the hydrophilic segment is a hydrophilic block and the hydrophobic segment is a hydrophobic block. In some embodiments, these polymers are non-peptidic. In other embodiments, the hydrophilic segment and the hydrophobic segment are different regions of a monoblock gradient copolymer. In various instances, a "polymeric segment" is a polymer section with a given physical property (e.g., a physical property of a block described herein, e.g., hydrophobicity, hydrophilicity, chargeability, etc.) or which comprises one or more blocks with similar physical properties (e.g., hydrophobicity, hydrophilicity, chargeability, etc.).

In certain embodiments, block copolymers of a polymeric carrier described herein each have (1) a hydrophilic block (e.g., a shell block) forming the shell of the polymeric carrier (e.g., micelle); and (2) a substantially hydrophobic block (e.g., a core block) forming the hydrophobic core of the polymeric carrier (e.g., micelle) which is stabilized through hydrophobic interactions of the core-forming polymeric segments.

In certain embodiments, block copolymers of a polymeric carrier described herein each have (1) a neutral or non-charged (e.g., substantially non-charged) hydrophilic block (e.g., a shell block) forming the shell of the polymeric carrier (e.g., micelle); and (2) a substantially hydrophobic block (e.g., a core block) forming the hydrophobic core of the polymeric carrier (e.g., micelle) which is stabilized through hydrophobic interactions of the core-forming polymeric segments. In certain embodiments, the neutral or non-charged hydrophilic block comprises a monomeric unit of neutral monomeric residues such as HPMA.

In certain embodiments, block copolymers of a polymeric carrier described herein each have (1) a cationic or polycationic charged hydrophilic block (e.g., a shell block) forming the shell of the polymeric carrier (e.g., micelle); and (2) a substantially hydrophobic block (e.g., a core block) forming the hydrophobic core of the polymeric carrier (e.g., micelle) which is stabilized through hydrophobic interactions of the core-forming polymeric segments. In certain embodiments, the hydrophilic block comprises a monomeric unit of cationic residues such as DMAEMA. In some embodiments, the hydrophilic block further comprises a species that shields, at least in part, the charge of the hydrophilic block. Such shielding includes steric-based shielding.

In certain embodiments, block copolymers of a polymeric carrier described herein each have (1) an anionic or polyanionic charged hydrophilic block (e.g., a shell block) forming the shell of the polymeric carrier (e.g., micelle); and (2) a substantially hydrophobic block (e.g., a core block) forming the hydrophobic core of the polymeric carrier (e.g., micelle) which is stabilized through hydrophobic interactions of the core-forming polymeric segments. In certain embodiments, the anionic or polyanionic charged hydrophilic block comprises a monomeric unit with anionic residues such as acrylic acid or hydrolyzed maleic anhydride.

In certain embodiments, block copolymers of a polymeric carrier described herein each have (1) an zwitterionic or polyzwitterionic charged hydrophilic block (e.g., a shell block) forming the shell of the polymeric carrier (e.g., micelle); and (2) a substantially hydrophobic block (e.g., a core block) forming the hydrophobic core of the polymeric carrier (e.g., micelle) which is stabilized through hydrophobic interactions of the core-forming polymeric segments.

In specific embodiments, the nature of the hydrophilic block (e.g., cationic, anionic, neutral, or zwitterionic) is substantially identical at acidic pH (e.g., at an endosomal pH) as it is at about neutral pH. As a result, upon uptake of the polymeric carrier into an endosome, the hydrophilic block is in substantially identical form as it was prior to uptake by the endosome.

In some cases, the hydrophilic segment may serve at least two functions: one is to form the shell of the micelle structure, and second is to bind one or more polynucleotide (e.g., oligonucleotide-based therapeutic molecules such as siRNA or oligonucleotide-based diagnostic agents such as siRNA labeled with a detectable agent, such as radiolabel, mass label, fluorophore, PET label, chromophore, or the like). In some embodiments, block copolymers also comprise chargeable or charged species (e.g., anionic and/or cationic species/monomeric units at a physiological pH) and are membrane-destabilizing (e.g., membrane destabilizing in a pH dependent manner). In some embodiments, the substantially hydrophobic block (e.g., core block) and/or the core of the polymeric carrier is substantially net neutral (i.e., taken as a whole, the positive and negative charges are substantially balanced). In some embodiments, the substantially hydrophobic block (e.g., core block) and/or the core of the polymeric carrier comprises one or more chargeable species (e.g., monomeric unit, moiety, group, or the like). In more specific embodiments, the substantially hydrophobic block and/or core of the polymeric carrier comprise a plurality of cationic species and a plurality of anionic species. In still more specific embodiments, the substantially hydrophobic block and/or core of the polymeric carrier comprises a substantially similar number of cationic and anionic species (i.e., the hydrophobic block and/or core are substantially net neutral).

In certain embodiments, a polymeric carrier provided herein comprises a hydrophobic block comprising a first and a second chargeable species. In some embodiments, the first chargeable species is as described herein and the second chargeable species is a cationic species upon protonation. In specific embodiments, the first chargeable species is non-charged at an acidic pH (e.g., an endosomal pH, a pH below about 6.5, a pH below about 6.0, a pH below about 5.8, a pH below about 5.7, or the like). In specific embodiments, the pKa of the second chargeable species is about 6 to about 10, about 6.5 to about 9, about 6.5 to about 8, about 6.5 to about 7.5, or any other suitable pKa. In certain embodiments, at least one of the first chargeable species and at least one of the second chargeable species are present on a single monomeric unit. In some embodiments, the first chargeable species is found on a first chargeable monomeric unit and the second chargeable species is on a second chargeable monomeric unit. In certain embodiments, the first chargeable species is an anionic species upon deprotonation, the second chargeable species is a cationic species upon protonation, and the ratio of the anionic species to the cationic species is between about 1:10 and about 10:1, about 1:6 and about 6:1, about 1:4 and about 4:1, about 1:2 and about 2:1, about 1:2 and 3:2, or about 1:1 at about a neutral pH. In some embodiments, the ratio of the first chargeable monomeric unit to the second chargeable monomeric unit is about 1:10 and about 10:1, about 1:6 and about 6:1, about 1:4 and about 4:1, about 1:2 and about 2:1, about 1:2 and 3:2, or about 1:1.

The term "copolymer", as used herein, signifies that the polymer is the result of polymerization of two or more different monomers.

A "monoblock polymer" is a synthetic product of a single polymerization step. The term monoblock polymer includes a copolymer (i.e. a product of polymerization of more than one type of monomers) and a homopolymer (i.e. a product of polymerization of a single type of monomers).

A "block" copolymer refers to a structure comprising one or more sub-combination of constitutional or monomeric units. In some embodiments, constitutional units are derived via additional processes from one or more polymerizable monomers. In some embodiments, a block copolymer described herein comprises non-lipidic constitutional or monomeric units. In some embodiments, the block copolymer is a diblock copolymer. A diblock copolymer comprises two blocks; a schematic generalization of such a polymer is represented by the following: $[A_aB_bC_c\ldots]_m\text{-}[X_xY_yZ_z\ldots]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. As suggested by the schematic, in some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . . An exemplary alternating random configuration may have the form: x-y-x-z-y-x-y-z-y-x-z . . . , and an exemplary regular alternating configuration may have the form: x-y-z-x-y-z-x-y-z . . . . An exemplary regular block configuration may have the following general configuration: . . . x-x-x-y-y-z-z-z-x-x-x . . . , while an exemplary random block configuration may have the general configuration: . . . x-x-x-z-z-x-x-y-y-y-z-z-z-x-x-z-z-z- . . . . In a gradient polymer, the content of one or more monomeric units increases or decreases in a gradient manner from the α end of the polymer to the ω end. In none of the preceding generic examples is the particular juxtaposition of individual constitutional units or blocks or the number of constitutional units in a block or the number of blocks meant nor should they be construed as in any manner bearing on or limiting the actual structure of block copolymers forming the polymeric carrier of this invention.

As used herein, the brackets enclosing the constitutional units are not meant and are not to be construed to mean that the constitutional units themselves form blocks. That is, the constitutional units within the square brackets may combine in any manner with the other constitutional units within the block, i.e., purely random, alternating random, regular alternating, regular block or random block configurations. The block copolymers described herein are, optionally, alternate, gradient or random block copolymers. In some embodiments, the block copolymers are dendrimer, star or graft copolymers.

In certain embodiments, the block copolymers comprise ethylenically unsaturated monomers. The term "ethylenically unsaturated monomer" is defined herein as a compound having at least one carbon double or triple bond. The non-limiting examples of the ethylenically unsaturated monomers are: an alkyl (alkyl)acrylate, a methacrylate, an acrylate, an alkylacrylamide, a methacrylamide, an acrylamide, a styrene, an allylamine, an allylammonium, a diallylamine, a diallylammonium, an N-vinyl formamide, a vinyl ether, a vinyl sulfonate, an acrylic acid, a sulfobetaine, a carboxybetaine, a phosphobetaine, or maleic anhydride.

In various embodiments, any monomer suitable for providing the polymers and/or polymeric carriers described herein is used. In some embodiments, monomers suitable for use in the preparation of polymers and polymeric carriers provided herein include, by way of non-limiting example, one or more of the following monomers: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, oligoethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, N-isopropylacryamide, vinylnaphthalene, vinyl pyridine, ethylvinylbenzene, aminostyrene, vinylimidazole, vinylpyridine, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these monomers are optionally used. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994)

Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiators is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) ("Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001).)

In certain embodiments, Reversible Addition-Fragmentation chain Transfer or RAFT is used in synthesizing ethylenic backbone polymers of this invention. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In most instances, this cycle of addition to the C=S bond followed by fragmentation of the ensuing radical continues until all monomer has been consumed or the reaction is quenched. Generally, the low concentration of active radicals at any particular time limits normal termination reactions.

In some embodiments, block copolymers utilized in the polymeric carriers (e.g., micelles) provided herein have a low polydispersity index (PDI) or differences in chain length. Polydispersity index (PDI) can be determined in any suitable manner, e.g., by dividing the weight average molecular weight of the polymer chains by their number average molecular weight. The number average molecule weight is sum of individual chain molecular weights divided by the number of chains. The weight average molecular weight is proportional to the square of the molecular weight divided by the number of molecules of that molecular weight. Since the weight average molecular weight is always greater than the number average molecular weight, polydispersity is always greater than or equal to one. As the numbers come closer and closer to being the same, i.e., as the polydispersity approaches a value of one, the polymer becomes closer to being monodisperse in which every chain has exactly the same number of constitutional units. Polydispersity values approaching one are achievable using radical living polymerization. Methods of determining polydispersity, such as, but not limited to, size exclusion chromatography, dynamic light scattering, matrix-assisted laser desorption/ionization chromatography and electrospray mass chromatography are well known in the art. In some embodiments, block copolymers of the polymeric carriers (e.g., micelles) provided herein have a polydispersity index (PDI) of less than 2.0, or less than 1.5, or less than 1.4, or less than 1.3, or less than 1.2

Polymerization processes described herein optionally occur in any suitable solvent or mixture thereof. Suitable solvents include water, alcohol (e.g., methanol, ethanol, n-propanol, isopropanol, butanol), tetrahydrofuran (THF) dimethyl sulfoxide (DMSO), dimethylformamide (DMF), acetone, acetonitrile, hexamethylphosphoramide, acetic acid, formic acid, hexane, cyclohexane, benzene, toluene, dioxane, methylene chloride, ether (e.g., diethyl ether), chloroform, and ethyl acetate. In one aspect, the solvent includes water, and mixtures of water and water-miscible organic solvents such as DMF.

In certain embodiments, poly(DMAEMA) and other polymeric entities used herein (e.g., copolymers or copolymer blocks of BMA, DMAEMA and PAA) are prepared in any suitable manner. In one embodiment, poly(DMAEMA) is prepared by polymerizing DMAEMA in the presence of the RAFT CTA, ECT, and a radical initiator. In some embodiments, a block, poly(DMAEMA) macroCTA is used to prepare a series of diblock copolymers where the second block contained BMA, DMAEMA and PAA. In other specific embodiments, the orientation of the blocks on the diblock polymer is reversed, such that upon self-assembly, the ω end of the polymer is exposed on the hydrophilic segment of the micelle or polymeric carrier. In various embodiments, this is achieved in any suitable manner, including a number of ways synthetically. For example, in some embodiments, the synthesis of the block copolymers described herein begins with the preparation of the PAA/BMA/DMAEMA core-forming hydrophobic block, and the shell-forming hydrophilic, charged block is added in the second synthetic step by subjecting the resulting PAA/BMA/DMAEMA macroCTA to a second RAFT polymerization step. Alternate approaches include reducing the PAA/BMA/DMAEMA macroCTA to form a thiol end and then covalently attaching a pre-formed hydrophilic, charged polymer to the formed thiol. This synthetic approach provides a method for introduction of a reactive group on the w-end of the polymeric chain exposed to the surface of micelle thus providing alternate approaches to chemical conjugation to the micelle.

In some embodiments, block copolymers are synthesized by chemical conjugation of several polymer blocks that are prepared by separate polymerization processes.

Charged Species and Hydrophobic Core

In certain embodiments, the hydrophobic block further comprises one or more types of chargeable species. In specific embodiments, the chargeable species is chargeable to a cationic species. The polymeric carriers described herein, comprising chargeable species include polymeric carriers wherein each of chargeable species are, each individually present in the polymeric carrier in a charged state or a non-charged state. Furthermore, wherein the polymeric carriers described herein comprise a population of a first chargeable species, a population of second chargeable species and/or a population of any additional chargeable species, the polymeric carriers described herein include polymeric carriers wherein each of the population of first, second, and any additional chargeable species are, each individually, present in the polymeric carrier in a completely charged state, a partially charged state or a completely non-charged state.

In some embodiments, the anionic chargeable species is any organic or inorganic acid residue that is optionally present, either as a protected species, e.g., an ester, or as the free acid, in the selected polymerization process. In some embodiments, the anionic chargeable species is a weak acid, such as but not limited to the following groups: boronic acid, sulfonamide, phosphonic acid, arsonic acid, phosphinic acid, phosphate, carboxylic acid, xanthenes, tetrazole or their derivatives (e.g. esters). In certain embodiments monomers such as maleic-anhydride, (Scott M. Henry, Mohamed E. H. El-Sayed, Christopher M. Pirie, Allan S. Hoffman, and Patrick S. Stayton pH-Responsive Poly(styrene-alt-maleic anhydride) Alkylamide Copolymers for Intracellular Drug Delivery. *Biomacromolecules* 2006, 7, 2407-2414) are used for introduction of first chargeable species by post-polymerization hydrolysis of the maleic anhydride monomeric units. In specific embodiments, a chargeable species that are anionic at normal physiological pH are carboxylic acids such as, but not limited to, 2-propyl acrylic acid or, more accurately, the constitutional unit derived from it, 2-propylpropionic acid, —$CH_2C((CH_2)_2CH_3)(COOH)$ (PAA).

In some embodiments, the chargeable species is cationic. In certain embodiments, the chargeable species is cationic at physiological pH. In specific embodiments, cationic at physiological pH species are nitrogen species such as ammonium, —$NRR'R''$, guanidinium (—$NRC(=NR'H)^+NR''R'''$, including canonical forms that are known to those skilled in the art) wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, or indole. In some embodiments, the combination of two mechanisms of membrane disruption, (a) a polycation (such as DMAEMA) and (b) a hydrophobized polyanion (such as propylacrylic acid), acting together have an additive or synergistic effect on the potency of the membrane destabilization conferred by the polymer.

In some embodiments, the block copolymers comprise a plurality of hydrophobic species. In some embodiments, the block copolymer comprises hydrophobic monomeric units. In certain embodiments, the hydrophobic monomeric unit is a vinyl substituted aromatic or heteroaromatic compound. In further specific embodiments, hydrophobic monomers are alkyl (alkyl)acrylates. In specific embodiments, the hydrophobic monomer is a styrene derivative.

In some embodiments, the polymer comprises zwitterionic monomeric units wherein an anionic and a cationic chargeable species are present in the same monomeric unit.

In some instances, the block copolymers comprise monomers bearing reactive groups which can be used for post-polymerization introduction of additional functionalities via know in the art chemistries, for example, "click" chemistry (for example of "click" reactions, see Wu, P.; Fokin, V. V., Catalytic Azide-Alkyne Cycloaddition: Reactivity and Applications. *Aldrichim. Acta,* 2007, 40, 7-17). In certain embodiments, reactive group is an activated group, including, but not limited to, N-hydrosuccinimide (NHS) ester, HOBt (1-hydroxybenzotriazole) ester, p-nitrophenyl ester, tetrafluorophenyl ester, pentafluorophenyl ester, pyridyl disulfide group or the like.

In specific instances, provided herein are the polymers of the following structure:

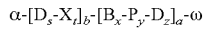  [Structure 1]

  [Structure 2]

wherein x, y, z, s and t are the mole % composition (generally, 0-50%) of the individual monomeric units D (DMAEMA), B (BMA), P (PAA), and a hydrophilic neutral monomer (X) in the polymer block, a and b are the molecular weights of the blocks, $[D_s-X_t]$ is the hydrophilic block, and α and ω denote the opposite ends of the polymer. In certain embodiments, x is 50%, y is 25% and z is 25%. In certain embodiments, x is 60%, y is 20% and z is 20%. In certain embodiments, x is 70%, y is 15% and z is 15%. In certain embodiments, x is 50%, y is 25% and z is 25%. In certain embodiments, x is 33%, y is 33% and z is 33%. In certain embodiments, x is 50%, y is 20% and z is 30%. In certain embodiments, x is 20%, y is 40% and z is 40%. In certain embodiments, x is 30%, y is 40% and z is 30%. In some embodiments, a polymeric carrier described herein comprises a hydrophilic block of about 2,000 Da to about 30,000 Da, about 5,000 Da to about 20,000 Da, or about 7,000 Da to about 15,000 Da. In specific embodiments, the hydrophilic block is of about 7,000 Da, 8,000 Da, 9,000 Da, 10,000 Da, 11,000 Da, 12,000 Da, 13,000 Da, 14,000 Da, or 15,000 Da. In certain embodiments, a polymeric carrier described herein comprises a hydrophobic block of about 2,000 Da to about 50,000 Da, 10,000 Da to about 50,000 Da, about 15,000 Da to about 35,000 Da, or about 20,000 Da to about 30,000 Da. In some specific embodiments, the polymer with a hydrophilic block is of 12,500 Da and a hydrophobic block of 25,000 Da (length ratio of 1:2) forms polymeric carriers (e.g., micelles). In some specific embodiments, the polymer with a hydrophilic block is of 10,000 Da and a hydrophobic block of 30,000 Da (length ratio of 1:3) forms polymeric carriers (e.g., micelles). In some specific embodiments, the polymer with a hydrophilic block is of 10,000 Da and a hydrophobic block of 25,000 Da (length ratio of 1:2.5) forms polymeric carriers (e.g., micelles) of approximately 45 nm (as determined by dynamic light scattering measurements or electron microscopy). In some specific embodiments, the micelles are 80 or 130 nm (as determined by dynamic light scattering measurements or electron microscopy). Typically, as the molecular weight (or length) of $[D_s-X_t]$, which forms the micelle shell, increases relative to $-[B_x-P_y-D_z]$ the hydrophobic block that forms the core, the size of the micelle increases. In some instances, the size of the polymer cationic block that forms the shell ($[D_s-X_t]$ is important in providing effective complex formation/charge neutralization with the oligonucleotide drug. For example, in certain instances, for siRNA of approximately 20 base pairs (i.e., 40 anionic charges) a cationic block has a length suitable to provide effective binding, for example 40 cationic charges. For a shell block containing 80 DMAEMA monomers (MW=11,680) with a pKa value of 7.4, the block contains 40 cationic charges at pH 7.4. In some instances, stable polymer-siRNA conjugates (e.g., complexes) form by electrostatic interactions between similar numbered opposite charges. In certain instances, avoiding a large number of excess positive charge helps to prevent significant in vitro and in vivo toxicity.

In specific embodiments, the hydrophobic block of the block copolymer comprises a plurality a cationic chargeable species, for example, dimethylaminoethylmethacrylate (DMAEMA). Thus, in some embodiments, the structure of such a polymeric segment is represented by the Structure 3:

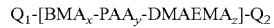  [Structure 3]

wherein x, y, and z and are the mole % composition (generally, 0-50%) of the individual monomeric units, and wherein in the above designation denote other polymer blocks or end group functionalities. In certain instances, the individual monomeric units serve individual and synergistic functions. For example, polypropyl acrylic acid, which comprises both anionic species and hydrophobic species, with a pKa value of ~6.7 is hydrophilic above a pH of about 6.7 and is increasingly hydrophobic below a pH of about 6.7, where the carboxylates become protonated. In certain instances, increasing the hydrophobicity of the local environment, for example, by increasing the mole % of the predominantly hydrophobic monomer unit BMA in the block raises the PAA pKa and results in protonation of PAA at a higher pH, that is, the PAA containing block becomes more membrane destabilizing at a higher pH and thus more responsive to smaller acidic changes in pH below physiological pH ~7.4. In some instances, protonation of PAA results in a large increase in hydrophobicity and subsequent conformational change to a form with membrane destabilizing properties. A third monomeric unit in the above described polymer block is the cationic species, for example DMAEMA, which, in some instances, serves multiple functions, including but not limited to the following. When matched in equivalent molar amounts to the anionic species of PAA, it creates charge neutralization and the potential for forming electrostatic interactions that can contribute to the stability of the hydrophobic core of a micelle structure where either $Q_1$ or $Q_2$ in the above structure is a hydrophilic homopolymer block, for example poly-DMAEMA.

Block Arrangement

In some embodiments, the polynucleotide carrier block is cationic at or near physiological pH (e.g., the pH of circulation human plasma). In some embodiments, the polynucleotide carrier block comprises a polycation. In some embodiments, the nucleic acid (e.g., siRNA) is polyanionic comprising x anions, and the polynucleotide carrier block comprises about 0.6 x, about 0.7·x, about 0.8 x, about 0.9 x, about 1.0 x, about 1.1 x cations, or more. In specific embodiments, the nucleic acid (e.g., siRNA) is polyanionic comprising x anions, and the polynucleotide carrier block comprises about 0.7·x cations, or more. In certain embodiments, the cationic species of the polynucleotide carrier block are nitrogen species such as, but not limited to ammonium, —NRR'R'', guanidinium (—NRC(=NR'H)⁺NR''R''', including canonical forms that are known to those skilled in the art) wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, or indole. In some embodiments, the polynucleotide carrier block is a nucleic-acid binding polyamide, an intercalator, or a duplex- or triplex-forming oligonucleotide. The polynucleotide carrier block can be either the α-end block or the ω-end block of the block copolymer. In specific embodiments, polynucleotide carrier block has a number average molecular weight (Mn) of about 10,000 dalton to about 20,000 dalton. In other embodiments, the hydrophobic block has a number average molecular weight (Mn) of about 2,000 dalton to about 50,000 dalton, or about 10,000 dalton to about 50,000 dalton.

In specific embodiments, the block copolymer (e.g., diblock copolymer) has the chemical Formula I:

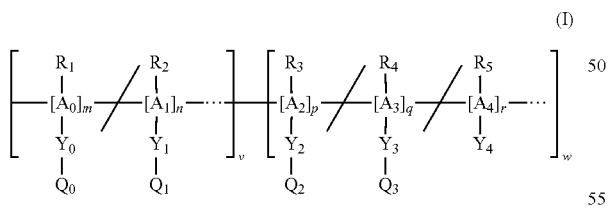
(I)

In some embodiments:

$A_0$, $A_1$, $A_2$, $A_3$ and $A_4$ are selected from the group consisting of —C—, —C—C—, —C(O)(C)$_a$C(O)O—, —O(C)$_a$C(O)— and —O(C)$_b$O—; wherein,
a is 1-4;
b is 2-4;

$Y_4$ is selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C), (4C-10C)hetroaryl (6C-10C)aryl, any of which is optionally substituted with one or more fluorine groups;

$Y_0$, $Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-, —C(O)NR$_6$(2C-10C) alkyl-; (4C-10C)hetroaryl and (6C-10C)aryl;

$Y_3$ is selected from the group consisting of a covalent bond, (1C-10C)alkyl, (4C-10C)hetroaryl and (6C-10C)aryl; wherein
tetravalent carbon atoms of $A_1$-$A_4$ that are not fully substituted with $R_1$-$R_5$ and
$Y_1$-$Y_4$ are completed with an appropriate number of hydrogen atoms;

$R_1$, $R_2$, $R_3$, $R_4$, $R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_0$ is a residue selected from the group consisting of residues which are hydrophilic at physiologic pH, and are at least partially positively charged at physiologic pH (e.g., amino, alkylamino, ammonium, alkylammonium, guanidine, imidazolyl, pyridyl, or the like); at least partially negatively charged at physiologic pH but undergo protonation at lower pH (e.g., carboxyl, sulfonamide, boronate, phosphonate, phosphate, or the like); substantially neutral (or non-charged) at physiologic pH (e.g., hydroxy, polyoxylated alkyl, polyethylene glycol, polypropylene glycol, thiol, or the like); at least partially zwitterionic at physiologic pH (e.g., a monomeric residue comprising a phosphate group and an ammonium group at physiologic pH); conjugatable or functionalizable residues (e.g. residues that comprise a reactive group, e.g., azide, alkyne, succinimide ester, tetrafluorophenyl ester, pentafluorophenyl ester, p-nitrophenyl ester, pyridyl disulfide, or the like); or hydrogen;

$Q_1$ is a residue which is hydrophilic at physiologic pH, and is at least partially positively charged at physiologic pH (e.g., amino, alkylamino, ammonium, alkylammonium, guanidine, imidazolyl, pyridyl, or the like); at least partially negatively charged at physiologic pH but undergoes protonation at lower pH (e.g., carboxyl, sulfonamide, boronate, phosphonate, phosphate, or the like); substantially neutral at physiologic pH (e.g., hydroxy, polyoxylated alkyl, polyethylene glycol, polypropylene glycol, thiol, or the like); or at least partially zwitterionic at physiologic pH (e.g., comprising a phosphate group and an ammonium group at physiologic pH);

$Q_2$ is a residue which is positively charged at physiologic pH, including but not limited to amino, alkylamino, ammonium, alkylammonium, guanidine, imidazolyl, and pyridyl;

$Q_3$ is a residue which is negatively charged at physiologic pH, but undergoes protonation at lower pH, including but not limited to carboxyl, sulfonamide, boronate, phosphonate, and phosphate;

m is about 0 to less than 1.0 (e.g., 0 to about 0.49);
n is greater than 0 to about 1.0 (e.g., about 0.51 to about 1.0); wherein $$m+n=1$$

p is about 0.1 to about 0.9 (e.g., about 0.2 to about 0.5);
q is about 0.1 to about 0.9 (e.g., about 0.2 to about 0.5); wherein:
r is 0 to about 0.8 (e.g., 0 to about 0.6); wherein $$p+q+r=1$$

v is from about 1 to about 25 kDa, or about 5 to about 25 kDa; and, w is from about 1 to about 50 kDa, or about 5 to about 50 kDa.

In some embodiments, the number or ratio of monomeric residues represented by p and q are within about 30% of each other, about 20% of each other, about 10% of each other, or the like. In specific embodiments, p is substantially the same as q. In certain embodiments, at least partially charged generally includes more than a trace amount of charged species, including, e.g., at least 20% of the residues are charged, at least 30% of the residues are charged, at least 40% of the residues are charged, at least 50% of the residues are charged, at least 60% of the residues are charged, at least 70% of the residues are charged, or the like.

In certain embodiments, m is 0 and $Q_1$ is a residue which is hydrophilic and substantially neutral (or non-charged) at physiologic pH. In some embodiments, substantially non-charged includes, e.g., less than 5% are charged, less than 3% are charged, less than 1% are charged, or the like. In certain embodiments, m is 0 and $Q_1$ is a residue which is hydrophilic and at least partially cationic at physiologic pH. In certain embodiments, m is 0 and $Q_1$ is a residue which is hydrophilic and at least partially anionic at physiologic pH. In certain embodiments, m is >0 and n is >0 and one of and $Q_0$ or $Q_1$ is a residue which is hydrophilic and at least partially cationic at physiologic pH and the other of $Q_0$ or $Q_1$ is a residue which is hydrophilic and is substantially neutral at physiologic pH. In certain embodiments, m is >0 and n is >0 and one of and $Q_0$ or $Q_1$ is a residue which is hydrophilic and at least partially anionic at physiologic pH and the other of $Q_0$ or $Q_1$ is a residue which is hydrophilic and is substantially neutral at physiologic pH. In certain embodiments, m is >0 and n is >0 and $Q_1$ is a residue which is hydrophilic and at least partially cationic at physiologic pH and $Q_0$ is a residue which is a conjugatable or functionalizable residue. In certain embodiments, m is >0 and n is >0 and $Q_1$ is a residue which is hydrophilic and substantially neutral at physiologic pH and $Q_0$ is a residue which is a conjugatable or functionalizable residue.

In certain embodiments, a polymeric carrier described herein comprises a block copolymer of Formula II:

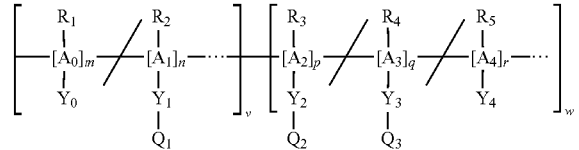

(II)

In some embodiments:

$A_0, A_1, A_2, A_3$ and $A_4$ are selected from the group consisting of —C—C—, —C(O)(C)$_a$C(O)O—, —O(C)$_a$C(O)— and —O(C)$_b$O—; wherein, a is 1-4;

b is 2-4;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl, C(O)NR$_6$(1C-10C)alkyl, (4C-10C)hetroaryl and (6C-10C)aryl, any of which is optionally substituted with one or more fluorine groups;

$Y_1$ and $Y_2$ are independently selected from the group consisting of a covalent bond, (1C-10C)alkyl-, —C(O)O (2C-10C) alkyl-, —OC(O)(1C-10C) alkyl-, —O(2C-10C)alkyl- and —S(2C-10C)alkyl- , —C(O)NR$_6$(2C-10C) alkyl, (4C-10C)hetroaryl and (6C-10C)aryl;

$Y_3$ is selected from the group consisting of a covalent bond, (1C-10C)alkyl, (4C-10C)hetroaryl and (6C-10C)aryl; wherein tetravalent carbon atoms of $A_1$-$A_4$ that are not fully substituted with $R_1$-$R_5$ and $Y_0$-$Y_4$ are completed with an appropriate number of hydrogen atoms;

$R_1, R_2, R_3, R_4, R_5$, and $R_6$ are independently selected from the group consisting of hydrogen, —CN, alkyl, alkynyl, heteroalkyl, cycloalkyl, heterocycloalkyl, aryl and heteroaryl, any of which may be optionally substituted with one or more fluorine atoms;

$Q_1$ and $Q_2$ are residues which are positively charged at physiologic pH, including but not limited to amino, alkylamino, ammonium, alkylammonium, guanidine, imidazolyl, and pyridyl.

$Q_3$ is a residue which is negatively charged at physiologic pH, but undergoes protonation at lower pH, including but not limited to carboxyl, sulfonamide, boronate, phosphonate, and phosphate.

m is 0 to about 0.49;

n is about 0.51 to about 1.0; wherein $m+n=1$ p is about 0.2 to about 0.5;

q is about 0.2 to about 0.5; wherein:

p is substantially the same as q;

r is 0 to about 0.6; wherein $p+q+r=1$ v is from about 5 to about 25 kDa; and, w is from about 5 to about 50 kDa.

In certain embodiments, a polymeric carrier described herein comprises a block copolymer (e.g., at normal physiological pH) of Formula III:

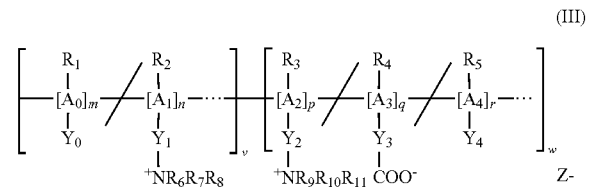

(III)

In certain embodiments, $A_0, A_1, A_2, A_3$, and $A_4$, substituted as indicated comprise the constitutional units (used interchangeably herein with "monomeric units" and "monomeric residues") of the polymer of Formula III. In specific embodiments, the monomeric units of constituting the A groups of Formula III are polymerizably compatible under appropriate conditions. In certain instances, an ethylenic backbone or constitutional unit, —(C—C—)$_m$— polymer, wherein each C is di-substituted with H and/or any other suitable group, is polymerized using monomers containing a carbon-carbon double bond, >C=C<. In certain embodiments, each A group (e.g., each of $A_0, A_1, A_2, A_3$, and $A_4$) may be (i.e., independently selected from) —C—C— (i.e., an ethylenic monomeric unit or polymer backbone), —C(O)(C)$_a$C(O)O— (i.e., a polyanhydride monomeric unit or polymer backbone), —O(C)$_a$C(O)— (i.e., a polyester monomeric unit or polymer backbone), —O(C)$_b$O— (i.e., a polyalkylene glycol monomeric unit or polymer backbone), or the like (wherein each C is di-substituted with H and/or any other suitable group such as described herein, including $R_{12}$ and/or $R_{13}$ as described above). In specific embodiments, the term "a" is an integer from 1 to 4, and "b" is an integer from 2 to 4. In certain instances, each "Y" and "R" group attached to the backbone of Formula III (i.e., any one of $Y_0$, $Y_1$, $Y_2$, $Y_3$, $Y_4$, $R_1$, $R_2$, $R_3$, $R_4$, $R_5$) is bonded to any "C" (including any $(C)_a$ or $(C)_b$) of the specific monomeric unit. In specific embodiments, both the Y and R of a specific monomeric unit is attached to the same "C". In certain specific embodiments, both the Y and R of a specific monomeric unit is attached to the same "C", the "C" being alpha to the carbonyl group of the monomeric unit, if present.

In specific embodiments, $R_1$-$R_{11}$ are independently selected from hydrogen, alkyl (e.g., 1C-5C alkyl), cycloalkyl (e.g., 3C-6C cycloalkyl), or phenyl, wherein any of $R_1$-$R_{11}$ is optionally substituted with one or more fluorine, cycloalkyl, or phenyl, which may optionally be further substituted with one or more alkyl group.

In certain specific embodiments, $Y_0$ and $Y_4$ are independently selected from hydrogen, alkyl (e.g., 1C-10C alkyl), cycloalkyl (e.g., 3C-6C cycloalkyl), O-alkyl (e.g., O-(2C-10C)alkyl, —C(O)O-alkyl (e.g., —C(O)O-(2C-10C)alkyl), or phenyl, any of which is optionally substituted with one or more fluorine.

In some embodiments, $Y_1$ and $Y_2$ are independently selected from a covalent bond, alkyl, preferably at present a (1C-10C)alkyl, —C(O)O-alkyl, preferably at present —C(O)O-(2C-10C)alkyl, —OC(O)alkyl, preferably at present —OC(O)-(2C-10C)alkyl, O-alkyl, preferably at present —O(2C-10C)alkyl and —S-alkyl, preferably at present —S-(2C-10C)alkyl. In certain embodiments, $Y_3$ is selected from a covalent bond, alkyl, preferably at present (1C-5C)alkyl and phenyl.

In some embodiments, Z— is present or absent. In certain embodiments, wherein $R_1$ and/or $R_4$ is hydrogen, Z— is OH—. In certain embodiments, $Z^-$ is any counterion (e.g., one or more counterion), preferably a biocompatible counter ion, such as, by way of non-limiting example, chloride, inorganic or organic phosphate, sulfate, sulfonate, acetate, propionate, butyrate, valerate, caproate, caprylate, caprate, laurate, myristate, palmate, stearate, palmitolate, oleate, linolate, arachidate, gadoleate, vaccinate, lactate, glycolate, salicylate, desaminophenylalanine, desaminoserine, desaminothreonine, ε-hydroxycaproate, 3-hydroxybutylrate, 4-hydroxybutyrate or 3-hydroxyvalerate. In some embodiments, when each Y, R and optional fluorine is covalently bonded to a carbon of the selected backbone, any carbons that are not fully substituted are completed with the appropriate number of hydrogen atoms. The numbers m, n, p, q and r represent the mole fraction of each constitutional unit in its block and v and w provide the molecular weight of each block.

In certain embodiments, $A_0$, $A_1$, $A_2$, $A_3$ and $A_4$ are selected from the group consisting of —C—, —C—C—, —C(O)(CR$_{12}$R$_{13}$)$_a$C(O)O—, —O(CR$_{12}$R$_{13}$)$_a$C(O)— and O(CR$_{12}$R$_{13}$)$_b$O—;
wherein,
a is 1-4;
b is 2-4;

$R_1$, $R_2$, $R_3$, $R_4$, $R_5$, $R_6$, $R_7$, $R_8$, $R_9$, $R_{10}$, $R_{11}$, $R_{12}$, and $R_{13}$ are independently selected from the group consisting of hydrogen, (1C-5C)alkyl, (3C-6C)cycloalkyl, (5C-10C)aryl, (4C-10C)heteroaryl, any of which may be optionally substituted with one or more fluorine atoms;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl;
wherein tetravalent carbon atoms of $A_1$-$A_4$ that are not fully substituted with $R_1$-$R_5$ and $Y_0$-$Y_4$ are completed with an appropriate number of hydrogen atoms;

Z is one or more physiologically acceptable counterions,
m is 0 to about 0.49;
n is about 0.51 to about 1.0; wherein $m+n=1$ p is about 0.2 to about 0.5;
q is about 0.2 to about 0.5; wherein:
p is substantially the same as q;
r is 0 to about 0.6; wherein $p+q+r=1$ v is from about 1 to about 25 kDa, or about 5 to about 25 kDa; and,
w is from about 1 to about 50 kDa, or about 5 to about 50 kDa.

In a specific embodiment, $A_0$, $A_1$, $A_2$, $A_3$ and $A_4$ are independently selected from the group consisting of —C—C—, —C(O)(C)$_a$C(O)O—, —O(C)$_a$C(O)— and —O(C)$_b$O—; wherein,
a is 1-4;
b is 2-4;

$R_1$, $R_2$, $R_3$, $R_4$, $R_5$, $R_6$, $R_7$, $R_8$, $R_9$, $R_{10}$ and $R_{11}$ are independently selected from the group consisting of hydrogen, (1C-5C)alkyl, (3C-6C)cycloalkyl and phenyl, any of which may be optionally substituted with one or more fluorine atoms;

$Y_0$ and $Y_4$ are independently selected from the group consisting of hydrogen, (1C-10C)alkyl, (3C-6C)cycloalkyl, O-(1C-10C)alkyl, —C(O)O(1C-10C)alkyl and phenyl, any of which is optionally substituted with one or more fluorine groups;

$Y_1$ and $Y_2$ are independently selected from the group consisting of a covalent bond, (1C-10C)alkyl-, —C(O)O(2C-10C) alkyl-, —OC(O)(1C-10C) alkyl-, —O(2C-10C)alkyl- and —S(2C-10C)alkyl-;

$Y_3$ is selected from the group consisting of a covalent bond, (1C-5C)alkyl and phenyl;
wherein tetravalent carbon atoms of $A_1$-$A_4$ that are not fully substituted with $R_1$-$R_5$ and $Y_0$-$Y_4$ are completed with an appropriate number of hydrogen atoms;

Z is a physiologically acceptable counterion,
m is 0 to about 0.49;
n is about 0.51 to about 1.0;
wherein m+n=1
p is about 0.2 to about 0.5;
q is about 0.2 to about 0.5; wherein:
p is substantially the same as q;
r is 0 to about 0.6; wherein $p+q+r=1$ v is from about 5 to about 25 kDa; and
w is from about 5 to about 25 kDa.

In some embodiments,
A$_1$ is —C—C—
Y$_1$ is —C(O)OCH$_2$CH$_2$—;
R$_6$ is hydrogen;
R$_7$ and R$_8$ are each —CH$_3$; and,
R$_2$ is —CH$_3$.
In some embodiments,
A$_2$ is —C—C—;
Y$_2$ is —C(O)OCH$_2$CH$_2$—;
R$_9$ is hydrogen;
R$_{10}$ and R$_{11}$ are each —CH$_3$; and,
R$_3$ is —CH$_3$.
In some embodiments,
A$_3$ is —C—C—;
R$_4$ is CH$_3$CH$_2$CH$_2$—;
Y$_3$ is a covalent bond;
and Z$^-$ is a physiologically acceptable anion.
In some embodiments,
A$_4$ is —C—C—;
R$_5$ is selected from the group consisting of hydrogen and —CH$_3$; and,
Y$_4$ is —C(O)O(CH$_2$)$_3$CH$_3$.
In some embodiments,
A$_0$ is C—C—
R$_1$ is selected from the group consisting of hydrogen and (1C-3C)alkyl; and,
Y$_0$ is selected from the group consisting of —C(O)O(1C-3C)alkyl.
In some embodiments, m is 0.
In some embodiments, r is 0.
In some embodiments, m and r are both 0.

In various embodiments described herein, constitutional units, that are cationic or positively charged at physiological pH (including, e.g., certain hydrophilic constitutional units) described herein comprise one or more amino groups, alkylamino groups, guanidine groups, imidazolyl groups, pyridyl groups, or the like, or the protonated, alkylated or otherwise charged forms thereof. In some embodiments, constitutional units that are cationic at normal physiological pH that are utilized herein include, by way of non-limiting example, monomeric residues of dialkylaminoalkylmethacrylates (e.g., DMAEMA). In various embodiments described herein, constitutional units, that are anionic or negatively charged at physiological pH (including, e.g., certain hydrophilic constitutional units) described herein comprise one or more acid group or conjugate base thereof, including, by way of non-limiting example, carboxylate, sulfonamide, boronate, phosphonate, phosphate, or the like. In some embodiments, constitutional units that are anionic or negatively charged at normal physiological pH that are utilized herein include, by way of non-limiting example, monomeric residues of acrylic acid, alkyl acrylic acid (e.g., methyl acrylic acid, ethyl acrylic acid, propyl acrylic acid, etc.), or the like. In various embodiments described herein, hydrophilic constitutional units that are neutral at physiologic pH comprise one or more hydrophilic group, e.g., hydroxy, polyoxylated alkyl, polyethylene glycol, polypropylene glycol, thiol, or the like. In some embodiments, hydrophilic constitutional units that are neutral at normal physiological pH that are utilized herein include, by way of non-limiting example, monomeric residues of PEGylated acrylic acid, PEGylated methacrylic acid, hydroxyalkylacrylic acid, hydroxyalkylalkacrylic acid (e.g, HPMA), or the like. In various embodiments described herein, hydrophilic constitutional units that are zwitterionic at physiologic pH comprise an anionic or negatively charged group at physiologic pH and a cationic or positively charged group at physiologic pH. In some embodiments, hydrophilic constitutional units that are zwitterionic at normal physiological pH that are utilized herein include, by way of non-limiting example, monomeric residues of comprising a phosphate group and an ammonium group at physiologic pH, such as set forth in U.S. Pat. No. 7,300,990, which is hereby incorporated herein for such disclosure, or the like.

In certain embodiments, polymers provided herein further comprise one or more constitutional unit comprising a conjugatable or functionalizable side chain (e.g., a pendant group of a monomeric residue). In some instances, a conjugatable or functionalizable side chain is a group bearing one or more reactive groups that can be used for post-polymerization introduction of additional functionalities via know in the art chemistries, for example, "click" chemistry (for example of "click" reactions, see Wu, P.; Fokin, V. V. Catalytic Azide-Alkyne Cycloaddition: Reactivity and Applications. *Aldrichim. Acta,* 2007, 40, 7-17). In certain embodiments, conjugatable or functionalizable side chains provided herein comprise one or more of any suitable activated group, such as but not limited to N-hydrosuccinimide (NHS)ester, HOBt (1-hydroxybenzotriazole) ester, p-nitrophenyl ester, tetrafluorophenyl ester, pentafluorophenyl ester, pyridyl disulfide group or the like.

Provided in certain embodiments, the block copolymer is a diblock copolymer, having the chemical formula (at normal physiological or about neutral pH) of Formula 1:

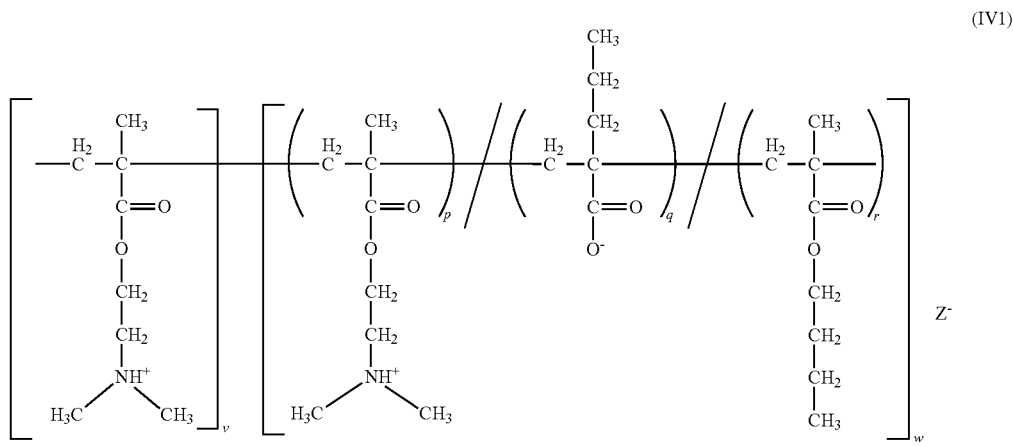

In certain instances, the constitutional units of the compound IV1 are as shown within the square bracket on the left and the curved brackets on the right and they are derived from the monomers:

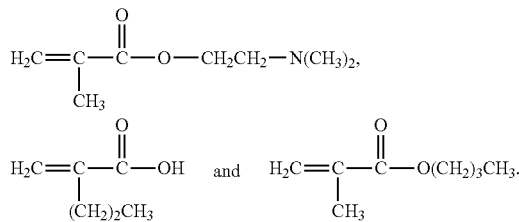

The letters p, q and r represent the mole fraction of each constitutional unit within its block. The letters v and w represent the molecular weight (number average) of each block in the diblock copolymer.

Provided in some embodiments, a compound provided herein is a compound having the structure:

units, such as illustrated in compound IV2, or 4-5 ethylene oxide units, or 7-8 ethylene oxide units); MAA(NHS) is methylacrylic acid-N-hydroxy succinamide residue; HPMA is N-(2-hydroxypropyl)methacrylamide residue; and PDSM is pyridyl disulfide methacrylate residue. In certain embodiments, the terms m, n, p, q, r, w and v are as described herein. In specific embodiments, w is about 0.1× to about 5×, or about 1× to about 5×v.

Compounds of Formulas IV1-IV9 are examples of polymers provided herein comprising a variety of constitutional unit(s) making up the first block of the polymer. In some embodiments, the constitutional unit(s) of the first block are varied or chemically treated in order to create polymers where the first block is or comprises a constitutional unit that is neutral (e.g., PEGMA), cationic (e.g., DMAEMA), anionic (e.g., PEGMA-NHS, where the NHS is hydrolyzed to the acid, or acrylic acid), ampholytic (e.g., DMAEMA-NHS, where the NHS is hydrolyzed to the acid), or zwitterionic (for example, poly[2-methacryloyloxy-2' trimethylammoniumethyl phosphate]). In some embodiments, polymers comprising pyridyl disulfide functionality in the first block, e.g.,

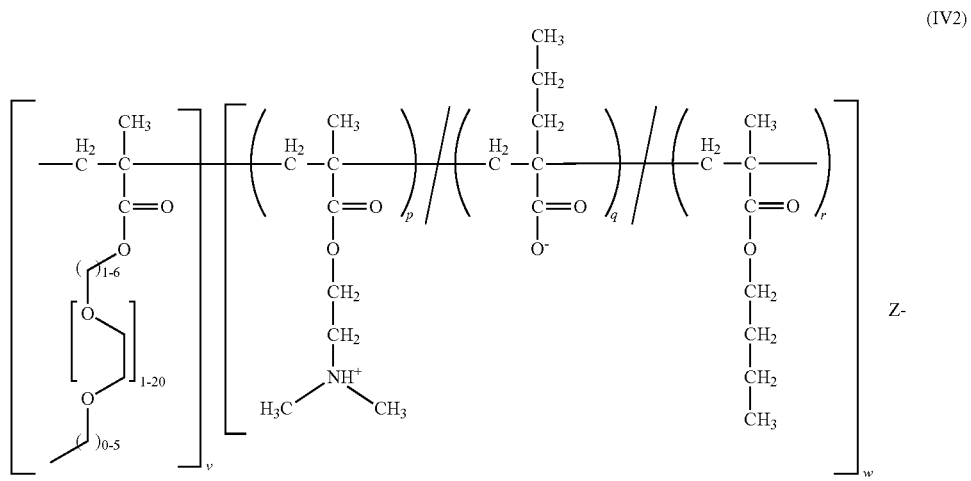

(IV2)

As discussed above, letters p, q and r represent the mole fraction of each constitutional unit within its block. The letters v and w represent the molecular weight (number average) of each block in the diblock copolymer.

In some embodiments, provided herein the following polymers:

   IV3

   IV4

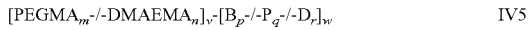   IV5

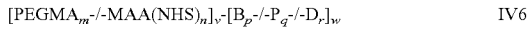   IV6

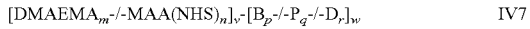   IV7

   IV8

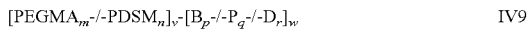   IV9

In some embodiments, B is butyl methacrylate residue; P is propyl acrylic acid residue; D and DMAEMA are dimethylaminoethyl methacrylate residue; PEGMA is polyethyleneglycol methacrylate residue (e.g., with 1-20 ethylene oxide

[PEGMA-PDSM]-[B-P-D], that can be and is optionally reacted with a thiolated siRNA to form a polymer-siRNA conjugate.

In a specific embodiment, a compound of Formula IV3 is a polymer of the P7 class, as described herein, and has the molecular weight, polydispersity, and monomer composition as set forth in Table 1.

TABLE 1

| Molecular weights, polydispersities, and monomer compositions for a species of P7 polymer | |
|---|---|
| Polymer Class | P7 |
| Mn of "v" block[a] | 9100 |
| Mn of "w" block[a] | 11300 |
| PDI | 1.45 |
| Theoretical % BMA residue of "w" block | 40 |
| Theoretical % PPA residue of "w" block | 30 |
| Theoretical % DMAEMA residue of "w" block | 30 |

TABLE 1-continued

Molecular weights, polydispersities, and monomer compositions for a species of P7 polymer

| Polymer Class | P7 |
|---|---|
| Experimental % BMA residue of "w" block[b] | 48 |
| Experimental % PPA residue of "w" block[b] | 29 |
| Experimental % DMAEMA residue of "w" block[b] | 23 |

[a]As determined by SEC Tosoh TSK-GEL R-3000 and R-4000 columns (Tosoh Bioscience, Mongomeryville, PA) connected in series to a Viscotek GPCmax VE2001 and refractometer VE3580 (Viscotek, Houston, TX). HPLC-grade DMF containing 0.1 wt % LiBr was used as the mobile phase. The molecular weights of the synthesized copolymers were determined using a series of poly(methyl methacrylate) standards.
[b]As determined by $^1$H NMR spectroscopy (3 wt % in CDCL$_3$; Bruker DRX 499)

In some specific embodiments, a polymer of Formula IV3 is a polymer of the P7 class according to Table 2.

TABLE 2

| Polymer | Structure | Block Ratio (w/v) | Particle Size (nm) |
|---|---|---|---|
| PRx-1 | $[D]_{11.3K}$-$[B_{50}$-$P_{30}$-$D_{20}]_{20.7K}$ | 1.83 | 41 |
| PRx-2 | $[D]_{14.5K}$-$[B_{57}$-$P_{23}$-$D_{20}]_{26.4K}$ | 1.82 | 49 |
| PRx-3 | $[D]_{11.5K}$-$[B_{35}$-$P_{27}$-$D_{38}]_{33.4K}$ | 2.92 | 60 |
| PRx-4 | $[D]_{10.7K}$-$[B_{50}$-$P_{27}$-$D_{23}]_{33.8K}$ | 3.16 | 50 |
| PRx-5 | $[D]_{10.7K}$-$[B_{40}$-$P_{31}$-$D_{29}]_{32.2K}$ | 3.00 | 59 |
| PRx-6 | $[D]_{14.5K}$-$[B_{53}$-$P_{31}$-$D_{16}]_{67.0K}$ | 4.62 | 115 |

In a specific embodiment, a compound of Formula IV3 is a polymer of the P7 class called PRx0729v6. PRx0729v6 is used interchangeably with P7v6 in this application and in various priority applications.

Spacer Block

In some embodiments, block copolymers of the present invention comprise one or more optional blocks. These blocks may be spacer blocks.

Provided in certain embodiments, at least one block copolymer described herein further comprises a spacer block. In some embodiments, the spacer block is a hydrophilic block between the hydrophobic block and a polynucleotide carrier block.

Shielding Hydrophilic Segment/Block

In certain embodiments, the polymeric carriers described herein comprise one or more shielding agents. In some embodiments, the polynucleotide carrier block/segment comprises a PEG substituted monomeric unit (e.g., the PEG is a side chain and does not comprise the backbone of the polynucleotide carrier block). In some instances, one or more of the polymers (e.g., block copolymers) utilized in the polymeric carriers described herein comprise polyethyleneglycol (PEG) chains or blocks with molecular weights of approximately from 1,000 to approximately 30,000. In some embodiments, PEG is conjugated to polymer ends groups, or to one or more pendant modifiable group present in a polymer of a polymeric carrier provided herein. In some embodiments, PEG residues are conjugated to modifiable groups within the hydrophilic segment or block (e.g., a shell block) of a polymer (e.g., block copolymer) of a polymeric carrier provided herein. In certain embodiments, a monomer comprising a PEG residue of 2-20 ethylene oxide units is co-polymerized to form the hydrophilic portion of the polymer forming the polymeric carrier provided herein.

In some instances a shielding agent enhances the stability of the therapeutic agent (e.g., polynucleotide or peptide, etc.) against enzymatic digestion in plasma. In some instances, a shielding agent reduces toxicity of polymeric carriers described herein (e.g., block copolymer attached to polynucleotides). In some instances, a shielding agent imparts a favorable surface property to the polymeric carrier. In some embodiments, a shielding agent comprises a plurality of neutral hydrophilic monomeric residues. In some instances, a shielding polymer is covalently coupled to a membrane destabilizing block copolymer through an end group of the polymer. In some embodiments, a shielding agent is a covalently coupled pendant moiety attached to one or more monomeric residues of the polymer. In some embodiments, a plurality of monomeric residues in a polymeric carrier described herein comprise pendant shielding species (e.g., a polyethylene glycol (PEG) oligomer (e.g., having 20 or less repeat units) or polymer (e.g, having more than 20 repeat units)) covalently coupled through a functional group to the polyethylene glycol oligomer or polymer. In some instances, a block copolymer comprises a polyethylene gylcol (PEG) oligomer or polymer covalently coupled to the alpha end or the omega end of the membrane destabilizing block of the copolymer.

In certain embodiments, the polynucleotide carrier block/segment comprises a monomeric unit that serves to shield, at least in part, the charge (e.g., cationic charges) on the polynucleotide carrier block/segment. In particular embodiments, the shielding arises, at least in part, form a pendant moiety on the monomeric unit that comprises, at least part, of the polynucleotide carrier block/segment. Such shielding optionally lowers the cellular toxicity from excessive charges in this segment.

Polynucleotide Attachment to Polymers of the Polymeric Carrier

In some embodiments, a polynucleotide (e.g., oligonucleotide) is attached (e.g., covalently or non-covalently) to one or more of the plurality of polymers of any polymeric carrier described herein. In such embodiments, the polynucleotide can be attached to the polymer(s) by any suitable technique (e.g., a chemical conjugation technique). In specific embodiments, the polynucleotide is attached to a polynucleotide carrier block or segment of a polymer of the polymeric carrier. In certain specific embodiments, the polynucleotide is attached at or near the alpha end (i.e., the end where polymerization was initiated) or at or near the omega end (i.e., the end where polymerization was terminated) of a polymer of any polymeric carrier described herein. In some specific embodiments, a polynucleotide is attached to a polymer of any polymeric carrier described herein by conjugation of the polynucleotide with a conjugatable moiety at the alpha end of the polymer. In certain specific embodiments, a polynucleotide is attached to a polymer of any polymeric carrier described herein by conjugation of the polynucleotide with a conjugatable moiety at the omega end of the polymer. In various embodiments, a polynucleotide is a polynucleotide is attached to a polymer of any polymeric carrier described herein by conjugation of the polynucleotide with a conjugatable moiety at the alpha end of the polymer attached to the polymer through linking moiety (e.g., a covalent bond or a chemical moiety). In some embodiments, polynucleotides are conjugated to pendant groups attached to the monomeric units of the polymer. In various embodiments, the linking moiety is optionally non-cleavable, or cleavable. In certain embodiments, a cleavable bond that attaches the polynucleotide to a polymer of a polymeric carrier described herein includes, by way of non-limiting example, disulfide bonds (e.g., disulfide bonds that dissociate in the reducing environment of the cytoplasm). In some embodiments, the linking moiety is cleavable and/or comprises a bond that is cleavable in endosomal conditions. In some embodiments, the linking moiety is cleavable and/or comprises a bond that is cleavable by a specific enzyme (e.g., a phosphatase, or a protease). In some embodiments, the linking moiety is cleavable and/or comprises a bond that is cleavable upon a change in an intracellular parameter (e.g., pH, redox potential). In some embodiments, covalent association between a polymer (e.g., the alpha or omega end conjugatable group of the polymer) and a polynucleotide (e.g., an oligonucleotide or siRNA) is achieved through any suitable chemical conjugation method, including but not limited to amine-carboxyl linkers, amine-aldehyde linkers, amine-ketone linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In some embodiments, a bifunctional crosslinking reagent is employed to achieve the covalent conjugation between suitable conjugatable groups of a polynucleotide and polymer of a polymeric carrier described herein. In some embodiments, attachment is also performed with pH-sensitive bonds and linkers, including, but not limited to, hydrazone and acetal linkages. In certain embodiments, polynucleotide is covalently linked to a boronic acid functionality (e.g., a phenylboronic acid residue) incorporated into the alpha or the omega end of the polymer through the formation of an ester of the boronic acid with the 2' and 3'-hydroxyl of the terminal ribose residue of the polynucleotide. Any other suitable conjugation/attachment method is optionally utilized as well, for example a large variety of conjugation chemistries are available (see, for example, *Bioconjugation*, Aslam and Dent, Eds, Macmillan, 1998 and chapters therein). Moreover, in certain embodiments, a polynucleotide is attached to a polymer of a polymeric carrier, or to the polynucleotide carrier block thereof (e.g., a cationically charged polynucleotide carrier block), by complexing the polynucleotide to the polymer through ionic (i.e., anion-cationic) interactions.

Targeting.

In specific instances, the polymeric carriers provided herein are useful for delivery of polynucleotides (e.g., oligonucleotides) to cells of an individual, which may be specifically targeted for a selected cell type. In certain instances, the efficiency of the cell uptake of the polymeric carriers (e.g., polymeric carriers comprising a polynucleotide, such as an oligonucleotide or siRNA) is enhanced by incorporation of targeting moieties into or on the surface of the polymeric carrier. As such, in some embodiments, provided herein is a polymeric carrier comprising a targeting agent. A "targeting moiety" (used interchangeably with "targeting agent") recognizes the surface of a cell (e.g., a selected cell). In specific embodiments, the targeting agent binds to the surface of a cell (e.g., a selected cell). In some embodiments, targeting moieties recognize a cell surface antigen or bind to a receptor on the surface of the target cell. Suitable targeting moieties include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting moieties of the polymeric carriers (e.g., micelles) provided herein include, but are not limited to, the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor.

Targeting moieties are attached, in various embodiments, to either end of the polymer (e.g., block copolymer), or to a side chain of a monomeric unit, or incorporated into a polymer block. Attachment of the targeting moiety to the polymer is achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl linkers, carbohydrate-hydroxyl linkers, carbohydrate-carbohydrate linkers, and hydroxyl-hydroxyl linkers. In specific embodiments, "click" chemistry is used to attach the targeting ligand to the block copolymers forming the polymeric carriers provided herein (for example of "click" reactions, see Wu, P.; Fokin, V. V. Catalytic Azide-Alkyne Cycloaddition: Reactivity and Applications. *Aldrichim. Acta* 2007, 40, 7-17). A large variety of conjugation chemistries are optionally utilized (see, for example, *Bioconjugation*, Aslam and Dent, Eds, Macmillan, 1998 and chapters therein). In some embodiments, targeting ligands are attached to a monomer and the resulting compound is then used in the polymerization synthesis of a polymer (e.g., block copolymer) utilized in a polymeric carrier described herein. In some embodiments, targeting moieties are attached to a block of the first block copolymer, or to a block of a second block copolymer (e.g., wherein a first bock copolymer is attached to a polynucleotide, such as an siRNA). In some embodiments, the targeting ligand is attached to the sense or antisense strand of siRNA bound to a block copolymer. In certain embodiments, the targeting agent is attached to a 5' or a 3' end of the sense or the antisense strand.

In specific embodiments, the block copolymers forming the polymeric carriers provided herein are biocompatible. As used herein, "biocompatible" refers to a property of a polymer characterized by it, or its in vivo degradation products, being not, or at least minimally and/or reparably, injurious to living tissue; and/or not, or at least minimally and controllably, causing an immunological reaction in living tissue. With regard to salts, it is presently preferred that both the cationic and the anionic species be biocompatible. As used herein, "physiologically acceptable" is interchangeable with biocompatible. In some instances, the polymeric carriers and polymers used therein (e.g., block copolymers) exhibit low toxicity compared to cationic lipids.

In some embodiments, polymeric carriers provided herein have superior commercial viability relative to other technologies for delivery polynucleotides, including but not limited to: decreased immunogenicity of the carrier following repeat in vivo administration; fewer steps needed to assemble the multiple elements of the delivery vehicle, resulting in lower cost of goods; and reproducibility of manufacture, e.g., as judged by the ability to manufacture repeated batches of product with less than 5%, less than 10%, or less than 20% batch-to-batch variability in biophysical assay properties (including, e.g., HPLC, GPC, DLS, and TEM).

Cell Uptake.

In some embodiments, the polymeric carriers comprising polynucleotides (e.g., oligonucleotides or siRNA) are delivered to cells by endocytosis. Intracellular vesicles and endosomes are used interchangeably throughout this specification.

Successful polynucleotide (e.g., oligonucleotide or siRNA) delivery into the cytoplasm generally has a mechanism for endosomal escape. In certain instances, the polymeric carriers comprising polynucleotides (e.g., oligonucleotide or siRNA) provided herein are sensitive to the lower pH in the endosomal compartment upon endocytosis. In certain instances, endocytosis triggers protonation or charge neutralization of anionically chargeable species (e.g., propyl acrylic acid units) of the polymeric carrier, resulting in a conformational transition in the polymeric carrier. In certain instances, this conformational transition results in a more hydrophobic membrane destabilizing form which mediates release of the polynucleotide (e.g., oligonucleotide or siRNA) from the endosomes to the cytoplasm. In those polymeric carriers comprising siRNA, delivery of siRNA into the cytoplasm allows its mRNA knockdown effect to occur. In those polymeric carriers comprising other types of oligonucleotides, delivery into the cytoplasm allows their desired action to occur.

Polynucleotides.

Polymeric carriers described herein are also useful for delivery of polynucleotides to a subject in need thereof. Polynucleotides are nucleic acid polymers having a plurality of nucleotides, e.g., over 200 nucleotides. In one embodiment, the polynucleotide is a mammalian expression vector. In another embodiment, the polynucleotide is designed to recombine with and correct an endogenous gene sequence in a human. In some embodiments, a polynucleotide provided in a polymeric carrier described herein is a gene expression modulator. In certain embodiments, a polynucleotide provided in a polymeric carrier described herein is a knockdown agent (e.g., a knockdown oligonucleotide, such as an siRNA). Polynucleotides utilized herein also optionally include messenger RNA (mRNA), and RNA or DNA decoys (e.g., that compete for binding of an endogenous nucleic acid sequence to its intracellular target), or nucleic acid aptamers (e.g., that bind to intracellular macromolecules).

A mammalian expression vector comprises a complimentary DNA sequence (a "cDNA" or mini-gene) that is functionally linked to a promoter region such that the promoter drives expression of the cDNA. In certain instances, mammalian expression vectors also comprise a polyadenylation signal at the 3' end of the cDNA. A promoter region is a nucleotide segment that is recognized by a RNA polymerase molecule, in order to initiate RNA synthesis (i.e., transcription), and may also include other transcriptional regulatory elements such as enhancers. Any number of transcriptional regulatory sequences may be used to mediate expression of linked genes in mammalian expression vectors. Promoters include but are not limited to retroviral promoters, other viral promoters such as those derived from HSV or CMV, and promoters from endogenous cellular genes. Mammalian expression vectors also typically have an origin of replication from E. Coli to enable propagation as plasmids in bacteria.

It is desirable to be able to introduce mammalian expression vectors into mammalian cells in culture or in vivo. In some embodiments, expression vectors are transfected into mammalian cells using the polymeric carriers of the present invention.

As described herein, the polymeric carriers provided herein are used, in some embodiments, for delivery of polynucleotides into a cell or to an individual in need thereof. In certain embodiments, the polymeric carrier's polycationic blocks bind to the mammalian expression vector DNA and complexes the DNA with the polymeric carrier. In certain instances, polycations bind to and complex with mammalian expression vectors DNA. In some embodiments, a polymeric carrier comprising a polynucleotide complex is charge neutralized (e.g., the shell of the polymeric carrier or the shell block of a polymer of the polymeric carrier and the polynucleotide are substantially charge neutralized). Depending on the length of the polynucleotide, the length of the polycationic block is optionally adjusted to provide charge neutralization for the polynucleotide. In some instances, charge-neutralization is achieved by addition of cations and/or polycations into the formulation. In some embodiments, a polymeric carrier comprising a polymer and a polynucleotide (e.g., a 200+mer) is then diluted as necessary in an appropriate buffer and added directly to cells in culture. Expression of the transfected gene or cDNA in the resulting cells can be readily measured by including in the mammalian expression vector an expression cassette driving an indicator gene such as luciferase, chloramphenicol acetyl transferase or GFP. These genes are readily available and reporter assays are described.

In some embodiments, polymeric carriers provided herein are used for gene therapy. The treatment of diseases and disorders by gene therapy generally involves the transfer of new genetic information into cells. "Gene therapy vectors" comprise the new genetic material to be delivered, which is, optionally, in a mammalian expression vector. The uses of polymeric carriers include delivery of DNA sequences for gene replacement, inhibition of gene expression, gene correction or gene augmentation, or the introduction of genes to have some other desired effect, such as the modulation of immune responses. Inhibition of gene expression is accomplished in any suitable manner, including, by way of non-limiting example, by expression of gene cassettes in cells which express shRNAs or other RNAi agents.

In some embodiments, polymeric carriers having a non-core polycationic block are mixed with gene therapy vectors, such that they become bound to the polymeric carrier. The polymeric carrier-gene therapy vector complex, in a suitable excipient (see below) is then administered to a living subject by routes including but not limited to intravenous, intra-arcticular, intrathecal, intracranial, inhalation, sub-cutaneous or intra-ocular.

Uses—GeneRx

Polymeric carriers comprising a polynucleotide are useful in treating a number of diseases. A non-limiting list of such diseases that are suitable for treatment with polymeric carrier-gene therapy vectors provided herein include but are not limited to: hemophilias A and B; cystic fibrosis; hypercholesterolemia; hemoglobinopathies such as thalassemias and sickle-cell anemia; cancer; inflammatory disease and lysosomal storage disorders.

Target Gene Families and Diseases.

Diseases that are optionally treated using polymeric carriers (e.g., those comprising siRNA) provided herein include, without limitation, pathogenic disorders, cancers, inflammatory diseases, enzyme deficiencies, inborn errors of metabolism, infections, auto-immune diseases, cardiovascular diseases, neurological, neurodegenerative, diseases, neuromuscular diseases, blood disorders and clotting disorders. In some embodiments, the non-limiting examples of the siRNA decreases or down-regulate expression of, or can be originated from, PTP1B, dual-specificity phosphatases (DSP), c-myc, c-myb, c-fos, c-jun, c-raf, c-src, bcl-2, vascular endothelial growth factor (VEGF), VEGF-B, VEGF-C, VEGF-D, or PIGF.

In some embodiments, the polymeric carriers (e.g., micelles) provided herein are useful in treating a subject at risk for or afflicted with disorders associated with and/or caused by high plasma levels or cholesterol, apolipoprotein b, and/or LDL cholesterol, e.g. hypercholesterolemia. In some embodiments, the treatment comprises providing a polymeric carrier comprising a polynucleotide agent (e.g., an oligonucleotide agent), wherein the polynucleotide agent silences (e.g., by cleavage) a gene or a gene product which promotes such condition. In some embodiments the polynucleotide agent silences proprotein convertase subtilisin/kexin type 9 (PCSK9) gene responsible for regulation of low density lipoprotein (LDLR) levels and function, and thus polymeric carriers comprising such polynucleotide agent is used to treat a subject having or at risk for a disorder characterized by unwanted PCSK9 expression, e.g., disorders associated with and/or caused by high plasma levels or cholesterol, apolipoprotein b, and/or LDL cholesterol, e.g. hypercholesterolemia. In some embodiments, the polymeric carrier deliver PCSK9-silencing polynucleotide agent (e.g, siRNA) to a cell expressing PCSK9. In some embodiments, the cell is a liver cell.

In some embodiments, the polymeric carriers (e.g., micelles) provided herein are useful in treating a subject at risk for or afflicted with unwanted cell proliferation (e.g., malignant or nonmalignant cell proliferation). The treatment comprises providing a polymeric carrier comprising a polynucleotide agent (e.g., an oligonucleotide agent), wherein the polynucleotide is homologous to and can silence (e.g., by cleavage) a gene which promotes unwanted cell proliferation; and administering a therapeutically effective dose of the polymeric carrier to a subject (e.g., a human subject.).

In certain embodiments, the gene is but is not limited to a growth factor or growth factor receptor gene, a phosphatase, a kinase, e.g., a protein tyrosine, serine or threonine kinase gene, an adaptor protein gene, a gene encoding a G protein superfamily molecule, or a gene encoding a transcription factor. In some instances, the polymeric carrier comprises a polynucleotide which silences a gene which is expressed in a specific tissue or organ, including, but not limited to lung, pancreas, liver, kidney, ovary, muscle, skin, breast, colon, stomach, and the like.

In some embodiments, the oligonucleotide agent silences one or more of the following genes: the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers, and chronic leukemia; the MEKK gene, and thus can be used to treat a subject having or at risk for a disorder characterized by unwanted MEKK expression, e.g., squamous cell carcinoma, melanoma or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA (p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c-MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL-2 gene, and thus can be used to treat a subject having or at risk for a disorder characterized by unwanted BCL-2 expression, e.g., lung or prostate cancers or Non-Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT-1 expression, e.g., basal cell carcinoma; the beta-catenin gene, and thus can be used to treat a subject having or at risk for a disorder characterized by unwanted beta-catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the topoisomerase I gene, and thus can be used to treat a subject having or at risk for a disorder characterized by unwanted topoisomerase I expression, e.g., ovarian and colon cancers; the topoisomerase II alpha gene, and thus can be used to treat a subject having or at risk for a disorder characterized by unwanted topoisomerase II expression, e.g., breast and colon cancers.

In other embodiments the oligonucleotide agent silences mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21(WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the oligonucleotide agent silences mutations in tumor suppressor genes, and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN-p63, the pRb tumor suppressor gene, the APC1 tumor suppressor gene, the BRCA1 tumor suppressor gene, the PTEN tumor suppressor gene.

In some embodiments the oligonucleotide agent silences one of the following fusion genes: mLL fusion genes, e.g., mLL-AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/FUS1 fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some aspects herein the polymeric carriers provide therapeutic agents for treating a subject, e.g., a human, at risk for or afflicted with a disease or disorder that may benefit by angiogenesis inhibition e.g., cancer or retinal degeneration. The treatment comprises providing a polymeric carrier comprising an oligonucleotide agent, wherein said oligonucleotide agent is homologous to and/or can silence, e.g., by cleavage, a gene which mediates angiogenesis (e.g., VEGF-R1, VEGF-R2 or a gene encoding signaling proteins for these receptors' pathways); and administering a therapeutically effective dosage of said polymeric carrier comprising the oligonucleotide agent to a subject, e.g., a human subject.

In some embodiments the oligonucleotide agent silences one of the following genes: the alpha v-integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the polymeric carriers comprising oligonucleotide agents provided herein relate to a method of treating a subject infected with a virus or at risk for or afflicted with a disorder or disease associated with a viral infection. The method comprises providing a polymeric carrier comprising an oligonucleotide agent, wherein said oligonucleotide agent is homologous to and/or can silence, e.g., by cleavage, a viral gene or a cellular gene which mediates viral function, e.g., entry or growth; and administering a therapeutically effective dose of said oligonucleotide agent to a subject, e.g., a human subject.

In some embodiments, the polymeric carriers comprising an oligonucleotide agent are useful in treatment of subjects infected with the Human Papilloma Virus (HPV) or at risk for or afflicted with a disorder mediated by HPV, e.g, cervical cancer.

In some embodiments, the polymeric carrier comprises an oligonucleotide agent silencing expression of a HPV gene is reduced. In some embodiments, the HPV gene is selected from the group of E2, E6, or E7.

In another embodiment the expression of a human gene that is required for HPV replication is reduced.

In some embodiments, the polymeric carrier comprises an oligonucleotide agent useful in treating patients infected by the Human Immunodeficiency Virus (HIV) or at risk for or afflicted with a disorder mediated by HIV, e.g., Acquired Immune Deficiency Syndrome (AIDS). In some embodiments, the expression of an HIV gene is reduced. In other embodiments, the HIV gene is CCR5, Gag, or Rev. In some embodiments the expression of a human gene that is required for HIV replication is reduced. In some embodiments, the gene is CD4 or Tsg101.

In some embodiments, the polymeric carrier comprises an oligonucleotide agent useful for treating patients infected by the Hepatitis B Virus (HBV) or at risk for or afflicted with a disorder mediated by HBV, e.g., cirrhosis and heptocellular carcinoma. In one embodiment, the expression of a HBV gene is reduced. In other embodiment, the targeted HBV gene encodes one of the groups of the tail region of the HBV core protein, the pre-cregious (pre-c) region, or the cregious (c) region. In other embodiments a targeted HBV-RNA sequence is comprised of the poly(A) tail. In some embodiments the expression of a human gene that is required for HBV replication is reduced.

In some embodiments, the polymeric carrier comprises an oligonucleotide agent useful for treating patients infected with, or at risk for or afflicted with a disorder mediated by a virus selected from the following viruses: the Hepatitis A Virus (HAV); Hepatitis C Virus (HCV); any of the group of Hepatitis Viral strains comprising hepatitis D, E, F, G, or H; the Respiratory Syncytial Virus (RSV); the herpes Cytomegalovirus (CMV); the herpes Epstein Barr Virus (EBV); Kaposi's Sarcoma-associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick-borne encephalitis flavivirus; the Murray Valley encephalitis flavivirus; the dengue flavivirus;

the Simian Virus 40 (SV40); the encephalomyocarditis virus (EMCV); the measles virus (MV); the Varicella zoster virus (VZV); an adenovirus (e.g. virus causing a respiratory tract infection); the poliovirus; or a poxvirus (a poxvirus causing smallpox). In some embodiments the expression of a human gene that is required for the replication of these viruses is reduced.

In some embodiments, the polymeric carrier comprises an oligonucleotide agent useful for treating patients infected by the Herpes Simplex Virus (HSV) or at risk for or afflicted with a disorder mediated by HSV, e.g, genital herpes and cold sores as well as life-threatening or sight-impairing disease, e.g., mainly in immunocompromised patients. In some embodiments, the expression of a HSV gene is reduced. In other embodiment, the targeted HSV gene encodes DNA polymerase or the helicase-primase. In some embodiments the expression of a human gene that is required for HSV replication is reduced.

In some embodiments, the polymeric carrier comprises an oligonucleotide agent useful for treating patients infected by the West Nile Virusor at risk for or afflicted with a disorder mediated by West Nile Virus. In some embodiments, the expression of a West Nile Virus gene is reduced. In other preferred embodiments, the West Nile Virus gene is selected from the group comprising E, NS3, or NS5. In some embodiments the expression of a human gene that is required for West Nile Virus replication is reduced.

In some embodiments, the polymeric carrier comprises an oligonucleotide agent useful for treating patients infected by the Human T Cell Lymphotropic Virus (HTLV), or a disease or disorder associated with this virus, e.g., leukemia or myelopathy. In some embodiments, the expression of a HTLV gene is reduced. In some embodiments, the HTLV1 gene is the Tax transcriptional activator. In some embodiments, the expression of a human gene that is required for HTLV replication is reduced.

In some aspects, the polymeric carrier comprises an oligonucleotide agent useful for treating a subject infected with a pathogen, e.g., a bacterial, amoebic, parasitic, or fungal pathogen. The method of treatment comprises providing a polymeric carrier comprising an oligonucleotide agent, wherein said oligonucleotide is homologous to and/or can silence, e.g., by cleavage of a pathogen gene or a gene involved in the pathogen's growth; and administering a therapeutically effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production.

Thus, in some embodiments, the polymeric carrier comprises an oligonucleotide agent useful for of treating patients infected by a *plasmodium* that causes malaria. In some embodiments, the expression of a *plasmodium* gene is reduced. In other embodiments, the gene is apical membrane antigen 1 (AMA1). In some embodiments, the expression of a human gene that is required for *plasmodium* replication is reduced.

In some embodiments, the polymeric carrier comprises an oligonucleotide agent useful for treating patients infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is reduced.

In some embodiments, the diseases treated by the polymeric carriers provided herein may be systemic or present in a specific tissue, e.g., the lung, skin, liver, breast, kidney, pancreas, CNS, or the like. In certain aspects, the oligonucleotide silences a gene which mediates or is involved in a metabolic disease or disorder, e.g., diabetes, obesity, and the like. In certain embodiments, the oligonucleotide silences a gene which mediates or is involved in a pulmonary disease or disorder, e.g., chronic obstructive pulmonary disease (COPD), cystic fibrosis, or lung cancer.

In some aspects herein, the polymeric carriers comprise an oligonucleotide agent useful for and/or related to a method of treating a subject, e.g., a human, at risk for or afflicted with a disease or disorder characterized by an unwanted immune response, e.g., an inflammatory disease or disorder or an autoimmune disease or disorder. The method comprises providing a polymeric carrier comprising an oligonucleotide agent, wherein said oligonucleotide agent is homologous to and/or can silence, e.g., by cleavage, a gene which mediates an unwanted immune response; and administering said oligonucleotide agent to a subject, e.g., a human subject. In some embodiments, the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention e.g., angioplasty, e.g., percutaneous transluminal coronary angioplasty. In other embodiments, the disease or disorder is Inflammatory Bowel Disease, e.g., Crohn Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments the oligonucleotide agent silences an integrin or co-ligand thereof, e.g., VLA4, VCAM, ICAM. In other embodiments the oligonucleotide agent silences a selectin or co-ligand thereof, e.g., P-selectin, E-selectin (ELAM), I-selectin, P-selectin glycoprotein-1 (PSGL-1). In certain embodiments the oligonucleotide agent silences a component of the complement system, e.g., C3, C5, C3aR, C5aR, C3 convertase, and C5 convertase. In some embodiments the oligonucleotide agent silences a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, and CCR3. In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

In some aspects, the polymeric carriers comprise an oligonucleotide agent useful for treating a subject, e.g., a human, at risk for or afflicted with a neurological disease or disorder. The method comprises providing a polymeric carrier comprising an oligonucleotide agent, wherein said oligonucleotide is homologous to and/or can silence, e.g., by cleavage, a gene which mediates a neurological disease or disorder; and administering a therapeutically effective dose of said oligonucleotide agent to a subject, e.g., a human. In some embodiments the disease or disorder is Alzheimer Disease or Parkinson Disease. In certain embodiments the oligonucleotide agent silences an amyloid-family gene, e.g., APP; a presenilin gene, e.g., PSEN1 and PSEN2, or I-synuclein. In other embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8. In some embodiments the oligonucleotide agent silences HD, DRPLA, SCA1, SCA2, MJD1, CACNL1A4, SCA7, or SCA8.

In certain aspects, the polymeric carriers provided herein comprise an oligonucleotide agent capable of cleaving or silencing more than one gene. In these embodiments the oligonucleotide agent is selected so that it has sufficient homology to a sequence found in more than one gene, e.g. a sequence conserved between these genes. Thus in some embodiments an oligonucleotide agent targeted to such sequences effectively silences the entire collection of genes.

In some aspects, the polymeric carriers provided herein comprise two or more types of oligonucleotide agents wherein the oligonucleotide agents silence different genes of the same disease or different diseases.

In some embodiments, a polymeric carrier (e.g., comprising an oligonucleotide) provided herein is administered in conjunction with another treatments for a targeted disease condition. In some embodiments, a polymeric carrier (e.g., comprising an oligonucleotide) provided herein is administered in conjunction with therapeutic agents effective against inflammatory diseases, such as RA or psoriasis. Examples of combinatorially useful and effective agents in this context include non-steroidal anti-inflammatory drugs (NSAIDs), methotrexate, gold compounds, D-penicillamine, the antimalarials, sulfasalazine, glucocorticoids, and other TNF-α neutralizing agents such as infliximab and entracept. In certain instances, the non-oligonucleotide is encapsulated in the core of the micelle.

Where combination treatments or prevention methods are contemplated, it is not intended that the agents described herein be limited by the particular nature of the combination. For example, the agents described herein are optionally administered in combination as simple mixtures as well as chemical hybrids. Furthermore, combination treatments are optionally administered separately or concomitantly.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the agents described herein, and at least one co-agent, are both administered to a patient simultaneously in the form of a single entity or dosage. The term "non-fixed combination" means that at least one of the agents described herein, and at least one co-agent, are administered to a patient as separate entities either simultaneously, concurrently or sequentially with variable intervening time limits, wherein such administration provides effective levels of the two or more agents in the body of the patient. In some instances, the co-agent is administered once or for a period of time, after which the agent is administered once or over a period of time. In other instances, the co-agent is administered for a period of time, after which, a therapy involving the administration of both the co-agent and the agent are administered. In still other embodiments, the agent is administered once or over a period of time, after which, the co-agent is administered once or over a period of time. These also apply to cocktail therapies, e.g. the administration of three or more active ingredients.

As used herein, the terms "co-administration", "administered in combination with" and their grammatical equivalents are meant to encompass administration of the selected therapeutic agents to a single patient, and are intended to include treatment regimens in which the agents are administered by the same or different route of administration or at the same or different times. In some embodiments the agents described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the agents described herein and the other agent(s) are administered in a single composition. In some embodiments, the agents described herein and the other agent(s) are admixed in the composition.

The terms "effective amount" or "therapeutically effective amount" as used herein, refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system. In specific instances, the result is a sufficient knock down of a targeted gene to provide a result, e.g., a reduction of a disease or disorder treated or symptoms associated therewith. In certain instances, an "effective amount" for therapeutic uses is the amount of the composition comprising an agent as set forth herein required to provide a clinically significant decrease in a disease. An appropriate "effective" amount in any individual case is determined using any suitable technique, such as a dose escalation study.

The terms "administer," "administering", "administration," and the like, as used herein, refer to the methods that may be used to enable delivery of agents or compositions to the desired site of biological action. These methods include, but are not limited to oral routes, intraduodenal routes, parenteral injection (including intravenous, subcutaneous, intraperitoneal, intramuscular, intravascular or infusion), transdermal, topical and rectal administration. Those of skill in the art are familiar with administration techniques that can be employed with the agents and methods described herein, e.g., as discussed in Goodman and Gilman, The Pharmacological Basis of Therapeutics, current ed.; Pergamon; and Remington's Pharmaceutical *Sciences* (current edition), Mack Publishing Co., Easton, Pa. In certain embodiments, the polymeric carriers described herein are administered by parenteral injection (e.g., intravenous, subcutaneous, intraperitoneal, intramuscular, intravascular or infusion).

Formulations.

Polymeric carriers—oligonucleotide compositions of this disclosure can be administered to a patient in any suitable manner, e.g., with or without stabilizers, buffers, and the like, to form a pharmaceutical composition. In some embodiments, the polymeric carriers provided herein are formulated and used as tablets, capsules or elixirs for oral administration, suppositories for rectal administration, sterile solutions, suspensions for injectable administration, and any other suitable compositions.

Provided are pharmaceutically acceptable formulations of the compositions described herein. These formulations include salts of the above compounds, e.g., acid addition salts, e.g., salts of hydrochloric, hydrobromic, acetic acid, and benzene sulfonic acid. A pharmacological composition or formulation refers to a composition or formulation in a form suitable for administration, e.g., systemic administration, into a cell or patient, including for example a human. Suitable forms, in part, depend upon the use or the route of entry, e.g., oral, transdermal, or by injection. Thus, in specific embodiments wherein the polymeric carrier comprises and is delivering a polynucleotide, the formulation is in a form that does not prevent the polymeric carrier and, more specifically, the polynucleotide (e.g., oligonucleotide or siRNA) from reaching a target cell with the polynucleotide intact and/or functional. For example, in certain embodiments, pharmacological compositions injected into the blood stream are soluble and/or dispersible. Moreover, pharmaceutical compositions described herein are, preferably, non-toxic. In some embodiments, wherein a polymeric carrier described herein is administered for therapeutic benefit, a therapeutic effective amount of the polymeric carrier comprising the polynucleotide (e.g., siRNA) is administered. In an exemplary embodiment, a therapeutically effective amount includes an amount sufficient polymeric carrier to provide about 10 mg or less of siRNA per kg of individual.

In some embodiments, pharmaceutical compositions comprising a polymeric carrier, which comprise a polynucleotide (e.g., oligonucleotide or siRNA), are administered systemically. As used herein, "systemic administration" means in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. In some embodiments, the oligonucleotide—polymeric carrier compositions are administered topically.

In some embodiments, the compositions are prepared for storage or administration and include a pharmaceutically effective amount of the oligonucleotide-polymeric carrier composition in a pharmaceutically acceptable carrier or diluent. Any acceptable carriers or diluents are optionally utilized herein. Specific carriers and diluents and are described, e.g., in *Remington's Pharmaceutical Sciences*, Mack Publishing Co., A. R. Gennaro Ed., 1985. For example, preservatives, stabilizers, dyes and flavoring agents are optionally added. These include sodium benzoate, sorbic acid and esters of p-hydroxybenzoic acid. In addition, antioxidants and suspending agents are optionally used. As used herein, the term "pharmaceutically acceptable carrier" means a non-toxic, inert solid, semi-solid or liquid filler, diluent, encapsulating material or formulation auxiliary of any type. Some examples of materials optionally used as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. In some embodiments, he pharmaceutical compositions provided herein are administered to humans and/or to animals, orally, rectally, parenterally, intracistemally, intravaginally, intranasally, intraperitoneally, topically (as by powders, creams, ointments, or drops), subcutaneously, bucally, or as an oral or nasal spray.

In various embodiments, liquid dosage forms for oral administration include pharmaceutically acceptable emulsions, microemulsions, solutions, suspensions, syrups, and elixirs. In addition to the active ingredients (i.e., micelle-oligonucleotide complexes of the present invention), the liquid dosage forms optionally further contain inert diluents or excipients, such as by way of non-limiting example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions optionally also include adjuvants such as wetting agents, emulsifying and suspending agents, sweetening, flavoring, and perfuming agents.

In some embodiments, injectable preparations, for example, sterile injectable aqueous or oleaginous suspensions are formulated according in any suitable manner, e.g., using dispersing agents, wetting agents and/or suspending agents. The sterile injectable preparation is, optionally, a sterile injectable solution, suspension, or emulsion in a nontoxic parenterally acceptable diluent or solvent, for example, as a solution in 1,3-butanediol. Among the acceptable vehicles and solvents that are optionally employed are water, Ringer's solution, U.S.P. and isotonic sodium chloride solution. In addition, sterile, fixed oils are conventionally employed as a solvent or suspending medium. For this purpose any bland fixed oil is optionally employed including synthetic mono- or diglycerides. In additional embodiments, fatty acids such as oleic acid are used in the preparation of injectables. In a specific embodiment, the polymeric carrier particles are suspended in a carrier fluid comprising 1% (w/v) sodium carboxymethyl cellulose and 0.1% (v/v) Tween 80.

In some embodiments, the injectable formulations are sterilized, for example, by filtration through a bacteria-retaining filter, or by incorporating sterilizing agents in the form of sterile solid compositions which are optionally dissolved or dispersed in sterile water or other sterile injectable medium prior to use.

In certain embodiments, compositions for rectal or vaginal administration are suppositories. Suppositories are optionally prepared by mixing the polymeric carrier-oligonucleotide complexes with suitable non-irritating excipients or carriers such as cocoa butter, polyethylene glycol, or a suppository wax which are solid at ambient temperature but liquid at body temperature and therefore melt in the rectum or vaginal cavity and release the polymeric carrier microparticles.

Suitable solid dosage forms for oral administration include, by way of non-limiting example, capsules, tablets, pills, powders, and granules. In such solid dosage forms, the polymeric carriers comprising a polynucleotide (e.g., oligonucleotide) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type are also optionally employed as fillers in soft and hard-filled gelatin capsules using such excipients as lactose or milk sugar as well as high molecular weight polyethylene glycols and the like.

In some embodiments, the solid dosage forms of tablets, dragees, capsules, pills, and granules are prepared with coatings and shells such as enteric coatings and other suitable coatings. They optionally contain opacifying agents. In certain embodiments, they are of a composition that they release the active ingredient(s) only, or preferentially, in a certain part of the intestinal tract, optionally, in a delayed manner. Examples of suitable embedding compositions include, by way of non-limiting example, polymeric substances and waxes.

Solid compositions of a similar type are optionally employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include, by way of non-limiting example, ointments, pastes, creams, lotions, gels, powders, solutions, sprays, inhalants, or patches. In some embodiments, the polymeric carrier comprising a polynucleotide (e.g., oligonucleotide or siRNA) is admixed under sterile conditions with a pharmaceutically acceptable carrier and, optionally, one or more preservative, one or more buffer, or a combination thereof (e.g., as may be required). Ophthalmic formulation, ear drops, and eye drops are also contemplated as being within the scope of this invention.

Ointments, pastes, creams, and gels provided herein optionally contain, in addition to the polymeric carrier comprising a polynucleotide (e.g., oligonucleotide or siRNA), excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays optionally contain, in addition to the polymeric carrier comprising a polynucleotide (e.g., oligonucleotide or siRNA), excipients such as lactose, talc, silicic acid, aluminum hydroxide, calcium silicates, and polyamide powder, or mixtures of these substances. In some embodiments, sprays additionally contain customary propellants such as chlorofluorohydrocarbons.

Transdermal patches have the added advantage of providing controlled delivery of a compound to the body. Such dosage forms are made in any suitable manner, e.g., by dissolving or dispensing the microparticles or nanoparticles in a proper medium. Absorption enhancers are optionally used to increase the flux of the compound across the skin. The rate can be controlled by either providing a rate controlling membrane or by dispersing the polymeric carrier-oligonucleotide complexes in a polymer matrix or gel.

In some aspects of the invention, the polymeric carrier(s) provide some properties (e.g. mechanical, thermal, etc.) that are usually performed by excipients, thus decreasing the amount of such excipients required for the formulation.

Uses as Research Reagents.

Polymeric carriers provided herein are also optionally used as research reagents or kits for the introduction of oligo- or poly-nucleotides into mammalian cells. Existing methods for introducing (transfecting) oligo- or poly-nucleotides such as mammalian expression vectors into mammalian cells in vitro may be effected by calcium phosphate transfection (Graham and Vander Eb. (1973) Virol. 52:456-467), DEAE-dextran transfection (Lopata, M. A. et al., (1984) Nuclo Acids Res. 12:5707), and electroporation (Potter, H. et al. (1984) PNAS 81:7161), as well as using commercially available reagents such as Lipofectamine (ref.). Such methods suffer from issues of toxicity, and it would be desirable to have a less toxic yet efficient transfection system such as that described herein. Other oligo- or poly-nucleotides that may be delivered using polymeric carriers provided herein include but are not limited to RNA which encodes proteins; ribozymes, aptamers, knock down agents, and decoys. Polymeric carriers provided herein may be especially useful as research reagents for the delivery of RNAi agents in cell culture or in vivo.

Certain Definitions

It is understood that, with regard to this application, use of the singular includes the plural and vice versa unless expressly stated to be otherwise. That is, "a" and "the" refer to one or more of whatever the word modifies. For example, "the polymer" or "a nucleotide" may refer to one polymer or nucleotide or to a plurality of polymers or nucleotides. By the same token, "polymers" and "nucleotides" would refer to one polymer or one nucleotide as well as to a plurality of polymers or nucleotides unless, again, it is expressly stated or obvious from the context that such is not intended.

As used herein, two moieties or compounds are "attached" to or "associated" with, such terms being used interchangeably herein, if they are held together by any interaction including, by way of non-limiting example, one or more covalent bonds, one or more non-covalent interactions (e.g., ionic bonds, static forces, van der Waals interactions, combinations thereof, or the like), or a combination thereof.

As used herein, a polymeric carrier described herein is "stable" if the polymer does not disassociate or become destabilized. In certain instances, a stable polymeric carrier is one that has a hydrodynamic particle size that is within 60%, 50%, 40%, 30%, 20%, or 10% of the hydrodynamic particle size of a polymeric carrier comprising the same siRNA and block copolymers initially formed in an aqueous solution at a pH of 7.4. In some instances, a stable polymeric carrier is one that has a concentration of assembly that is within 60%, 50%, 40%, 30%, 20% or 10% of the concentration of assembly of a polymeric carrier comprising the same siRNA and multiblock polymers initially in an aqueous solution at a pH of 7.4

As used herein, a "chargeable species", "chargeable group", or "chargeable monomeric unit" is a species, group or monomeric unit in either a charged or non-charged state. In certain instances, a "chargeable monomeric unit" is one that can be converted to a charged state (either an anionic or cationic charged state) by the addition or removal of an electrophile (e.g., a proton ($H^+$), for example in a pH dependent manner). The use of any of the terms "chargeable species", "chargeable group", or "chargeable monomeric unit" includes the disclosure of any other of a "chargeable species", "chargeable group", or "chargeable monomeric unit" unless otherwise stated. A "chargeable species" that is "charged or chargeable to an anion" or "charged or chargeable to an anionic species" is a species or group that is either in an anionic charged state or non-charged state, but in the non-charged state is capable of being converted to an anionic charged state, e.g., by the removal of an electrophile, such as a proton (H+). In specific embodiments, a chargeable species is a species that is charged to an anion at about neutral pH. It should be emphasized that not every chargeable species on a polymer will be anionic at a pH near the $pK_a$ (acid dissociation constant) of the chargeable species, but rather an equilibrium of anionic and non-anionic species will co-exist. A "chargeable species" that is "charged or chargeable to a cation" or "charged or chargeable to a cationic species" is a species or group that is either in an cationic charged state or non-charged state, but in the non-charged state is capable of being converted to a cationic charged state, e.g., by the addition of an electrophile, such as a proton (H+). In specific embodiments, a chargeable species is a species that is charged to an cation at about neutral pH. It should be emphasized that not every charged cationic species on a polymer will be cationic at a pH near the $pK_a$ (acid dissociation constant) of the charged cationic species, but rather an equilibrium of cationic and non-cationic species will co-exist. "Chargeable monomeric units" described herein are used interchangeably with "chargeable monomeric residues".

As used herein, a "charge neutralized" means a particle having a Zeta potential that is between ±10 to ±30 mV, and/or the presence of a first number (z) of chargeable species that are chargeable to a negative charge (e.g., acidic species that become anionic upon de-protonation) and a second number (0.5·z) of chargeable species that are chargeable to a positive charge (e.g., basic species that become cationic upon protonation).

Oligonucleotide gene expression modulator: as used herein, an "oligonucleotide gene expression modulator" is an oligonucleotide agent capable of inducing a selective modulation of gene expression in a living cell by mechanisms including but not limited to an antisense mechanism or by way of an RNA interference (RNAi)-mediated pathway which may include (i) transcription inactivation; (ii) mRNA degradation or sequestration; (iii) transcriptional inhibition or attenuation or (iv) inhibition or attenuation of translation. Oligonucleotide gene expression modulators include regulatory RNA (e.g., virtually any regulatory RNA) such as, but are not limited to antisense oligonucleotides, miRNA, siRNA, RNAi, shRNA, aiRNA, Dicer substrates, aptamers and any analogs or precursors thereof.

Oligonucleotide knockdown agent: as used herein, an "oligonucleotide knockdown agent" is an oligonucleotide species which can inhibit gene expression by targeting and binding an intracellar nucleic acid in a sequence-specific manner. Non-limiting examples of oligonucleotide knockdown agents include siRNA, miRNA, shRNA, dicer substrates, antisense oligonucleotides, decoy DNA or RNA, antigene oligonucleotides and any analogs and precursors thereof.

Inhibition: The terms "inhibition," "silencing," and "attenuation" as used herein refer to a measurable reduction in expression of a target mRNA or the corresponding protein as compared with the expression of the target mRNA or the corresponding protein in the absence of a knockdown agent. "Knockdown", or the reduction in expression of the target mRNA or the corresponding protein, can be assessed by measuring the mRNA levels using techniques well known in the art such as quantitative polymerase chain reaction (qPCR) amplification, RNA solution hybridization, nuclease protection, northern blotting and hybridization, and gene expression monitoring with a microarray; and in the case of proteins by techniques well known in the art such as SDS-PAGE, antibody binding, western blot analysis, immunoprecipitation, radioimmunoassay or enzyme-linked immunosorbent assay (ELISA), fluorescence activated cell analysis and immunocytochemistry.

Nucleotide: As used herein, the term "nucleotide," in its broadest sense, refers to any compound and/or substance that is or can be incorporated into a polynucleotide (e.g., oligonucleotide) chain. In some embodiments, a nucleotide is a compound and/or substance that is or can be incorporated into a polynucleotide (e.g., oligonucleotide) chain via a phosphodiester linkage. In some embodiments, "nucleotide" refers to individual nucleic acid residues (e.g. nucleotides and/or nucleosides). In certain embodiments, "at least one nucleotide" refers to one or more nucleotides present; in various embodiments, the one or more nucleotides are discrete nucleotides, are non-covalently attached to one another, or are covalently attached to one another. As such, in certain instances, "at least one nucleotide" refers to one or more polynucleotide (e.g., oligonucleotide). In some instances, a polynucleotide is a polymer comprising at least two nucleotide monomeric units.

As used herein, the term "oligonucleotide" refers to a polymer comprising 7-200 nucleotide monomeric units. In some embodiments, "oligonucleotide" encompasses single and or/double stranded RNA as well as single and/or double-stranded DNA. Furthermore, the terms "nucleotide", "nucleic acid," "DNA," "RNA," and/or similar terms include nucleic acid analogs, i.e. analogs having a modified backbone, including but not limited to peptide nucleic acids (PNA), locked nucleic acids (LNA), phosphono-PNA, morpholino nucleic acids, or nucleic acids with modified phosphate groups (e.g., phosphorothioates, phosphonates, 5'-N-phosphoramidite linkages). Nucleotides can be purified from natural sources, produced using recombinant expression systems and optionally purified, chemically synthesized, etc. As used herein, a "nucleoside" is the term describing a compound comprising a monosaccharide and a base. The monosaccharide includes but is not limited to pentose and hexose monosaccharides. The monosaccharide also includes monosaccharide mimetics and monosaccharides modified by substituting hydroxyl groups with halogens, methoxy, hydrogen or amino groups, or by esterification of additional hydroxyl groups. In some embodiments, a nucleotide is or comprises a natural nucleoside phosphate (e.g. adenosine, thymidine, guanosine, cytidine, uridine, deoxyadenosine, deoxythymidine, deoxyguanosine, and deoxycytidine phosphate). In some embodiments, the base includes any bases occurring naturally in various nucleic acids as well as other modifications which mimic or resemble such naturally occurring bases. Nonlimiting examples of modified or derivatized bases include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, 2-aminoadenine, pyrrolopyrimidine, and 2,6-diaminopurine. Nucleoside bases also include universal nucleobases such as difluorotolyl, nitroindolyl, nitropyrrolyl, or nitroimidazolyl. Nucleotides also include nucleotides which harbor a label or contain abasic, i.e., lacking a base, monomers. A nucleic acid sequence is presented in the 5' to 3' direction unless otherwise indicated. A nucleotide can bind to another nucleotide in a sequence-specific manner through hydrogen bonding via Watson-Crick base pairs. Such base pairs are said to be complementary to one another. An oligonucleotide can be single stranded, double-stranded or triple-stranded.

In certain instances, a polymeric carrier (or polymeric material/composition) described herein comprises a plurality of copolymers assembled into a polymeric carrier and, optionally, at least one nucleotide, oligonucleotide, polynucleotide, or the like.

As used herein, normal physiological pH refers to the pH of the predominant fluids of the mammalian body such as blood, serum, the cytosol of normal cells, etc. In certain instances, normal physiologic pH is about neutral pH, including, e.g., a pH of about 7.2 to about 7.4. As used herein, the terms neutral pH, physiologic and physiological pH are synonymous and interchangeable.

RNA interference (RNAi): As used herein, the term "RNA interference" or "RNAi" refers to sequence-specific inhibition of gene expression and/or reduction in target mRNA and protein levels mediated by an at least partially double-stranded RNA, which also comprises a portion that is substantially complementary to a target RNA.

RNAi agent: As used herein, the term "RNAi agent" refers to an oligonucleotide which can mediate inhibition of gene expression through an RNAi mechanism and includes but is not limited to siRNA, microRNA (miRNA), short hairpin RNA (shRNA), asymmetrical interfering RNA (aiRNA), dicer substrate and the precursors thereof.

Short interfering RNA (siRNA): As used herein, the term "short interfering RNA" or "siRNA" refers to an RNAi agent comprising a nucleotide duplex that is approximately 15-50 base pairs in length and optionally further comprises zero to two single-stranded overhangs. One strand of the siRNA includes a portion that hybridizes with a target RNA in a complementary manner. In some embodiments, one or more mismatches between the siRNA and the targeted portion of the target RNA may exist. In some embodiments, siRNAs mediate inhibition of gene expression by causing degradation of target transcripts.

Short hairpin RNA (shRNA): Short hairpin RNA (shRNA) refers to an oligonucleotide having at least two complementary portions hybridized or capable of hybridizing with each other to form a double-stranded (duplex) structure and at least one single-stranded portion. Inhibit gene expression: As used herein, the phrase "inhibit gene expression" means to cause any measurable reduction in the amount of an expression product of the gene. The expression product can be an RNA transcribed from the gene (e.g. an mRNA) and/or a polypeptide translated from an mRNA transcribed from the gene. The level of expression may be determined using standard techniques for measuring mRNA or protein.

Dicer Substrate: a "dicer substrate" is a greater than approximately 25 base pair duplex RNA that is a substrate for the RNase III family member Dicer in cells. Dicer substrates are cleaved to produce approximately 21 base pair duplex small interfering RNAs (siRNAs) that evoke an RNA interference effect resulting in gene silencing by mRNA knockdown.

Therapeutic agent: As used herein, the phrase "therapeutic agent" refers to any agent that, when administered to a subject, organ, tissue, or cell has a therapeutic effect and/or elicits a desired biological and/or pharmacological effect.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Nanoparticle: As used herein, the term "nanoparticle" refers to any particle having a diameter of less than 1000 nanometers (nm). In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g. having diameters of about 10 nm to about 200 nm, about 20 nm to about 100 nm, or 50 nm or less, e.g., 5 nm-30 nm, are used in some embodiments.

As used herein, a "micelle" includes a particle comprising a core and a hydrophilic shell, wherein the core is held together at least partially, predominantly or substantially through hydrophobic interactions. In certain instances, as used herein, a "micelle" is a multi-component, nanoparticle comprising at least two domains, the inner domain or core, and the outer domain or shell. The core is at least partially, predominantly or substantially held together by hydrophobic interactions, and is present in the center of the micelle. As used herein, the "shell of a micelle" is defined as non-core portion of the micelle.

Anionic monomer: "Anionic monomer" or "anionic monomeric unit", as used herein, is a monomer or monomeric unit bearing a group that is present in an anionic charged state or in a non-charged state, but in the non-charged state is capable of becoming anionic charged, e.g., upon removal of an electrophile (e.g., a proton (H+), for example in a pH dependent manner). In certain instances, the group is substantially negatively charged at an approximately physiological pH but undergoes protonation and becomes substantially neutral at a weakly acidic pH. The non-limiting examples of such groups include carboxyl groups, barbituric acid and derivatives thereof, xanthine and derivatives thereof, boronic acids, phosphinic acids, phosphonic acids, sulfinic acids, phosphates, and sulfonamides.

Anionic species: "Anionic species", as used herein, is a group, residue or molecule that is present in an anionic charged state at about neutral (e.g., about 7, such as about 7.2 to about 7.4) or physiologic pH but undergoes protonation and becomes substantially neutral at a weakly acidic pH.

Without being bound by theory not expressly recited in the claims, a membrane destabilizing polymer can directly or indirectly elicit a change (e.g., a permeability change) in a cellular membrane structure (e.g., an endosomal membrane) so as to permit an agent (e.g., polynucleotide), in association with or independent of a polymeric carrier (or a constituent polymer thereof), to pass through such membrane structure—for example to enter a cell or to exit a cellular vesicle (e.g., an endosome). A membrane destabilizing polymer can be (but is not necessarily) a membrane disruptive polymer. A membrane disruptive polymer can directly or indirectly elicit lysis of a cellular vesicle or disruption of a cellular membrane (e.g., as observed for a substantial fraction of a population of cellular membranes).

Generally, membrane destabilizing or membrane disruptive properties of polymers or polymeric carriers can be assessed by various means. In one non-limiting approach, a change in a cellular membrane structure can be observed by assessment in assays that measure (directly or indirectly) release of an agent (e.g., polynucleotide) from cellular membranes (e.g., endosomal membranes)—for example, by determining the presence or absence of such agent, or an activity of such agent, in an environment external to such membrane. Another non-limiting approach involves measuring red blood cell lysis (hemolysis)—e.g., as a surrogate assay for a cellular membrane of interest. Such assays may be done at a single pH value or over a range of pH values.

Hydrophobic species: "hydrophobic species" (used interchangeably herein with "hydrophobicity-enhancing moiety"), as used herein, is a moiety such as a substituent, residue or a group which, when covalently attached to a molecule, such as a monomer or a polymer, increases the molecule's hydrophobicity or serves as a hydrophobicity enhancing moiety.

The term "hydrophobicity" is a term of art describing a physical property of a compound measured by the free energy of transfer of the compound between a non-polar solvent and water (Hydrophobicity regained. Karplus P. A., *Protein Sci.*, 1997, 6: 1302-1307.) A compound's hydrophobicity can be measured by its log P value, the logarithm of a partition coefficient (P), which is defined as the ratio of concentrations of a compound in the two phases of a mixture of two immiscible solvents, e.g. octanol and water. Experimental methods of determination of hydrophobicity as well as methods of computer-assisted calculation of log P values are known to those skilled in the art. Hydrophobic species of the present invention include but are not limited to aliphatic, heteroaliphatic, aryl, and heteroaryl groups.

Aliphatic or aliphatic group: the term "aliphatic" or "aliphatic group", as used herein, means a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms.

Heteroatom: the term "heteroatom" means an atom other than hydrogen or carbon, such as oxygen, sulfur, nitrogen, phosphorus, boron, arsenic, selenium or silicon atom.

Aryl or aryl group: as used herein, the term "aryl" or "aryl group" refers to monocyclic, bicyclic, and tricyclic ring systems having a total of five to fourteen ring members, wherein at least one ring in the system is aromatic and wherein each ring in the system contains three to seven ring members.

Heteroalkyl: the term "heteroalkyl" means an alkyl group wherein at least one of the backbone carbon atoms is replaced with a heteroatom.

Heteroaryl: the term "heteroaryl" means an aryl group wherein at least one of the ring members is a heteroatom.

The following examples are for illustration purposes and are not to be construed as limiting the invention. All publications recited herein are hereby incorporated by reference for the information to which the publications are cited.

EXAMPLES

Throughout the description of the present invention, various known acronyms and abbreviations are used to describe monomers or monomeric residues derived from polymerization of such monomers. Without limitation, unless otherwise noted: "BMA" (or the letter "B" as equivalent shorthand notation) represents butyl methacrylate or monomeric residue derived therefrom; "DMAEMA" (or the letter "D" as equivalent shorthand notation) represents N,N-dimethylaminoethyl methacrylate or monomeric residue derived therefrom; "Gal" refers to galactose or a galactose residue, optionally including hydroxyl-protecting moieties (e.g., acetyl) or to a pegylated derivative thereof (as described below); HPMA represents 2-hydroxypropyl methacrylate or monomeric residue derived therefrom; "MAA" represents methylacrylic acid or monomeric residue derived therefrom; "MAA(NHS)" represents N-hydroxyl-succinimide ester of methacrylic acid or monomeric residue derived therefrom; "PAA" (or the letter "P" as equivalent shorthand notation) represents 2-propylacrylic acid or monomeric residue derived therefrom, "PEGMA" refers to the pegylated methacrylic monomer, $CH_3O(CH_2O)_{7-8}OC(O)C(CH_3)CH_2$ or monomeric residue derived therefrom. In each case, any such designation indicates the monomer (including all salts, or ionic analogs thereof), or a monomeric residue derived from polymerization of the monomer (including all salts or ionic analogs thereof), and the specific indicated form is evident by context to a person of skill in the art.

Example 1

Preparation of Copolymers

Di-block polymers and copolymers of the following general formula are prepared:

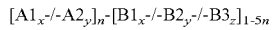

Where [A1-A2] is the first block copolymer, composed of residues of monomers A1 and A2 [B1-B2-B3] is the second block copolymer, composed of residues of monomers B1, B2, B3 x, y, z is the polymer composition in mole % monomer residue n is molecular weight Exemplary di-block copolymers:

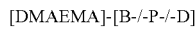

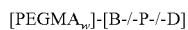

[PEGMA$_w$-DMAEMA]-[B-/-P-/-D]

Where:
B is butyl methacrylate
P is propyl acrylic acid
D is DMAEMA is dimethylaminoethyl methacrylate
PEGMA is polyethyleneglycol methacrylate where, for example, w=4-5 or 7-8 ethylene oxide units)
MAA(NHS) is methylacrylic acid-N-hydroxy succinimide
HPMA is N-(2-hydroxypropyl)methacrylamide
PDSM is pyridyl disulfide methacrylate These polymers represent structures where the composition of the first block of the polymer or copolymer is varied or chemically treated in order to create polymers where the first block is neutral (e.g., PEGMA), cationic (DMAEMA), anionic (PEGMA-NHS, where the NHS is hydrolyzed to the acid), ampholytic (DMAEMA-NHS, where the NHS is hydrolyzed to the acid), or zwitterrionic (for example, poly[2-methacryloyloxy-2' trimethylammoniumethyl phosphate]). In addition, the [PEGMA-PDSM]-[B-P-D] polymer contains a pyridyl disulfide functionality in the first block that can be reacted with a thiolated siRNA to form a polymer-siRNA conjugate.

Example 1.1

Synthesis of Block Copolymer Using RAFT Polymerization

A. RAFT Chain Transfer Agent.

The synthesis of the chain transfer agent (CTA), 4-Cyano-4-(ethylsulfanylthiocarbonyl) sulfanylpentanoic acid (ECT), utilized for the following RAFT polymerizations, was adapted from a procedure by Moad et al., *Polymer*, 2005, 46(19): 8458-68. Briefly, ethane thiol (4.72 g, 76 mmol) was added over 10 minutes to a stirred suspension of sodium hydride (60% in oil) (3.15 g, 79 mmol) in diethyl ether (150 ml) at 0° C. The solution was then allowed to stir for 10 minutes prior to the addition of carbon disulfide (6.0 g, 79 mmol). Crude sodium S-ethyl trithiocarbonate (7.85 g, 0.049 mol) was collected by filtration, suspended in diethyl ether (100 mL), and reacted with Iodine (6.3 g, 0.025 mol). After 1 hour the solution was filtered, washed with aqueous sodium thiosulfate, and dried over sodium sulfate. The crude bis (ethylsulfanylthiocarbonyl) disulfide was then isolated by rotary evaporation. A solution of bis-(ethylsulfanylthiocarbonyl) disulfide (1.37 g, 0.005 mol) and 4,4'-azobis(4-cyanopentanoic acid) (2.10 g, 0.0075 mol) in ethyl acetate (50 mL) was heated at reflux for 18 h. Following rotary evaporation of the solvent, the crude 4-Cyano-4 (ethylsulfanylthiocarbonyl) sulfanylvpentanoic acid (ECT) was isolated by column chromatography using silica gel as the stationary phase and 50:50 ethyl acetate hexane as the eluent.

B. Poly(N,N-dimethylaminoethyl Methacrylate) Macro Chain Transfer Agent (polyDMAEMA macroCTA).

The RAFT polymerization of DMAEMA was conducted in DMF at 30° C. under a nitrogen atmosphere for 18 hours using ECT and 2,2'-Azobis(4-methoxy-2.4-dimethyl valeronitrile) (V-70) (Wako chemicals) as the radical initiator. The initial monomer to CTA ratio ($[CTA]_0/[M]_0$ was such that the theoretical $M_n$ at 100% conversion was 10,000 (g/mol). The initial CTA to initiator ratio ($[CTA]_o/[I]_o$) was 10 to 1. The resultant polyDMAEMA macro chain transfer agent was isolated by precipitation into 50:50 v:v diethyl ether/pentane. The resultant polymer was redissolved in acetone and subsequently precipitated into pentane (×3) and dried overnight in vacuo.

C. Block Copolymerization of DMAEMA, PAA, and BMA from a poly(DMAMEA) macroCTA.

The desired stoichiometric quantities of DMAEMA, PAA, and BMA were added to poly(DMAEMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of V70 the solutions were purged with nitrogen for 30 min and allowed to react at 30° C. for 18 h. The resultant diblock copolymers were isolated by precipitation into 50:50 v:v diethyl ether/pentane. The precipitated polymers were then redissolved in acetone and subsequently precipitated into pentane (×3) and dried overnight in vacuo. Gel permeation chromatography (GPC) was used to determine molecular weights and polydispersities (PDI, $M_w/M_n$) of both the poly(DMAEMA) macroCTA and diblock copolymer samples in DMF with respect to polymethyl methacrylate standards (SEC Tosoh TSK-GEL R-3000 and R-4000 columns (Tosoh Bioscience, Montgomeryville, Pa.) connected in series to a Viscotek GPCmax VE2001 and refractometer VE3580 (Viscotek, Houston, Tex.). HPLC-grade DMF containing 1.0 wt % LiBr was used as the mobile phase. FIG. 1A summarizes the molecular weights, compositions, and block ratios of some of the RAFT synthesized polymers.

Example 1.2

Preparation of Second Block (B1-B2-B3) Copolymerization of DMAEMA, PAA, and BMA from a Poly(PEGMA) MacroCTA The desired stoichiometric quantities of DMAEMA, PAA, and BMA were added to poly(PEGMA) macroCTA dissolved in N,N-dimethylformamide (25 wt % monomer and macroCTA to solvent). For all polymerizations $[M]_o/[CTA]_o$ and $[CTA]_o/[I]_o$ were 250:1 and 10:1 respectively. Following the addition of AIBN the solutions were purged with nitrogen for 30 min and allowed to react at 68° C. for 6-12 h. The resulting diblock copolymers were isolated by precipitation into 50:50 v:v diethyl ether/pentane. The precipitated polymers were then redissolved in acetone and subsequently precipitated into pentane (×3) and dried overnight in vacuo. Gel permeation chromatography (GPC) was used to determine molecular weights and polydispersities (PDI, $M_w/M_n$) of both the poly(PEGMA) macroCTA and diblock copolymer samples in DMF using a Viscotek GPCmax VE2001 and refractometer VE3580 (Viscotek, Houston, Tex.). HPLC-grade DMF containing 1.0 wt % LiBr was used as the mobile phase. NMR spectroscopy in $CDCl_3$ was used to confirm the polymer structure and calculate the composition of the $2^{nd}$ block.

Example 1.3

Preparation and Characterization of PEGMA-DMAEMA Co-polymers

Polymer synthesis was carried out using a procedure similar to that described in Examples 1.1 and 1.2. The ratio of the PEGM and DMAEMA in the first block was varied by using different feed ratios of the individual monomers to create the co-polymers described in FIG. 1B.

Example 1.4

Preparation and Characterization of PEGMA-MAA(NHS) Co-polymers

Polymer synthesis was performed as described in Examples 1.1 and 1.2, using monomer feed ratios to obtain the desired composition of the $1^{st}$ block copolymer. In some instances, [PEGMA$_w$-MAA(NHS)]-[B-P-D] polymer is prepared where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 1.5

Preparation and Characterization of DMAEMA-MAA(NHS) Co-polymers

Polymer synthesis was performed as described in Examples 1.1 and 1.2, using monomer feed ratios to obtain the desired composition of the $1^{st}$ block copolymer. In certain instances, [DMAEMA-MAA(NHS)]-[B-P-D] polymer is prepared where the co-polymer ratio of monomers in the $1^{st}$ block is 70:30. NHS containing polymers can be incubated in aqueous buffer (phosphate or bicarbonate) at pH between 7.4 and 8.5 for 1-4 hrs at room temperature or 37° C. to generate the hydrolyzed (acidic) form.

Example 2

Preparation and Characterization of HPMA-PDS(RNA) Co-polymer Conjugates for siRNA Drug Delivery A. Synthesis of Pyridyl Disulfide Methacrylate Monomer (PDSMA).

Aldrithiol-2™ (5 g, 22.59 mmol) was dissolved in 40 ml of methanol and 1.8 ml of AcOH. The solution was added as a solution of 2-aminoethanethiol.HCl (1.28 g, 11.30 mmol) in 20 ml methanol over 30 min. The reaction was stirred under $N_2$ for 48 h at R.T. After evaporation of solvents, the residual oil was washed twice with 40 ml of diethyl ether. The crude compound was dissolved in 10 ml of methanol and the product was precipitated twice with 50 ml of diethyl ether to get the desired compound 1 as slight yellow solid. Yield: 95%.

Pyridine dithioethylamine (6.7 g, 30.07 mmol) and triethylamine (4.23 ml, 30.37 mmol) were dissolved in DMF (25 ml) and pyridine (25 ml) and methacryloyl chloride (3.33 ml, 33.08 mmol) was added slowly via syringe at 0 C. The reaction mixture was stirred for 2 h at R.T. After reaction, the reaction was quenched by sat. $NaHCO_3$ (350 ml) and extracted by ethyl acetate (350 ml). The combined organic layer was further washed by 10% HCl (100 ml, 1 time) and pure water (100 ml, 2 times) and dried by $MaSO_4$. The pure product was purified by column chromatography (EA/Hex: 1/10 to 2/1) as yellow syrup. Rf=0.28 (EA/Hex=1/1). Yield: 55%.

B. HPMA-PDSMA Co-polymer Synthesis

The RAFT polymerization of N-(2-hydroxypropyl)methacrylamide (HPMA) and pyridyl disulfide methacrylate (typically at a 70:30 monomer ratio) is conducted in DMF (50 weight percent monomer:solvent) at 68° C. under a nitrogen atmosphere for 8 hours using 2,2'-azo-bis-isobutyrylnitrile (AIBN) as the free radical initiator. The molar ratio of CTA to AIBN is 10 to 1 and the monomer to CTA ratio is set so that a molecular weight of 25,000 g/mol would be achieved if at 100% conversion. The poly(HPMA-PDS) macro-CTA was isolated by repeated precipitation into diethyl ether from methanol.

The macro-CTA is dried under vacuum for 24 hours and then used for block copolymerization of dimethylaminoethyl methacrylate (DMAEMA), propylacrylic acid (PAA), and butyl methacrylate (BMA). Equimolar quantities of DMAEMA, PAA, and BMA ($[M]_o/[CTA]_o$=250) are added to the HPMA-PDS macroCTA dissolved in N,N-dimethylformamide (25 wt % monomer and macroCTA to solvent). The radical initiator AIBN is added with a CTA to initiator ratio of 10 to 1. The polymerization is allowed to proceed under a nitrogen atmosphere for 8 hours at 68° C. Afterwards, the resultant diblock polymer is isolated by precipitation 4 times into 50:50 diethyl ether/pentane, redissolving in ethanol between precipitations. The product is then washed 1 time with diethyl ether and dried overnight in vacuo.

C. siRNA Conjugation to HPMA-PDSMA Co-polymer

Thiolated siRNA was obtained commercially (Agilent, Boulder, Colo.) as a duplex RNA with a disulfide modified 5'-sense strand. The free thiol form for conjugation is prepared by dissolving the lyophilized compound in water and treated for 1 hour with the disulfide reducing agent TCEP immobilized within an agarose gel. The reduced RNA (400 µM) was then reacted for 24 hours with the pyridyl disulfide-functionalized polymer in phosphate buffer (pH 7) containing 5 mM ethylenediaminetetraacetic acid (EDTA).

The reaction of the pyridyl disulfide polymer with the RNA thiol creates 2-pyridinethione, which can be spectrophotometrically measured to characterize conjugation efficiency. To further validate disulfide exchange, the conjugates are run on an SDS-PAGE 16.5% tricine gel. In parallel, aliquots of the conjugation reactions are treated with immobilized TCEP prior to SDS-PAGE to verify release of the RNA from the polymer in a reducing environment. Conjugation reactions are conducted at polymer/RNA stoichiometries of 1, 2, and 5. UV spectrophotometric absorbance measurements at 343 nm for 2-pyridinethione release are used to measure conjugation efficiencies.

Example 3

Synthesis of Polymers with Cell Targeting Agents:
Click Reaction of Azido-terminated Polymer with
Propargyl Folate A combination of controlled radical polymerization and azide-alkyne click chemistry is used to prepare block copolymer micelles conjugated with biological ligands (for example, folate) with potential for active targeting of specific tissues/cells containing the specific receptor of interest (for example, folate). Block copolymers are synthesized by reversible addition-fragmentation chain transfer (RAFT) polymerization as described in Example 1, except that an azido chain transfer agent (CTA) is used. The azido terminus of the polymer is then reacted with the alkyne derivative of the targeting agent (for example, folate) to produce the polymer containing the targeting agent.

Synthesis of the RAFT Agent.

The RAFT chain transfer agent (CTA) 2-dodecylsulfanylthiocarbonylsulfanyl-2-methyl-propionic acid 3-azidopropyl ester (C12-CTAN3) is prepared as follows:

Synthesis of 3-Azidopropanol. 3-Chloro-1-propanol (5.0 g, 53 mmol, 1.0 equiv) and sodium azide (8.59 g, 132 mmol, 2.5 equiv) are reacted in DMF (26.5 mL) at 100° C. for 48 h. The reaction mixture is cooled to room temperature, poured into ethyl ether (200 mL), and extracted with a saturated aqueous NaCl solution (500 mL). The organic layer is separated, dried over MgSO4, and filtered. The supernatant is concentrated to obtain the product (5.1 g, 95% yield).

Synthesis of 2-dodecylsulfanylthiocarbonylsulfanyl-2-methylpropionic acid chloride (DMP-Cl). 2-dodecylsulfanylthiocarbonylsulfanyl-2-methyl-propionic acid (DMP, Noveon>95%) (1.0 g, 2.7 mmol, 1.0 equiv) is dissolved in methylene chloride (15 mL) in a 50 mL round-bottom flask, and the solution is cooled to approximately 0° C. Oxalyl chloride (0.417 g, 3.3 mmol, 1.2 equiv) is added slowly under a nitrogen atmosphere, and the solution is allowed to reach room temperature and stirred for a total of 3 h. The resulting solution is concentrated under reduced pressure to yield the acid chloride product (1.0 g, 99% yield).

Synthesis of 2-dodecylsulfanylthiocarbonylsulfanyl-2-methylpropionic acid 3-azidopropyl ester. 3-Azidopropanol (265 mg, 2.62 mmol, 1.0 equiv) is dissolved in methylene chloride (5 mL) in a 50 mL round-bottom flask, and the solution is cooled to approximately 0° C. A solution of triethylamine (0.73 mL) in methylene chloride (5 mL) is added dropwise over 10 min. A solution of DMP-Cl (1.0 g, 2.6 mmol) in methylene chloride (5 mL) is added dropwise, and the solution is allowed to reach room temperature while stirring for 3 h. The solution is concentrated under reduced pressure, diluted with ethyl ether (100 mL), and washed with saturated aqueous sodium bicarbonate solution (50 mL), water (50 mL), and saturated NaCl solution (50 mL), successively. The organic layer is separated, dried over MgSO4 (1.0 g), and filtered. The supernatant is concentrated under reduced pressure to yield the product (1.05 g, 90% yield) as a residual oil.

Synthesis of Propargyl Folate.

Folic acid (1.0 g, 0.0022 mol) is dissolved in DMF (10 mL) and cooled in a water/ice bath. N-Hydroxysuccinimide (260 mg, 0.0025 mol) and EDC (440 mg, 0.0025 mol) are added, and the resulting mixture is stirred in an ice bath for 30 min to give a white precipitate. A solution of propargylamine (124 mg, 2.25 mmol) in DMF (5.0 mL) is added, and the resulting mixture is allowed to warm to room temperature and stirred for 24 h. The reaction mixture is poured into water (100 mL)

and stirred for 30 min to form a precipitate. The orange-yellow precipitate is filtered, washed with acetone, and dried under vacuum for 6 h to yield 1.01 g of product (93% yield).

Click Reaction of Azido-terminated Polymers with Propargyl Folate.

The azido-terminated polymer is reacted with propargyl folate by the following example procedure. A solution of N3-α-[$D_s$-$X_t$]$_b$-[$B_x$-$P_y$-$D_z$]$_a$-ω (0.0800 mmol) in DMF (7 mL), and pentamethyldiethylenetriamine (PMDETA, Aldrich, 99%), (8.7 mg, 0.050 mmol) is purged with nitrogen for 60 min and transferred via syringe to a vial equipped with a magnetic stir bar containing CuBr (7.2 mg, 0.050 mmol) and propargyl folate (42 mg, 0.088 mmol) under a nitrogen atmosphere. The reaction mixture is stirred at 26° C. for 22 h in the absence of oxygen. The reaction mixture is exposed to air, and the solution is passed through a column of neutral alumina. DMF is removed under vacuum, and the product is precipitated into hexanes. The resulting folate-terminated block copolymer folate-α-[$D_s$-$X_t$]$_b$-[$B_x$-$P_y$-$D_z$]$_a$-ω is dissolved in THF and filtered to remove excess propargyl folate. THF is removed, and then the polymer is dissolved in deionized (DI) water and dialyzed for 6 h using a membrane with a molecular weight cutoff of 1000 Da. The polymer is isolated by lyophilization.

Example 4

NMR Spectroscopy of Block Copolymer PRx0729v6 (Also Known as P7v6). (FIG. 2)

This example provides evidence, using NMR spectroscopy, that polymer PRx0729v6 forms a micelle-like structure in aqueous solution.

$^1$H NMR spectra were recorded on Bruker AV301 in deuterated chloroform (CDCl$_3$) and deuterated water (D$_2$O) at 25° C. A deuterium lock (CDCl$_3$, D$_2$O) was used, and chemical shifts were determined in ppm from tetramethylsilane (for CDCl$_3$) and 3-(trimethylsilyl)propionic-2,2,3,3-d4 acid, sodium salt (for D$_2$O). Polymer concentration was 6 mg/ml.

NMR spectroscopy of the synthesized polymer, using polymer PRx0729v6 as an example, in aqueous buffer provided evidence that the diblock polymers of the present invention form micelles in aqueous solution. Formation of micelles results in the formation of a shielded viscous internal core that restricts the motion of the protons forming the core segments and prevents deuterium exchange between the solvent and the protons of the core. This is reflected by a significance suppression or disappearance of the $^1$H NMR signals of the corresponding protons. We used this inherent property of solution NMR spectroscopy to show that the hydrophobic block of the core of the micelle is effectively shielded. If micelles are formed in aqueous media, a disappearance of the signals due to the protons of the hydrophobic copolymer block should occur.

Figure 2B:
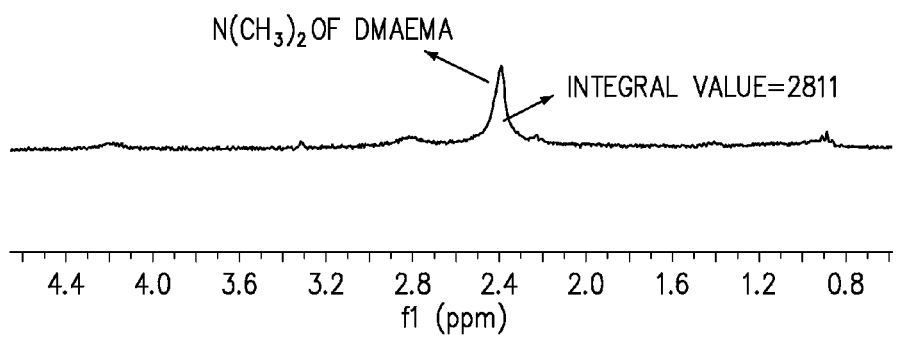

FIG. 2 shows the $^1$H NMR experiments of polymer PRx0729v6 in CDCl$_3$ (organic solvent) and D$_2$O (aqueous solvent). The $^1$H NMR spectrum of polymer in CDCl$_3$ at room temperature (FIG. 2A) shows the signals attributed to all polymer protons indicating that the polymer chains remain dispersed (non-aggregated) in CDCl$_3$ and preserve their motion so their protons can exchange with the solvent. This indicates that stable micelles with shielded cores are not formed from PRx0729v6 in organic solvent. FIG. 2B shows the $^1$H NMR spectra of PRx0729v6 in D$_2$O. The signals representing the protons of the hydrophobic block (BMA, PAA, DMAEMA) disappear from the spectrum. This indicates that stable micelles with shielded cores are formed from PRx0729v6 in aqueous solution. Moreover, in the same spectrum, the signal attributed to the resonance of the protons of the two methyl groups of the DMAEMA (2.28 ppm) undergoes a significant suppression, implying that only the first poly DMAEMA block constituting the shell is exposed to water, i.e., mainly the charged group of DMAEMA. A simple calculation indicates that the integrated percentage of PAA, DMAEMA of the hydrophobic block (2900) subtracted from the signal in CDCl$_3$ (5600) gives the approximate value for the same signal in D$_2$O (2811), consistent with this conclusion.

Taken together, the results of $^1$H NMR experiments indicate that polymer PRx0729v6 forms micelles with an ordered core-shell structure where the first block polyDMAEMA forms a hydrated outer shell surrounding a core composed of hydrophobic units (BMA) and electrostatically stabilizing units of opposite charge (PAA, DMAEMA).

Example 5

Dynamic Light Scattering (DLS) Determination of Particle Size of Polymer PRx0729v6 Complexed to siRNA. (FIG. 3)

The following example demonstrates that polymer PRx0729v6 forms uniform particles 45 nm in size either alone or 47 nm in size following binding to siRNA.

Particle sizes of polymer alone or polymer/siRNA complexes were measured by dynamic light scattering (DLS) using a Malvern Zetasizer Nano ZS. Lyophilized polymer was dissolved in 100% ethanol at 10-50 mg/ml, then diluted 10-fold into phosphate buffer, pH 7.4. Polymers were measured in phosphate buffered saline, pH 7.4 (PBS) at 1 mg/ml for PRx0729v6 alone or at 0.7 mg/ml PRx0729v6 complexed to 1 uM GAPDH-specific 21 mer-siRNA (Ambion), with a theoretical charge ratio of 4:1, positive charges on polymer:negative charges on siRNA. PRx0729v6 alone (45 nm) and PRx0729v6 complexed to siRNA (47 nm) (FIG. 3) show similar particle sizes with a near uniform distribution, PDI<0.1.

Example 6

Figure 4:
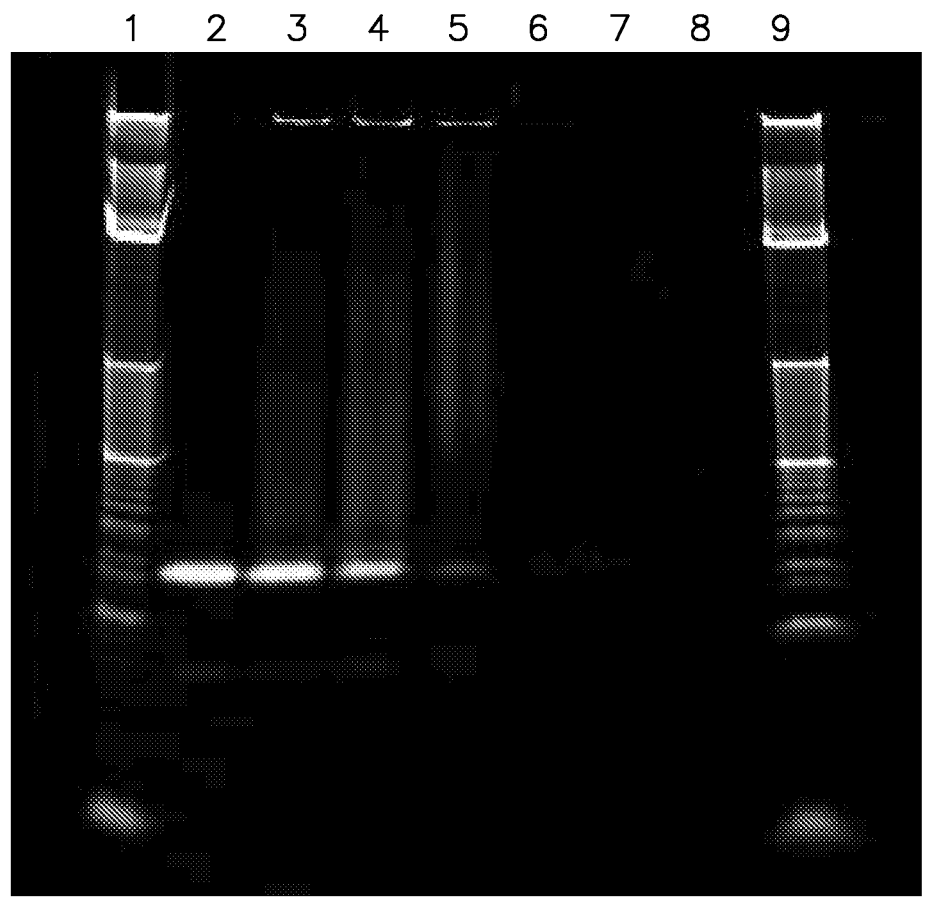
FIG. 4: An illustrative example of the gel shift analysis of polymer PRx0729v6/siRNA complexes at different charge ratios.

Gel Shift Analysis of Polymer PRx0729v6/siRNA Complexes at Different Charge Ratios. (FIG. 4)

The following example demonstrates that polymer PRx0729v6 binds to siRNA at various charge ratios resulting in a complex with reduced electrophoretic mobility.

Polymer siRNA binding was analyzed by gel electrophoresis (FIG. 4) and demonstrates that complete siRNA binding to polymer occurs at a polymer/siRNA charge ratio of 4:1 and higher.

Example 7

Figure 5:
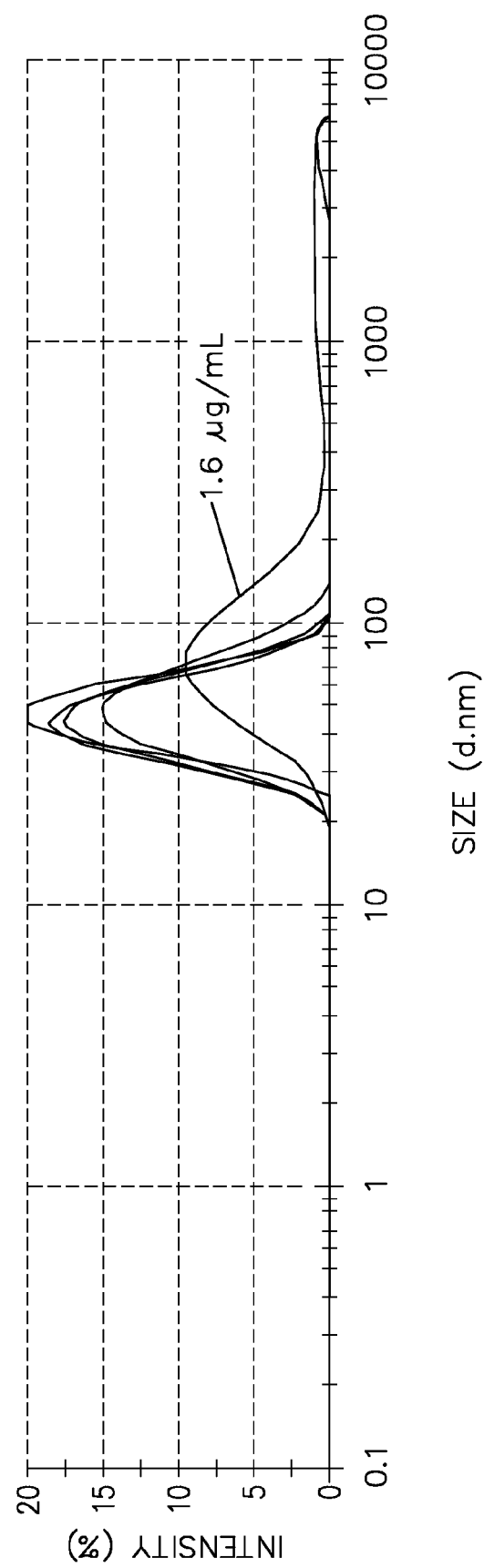
FIG. 5: An illustrative example of the critical stability concentration (CSC) of polymer PRx0729v6.

Critical Micelle Concentration (CMC) of Polymer PRx0729v6. (FIG. 5)

The following example demonstrates that micelles formed by polymer PRx0729v6 are stable to 100-fold dilution.

Particle sizes of polymer PRx0729v6 in PBS buffer pH 7.4 at a concentration of 1 mg/ml±0.5 M NaCl. Particle size was measured by dynamic light scattering over a 5-fold range of serial dilutions from 1 mg/ml to 1.6 ug/ml with PBS±0.5 M NaCl. FIG. 5 shows that a particle size of about 45 nm is stable down to a concentration of about 10 ug/ml. Polymer PRx0729v6 appears to be unstable below about 5 ug/ml (the CMC) where individual polymer chains dissociate and form non-specific aggregates.

Example 8

Figure 6:
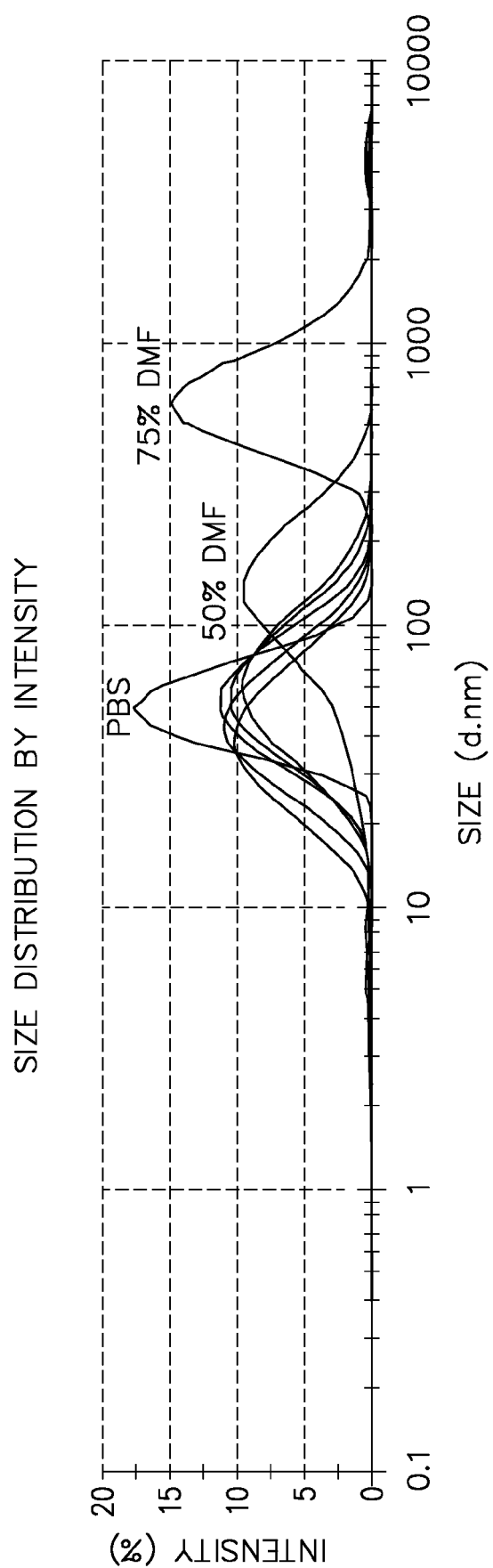
FIG. 6: An illustrative example of the polymer PRx0729v6 particle stability in organic solvents.

Polymer PRx0729v6 Particle Stability in Organic Solvents. (FIG. 6)

This example demonstrates that the micelle structure of polymer PRx0729v6 is dissociated in organic solvents, consistent with the hydrophobic nature of the micelle core.

Polymer PRx0729v6 was dissolved in various organic solvents at a concentration of 1 mg/ml and particle size was measured by dynamic light scattering. FIG. 6 shows that increasing concentration of dimethylformamide (DMF) results in micelle dissociation to aggregated chains.

Example 9

Knock-Down Activity of siRNA—Micelle Complexes in Cultured Mammalian Cells. (FIG. 7 and FIG. 12)

Knock-down (KD) activity of siRNA/polymer PRx0729v6 complexes was assayed in 96-well format by measuring specific gene expression after 24 hours of treatment with PRx0729v6:siRNA complexes. Polymer and GAPDH targeting siRNA or negative control siRNA (Ambion) were mixed in 25 uL to obtain various charge ratios and concentrations at 5-fold over final transfection concentration and allowed to complex for 30 minutes before addition to HeLa cells in 100 uL normal media containing 10% FBS. Final siRNA concentrations were evaluated at 100, 50, 25, and 12.5 nM. Polymer was added either at 4:1, 2:1 or 1:1 charge ratios, or at fixed polymer concentrations of 18, 9, 4.5, and 2.2 ug/ml to determine what conditions result in highest KD activity. For charge ratios (FIG. 7A), the complexes were prepared at higher concentrations, incubated for 30 minutes, and then serial diluted at 5-fold over concentration shown on graphs just prior to addition to cells. For fixed polymer concentration (FIG. 7B), the siRNA and polymer were complexed at 5-fold over concentrations shown on the graph, incubated for 30 minutes then added to cells for final concentrations shown in FIG. 7. FIG. 7C is the negative control. Total RNA was isolated 24 hours post treatment and GAPDH expression was measured relative to 2 internal normalizer genes, RPL13A and HPRT, by quantitative PCR. Results in FIG. 7 and FIG. 12A and FIG. 12B indicate >60% KD activity (shading) obtained with PRx0729v6 at 9 ug/ml and higher concentrations at all siRNA concentrations tested. This concentration was coincident with stable micelle formation from particle size analyses. High KD activity was observed with 4.5 ug/ml PRx0729v6/12.5 nM siRNA only when complexes were prepared at high concentration and serial diluted (4:1 charge ratio) as compared to complex formation at lower concentration (4.5 ug/ml fixed polymer concentration). Additionally, only 100 nM siRNA with 4.5 ug/ml PRx0729v6 showed high KD activity whereas lower siRNA concentrations did not. In summary, PRx0729v6 micelles were stable to dilution down to ~10 ug/ml and KD activity is lost below ~5 ug/ml, indicating that stable micelles are required for good KD activity.

Example 10

Knock-down Activity of Dicer Substrate GAPDH siRNA-polymer Complexes in Cultured Mammalian Cells Knock-down (KD) activity of GAPDH specific dicer substrate siRNA/polymer complexes is assayed in a 96-well format by measuring GAPDH gene expression after 24 hours of treatment with polymer: GAPDH dicer siRNA complexes. The GAPDH dicer siRNA sequence is: sense strand: rGrGrU-rCrArUrCrCrArUrGrArCrArArCrUrUrGrGrUrAdTdC, [SEQ ID NO:1], antisense strand: rGrArUrArCrCrArArAr-GrUrUrGrUrCrArUrGrGrArUrGrArCrCrUrU [SEQ ID NO: 2]. Polymer and GAPDH targeting siRNA or negative control siRNA (IDT) are mixed in 25 uL to obtain various charge ratios and concentrations at 5-fold over final transfection concentration and allowed to complex for 30 minutes before addition to HeLa cells in 100 uL normal media containing 10% FBS. Final siRNA concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in highest KD activity. Total RNA is isolated 24 hours post treatment and GAPDH expression is measured relative to 2 internal normalizer genes, RPL13A and HPRT, by quantitative PCR. Results show >60% KD activity obtained with polymer at 10 ug/ml and higher concentrations at all siRNA concentrations tested. This polymer concentration is coincident with stable micelle formation from particle size analyses.

Example 11

Knock-down Activity of ApoB100 siRNA-polymer Complexes in Cultured Mammalian Cells Knock-down (KD) activity of ApoB100 specific siRNA or dicer substrate siRNA complexed to polymer is assayed in a 96-well format by evaluating ApoB100 gene expression after 24 hours of treatment with polymer: ApoB siRNA complexes. The ApoB100 siRNA sequence is: sense strand: 5'-rGrArArUrGrUrGrGrGrUrGrGrCrArArCrUrUrUrArG-3', antisense strand: 5'-rArArArGrUrUrGrCrCrArCrCr-CrArCrArUrUrCrArG-3'. The ApoB100 dicer substrate siRNA sequence is: sense strand: 5'-rGrArArUrGrUrGrGrGr-GrUrGrGrCrArArCrUrUrUrArArArGdGdA, antisense strand: 5'-rUrCrCrUrUrUrArArArGrUrUrGr-CrCrArCrCrCrArCrArUrUrCrArG-3'. Polymer and ApoB targeting siRNA or negative control siRNA (IDT) are mixed in 25 uL to obtain various charge ratios and concentrations at 5-fold over final transfection concentration and allowed to complex for 30 minutes before addition to HepG2 cells in 100 uL normal media containing 10% FBS. Final siRNA concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in highest KD activity. Total RNA is isolated 24 hours post treatment and ApoB100 expression is measured relative to 2 internal normalizer genes, RPL13A and HPRT, by quantitative PCR. Results show >60% KD activity obtained with polymer at 10 ug/ml and higher concentrations at all siRNA concentrations tested. This polymer concentration is coincident with stable micelle formation from particle size analyses.

Example 12

Knock-down Activity of ApoB100 siRNA-polymer Complexes in a Mouse Model

The knockdown activity of ApoB100 specific siRNA/polymer complexes is determined in a mouse model by measuring ApoB100 expression in liver tissue and serum cholesterol levels. Balb/C mice are dosed intravenously via the tail vein with 1, 2 or 5 mg/kg ApoB specific siRNA complexed to polymer at 1:1, 2:1 or 4:1 charge ratio (polymer:siRNA) or saline control. 48 hours post final dose mice are sacrificed and blood and liver samples are isolated. Cholesterol levels are measured in serum. Total RNA is isolated from liver and ApoB100 expression is measured relative to 2 normalizer genes, HPRT and GAPDH by quantitative PCR.

Example 13

Knock-down Activity of ApoB100 Antisense DNA Oligonucleotide-polymer Complexes in Cultured Mammalian Cells Knock-down (KD) capability by ApoB100 specific antisense DNA oligonucleotide complexed to polymer is assayed in a 96-well format by measuring ApoB100 gene expression after 24 hours of treatment with polymer: ApoB antisense DNA oligonucleotide complexes. Two ApoB100 antisense oligonucleotides specific to mouse ApoB are:
(1) 5'-GTCCCTGAAGATGTCAATGC-3', position 541 of the coding region and
(2) 5'-ATGTCAATGCCACATGTCCA-3', position 531 of the coding region Polymer and an ApoB targeting antisense DNA oligonucleotide or negative control DNA oligonucleotide (scrambled sequence) are mixed in 25 uL to obtain various charge ratios and concentrations at 5-fold over final transfection concentration and allowed to complex for 30 minutes before addition to HepG2 cells in 100 uL normal media containing 10% FBS. Final oligonucleotide concentrations are examined at 100, 50, 25, and 12.5 nM. Polymer is added either at 4:1, 2:1 or 1:1 charge ratios, or at fixed polymer concentrations of 40, 20, 10, and 5 ug/ml to determine what condition results in the highest KD activity. Total RNA is isolated 24 hours post treatment and ApoB100 expression is measured relative to 2 internal normalizer genes, RPL13A and HPRT, by quantitative PCR.

Example 14

Figure 8B:
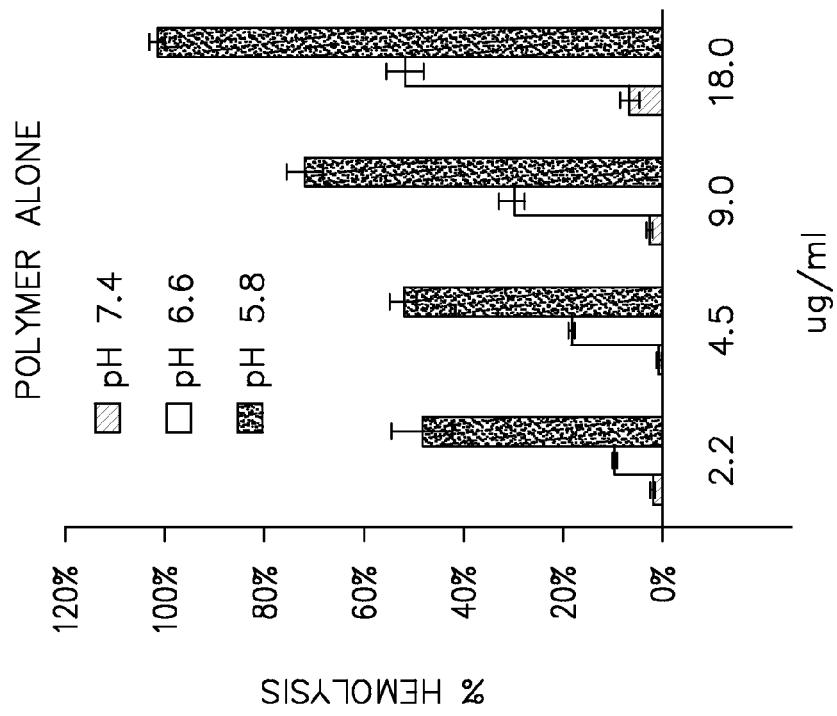
FIG. 8: An illustrative example of the demonstration of membrane destabilizing activity of polymeric micelles and their siRNA complexes
Figure 8A:
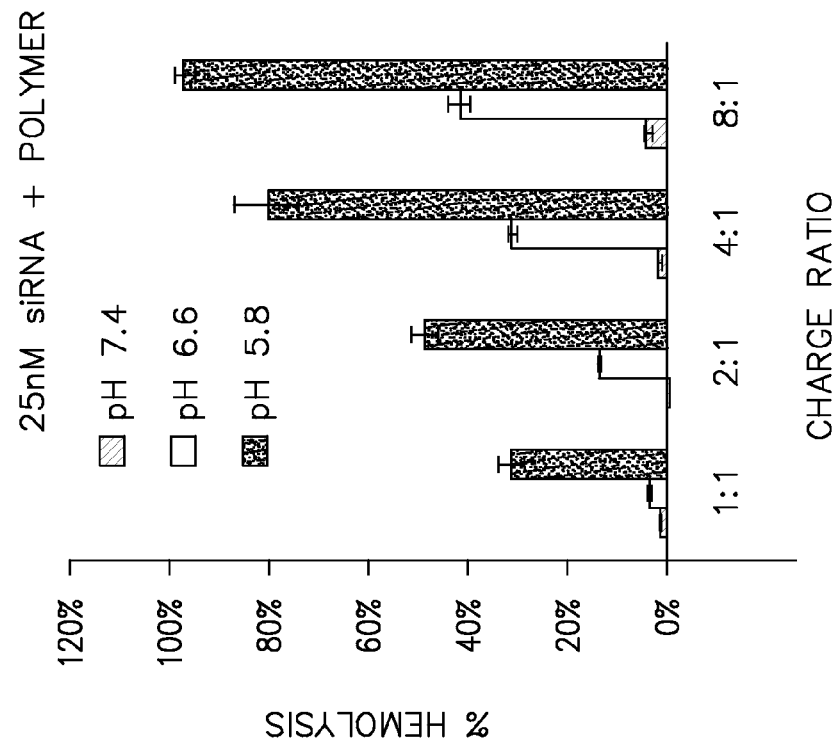

Demonstration of Membrane Destabilizing Activity of Polymeric Micelles and their siRNA Complexes (FIG. 8)

pH responsive membrane destabilizing activity was assayed by titrating polymer alone or PRx0729v6:siRNA complexes into preparations of human red blood cells (RBC) and determining membrane-lytic activity by hemoglobin release (absorbance reading at 540 nm). Three different pH conditions were used to mimic endosomal pH environments (extracellular pH=7.4, early endosome=6.6, late endosome=5.8). Human red blood cells (RBC) were isolated by centrifugation from whole blood collected in vaccutainers containing EDTA. RBC were washed 3 times in normal saline, and brought to a final concentration of 2% RBC in PBS at specific pH (5.8, 6.6 or 7.4). PRx0729v6 alone or PRx0729v6/siRNA complex was tested at concentrations just above and below the critical micelle concentration (CMC) as shown (FIG. 5). For polymer/siRNA complex, 25 nM siRNA was added to PRx0729v6 at 1:1, 2:1, 4:1 and 8:1 charge ratios (same polymer concentrations for polymer alone). Solutions of polymer alone or polymer-siRNA complexes were formed at 20× final assayed concentration for 30 minutes and diluted into each RBC preparation. Two different preparations of PRx0729v6 polymer stock were compared for stability of activity at 9 and 15 days post preparation, stored at 4° C. from day of preparation. RBC with polymer alone or polymer/siRNA complex were incubated at 37° C. for 60 minutes and centrifuged to remove intact RBC. Supernatants were transferred to cuvettes and absorbance determined at 540 nm. Percent hemolysis is expressed as $A_{540}$ sample/$A_{540}$ of 1% Triton X-100 treated RBC (control for 100% Lysis). The results show that PRx0729v6 alone (FIG. 8A) or PRx0729v6/siRNA complex (FIG. 8B) is non-hemolytic at pH 7.4 and becomes increasingly more hemolytic at the lower pH values associated with endosomes and at higher concentrations of polymer.

Example 15

Figure 9:
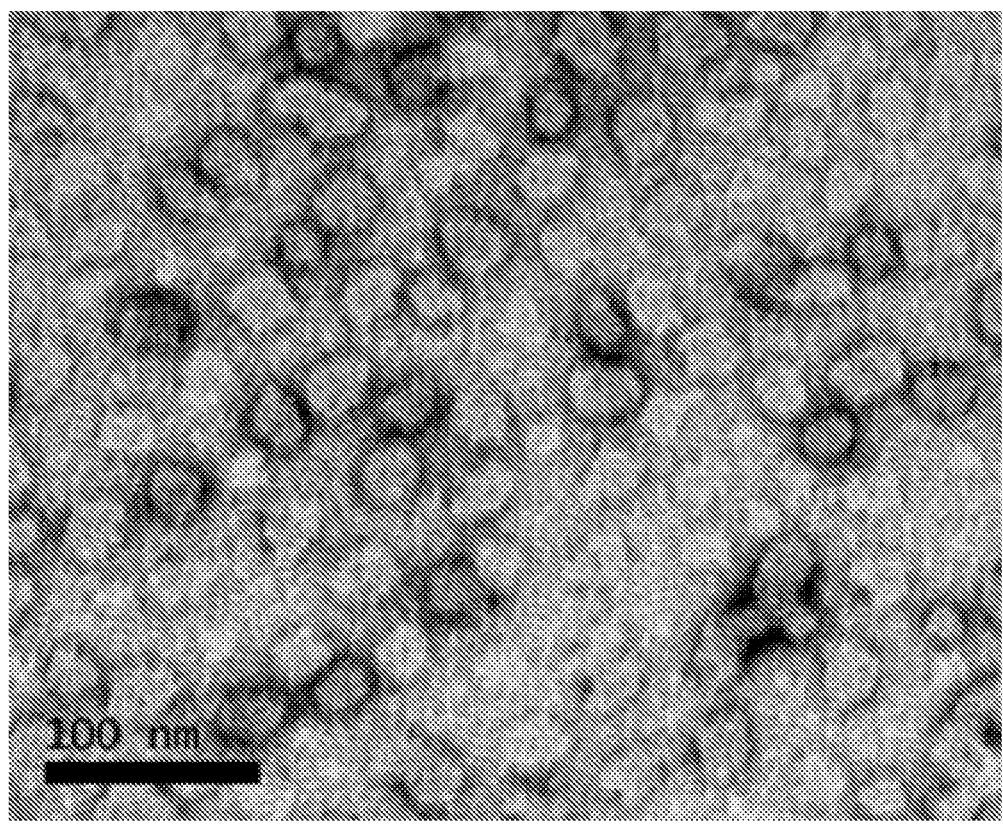
FIG. 9: An illustrative example of the transmission electron microscopy (TEM) analysis of polymer PRx0729v6.

Transmission Electron Microscopy (TEM) Analysis of Polymer PRx0729v6. (FIG. 9)

This example provides evidence, using electron spectroscopy, that the polymer PRx0729v6 forms spherical micelle-like particles.

A 0.5 mg/ml solution of polymer PRx0729v6 in PBS was applied to a carbon coated copper grid for 30 minutes. The grid was fixed in Karnovsky's solution and washed in cacodylate buffer once and then in water 8 times. The grid was stained with a 6% solution of uranyl acetate for 15 minutes and then dried until analysis. Transmission electron microscopy (TEM) was carried out on a JEOL microscope. FIG. 9 shows a typical electron micrograph of polymer PRx0729v6 demonstrating spherical particles with approximate dimensions similar to the expected size of the micelle cores relative to those determined in solution by dynamic light scattering.

Example 16

Fluorescence Microscopy of Cell Uptake and Intracellular Distribution of Polymer-siRNA Complexes. (FIG. 10)

This example demonstrates that polymer PRx0729v6 can mediate a more efficient cellular uptake of fluorescent-labeled siRNA and endosomal release than a lipid-based transfection reagent.

Figure 10A:
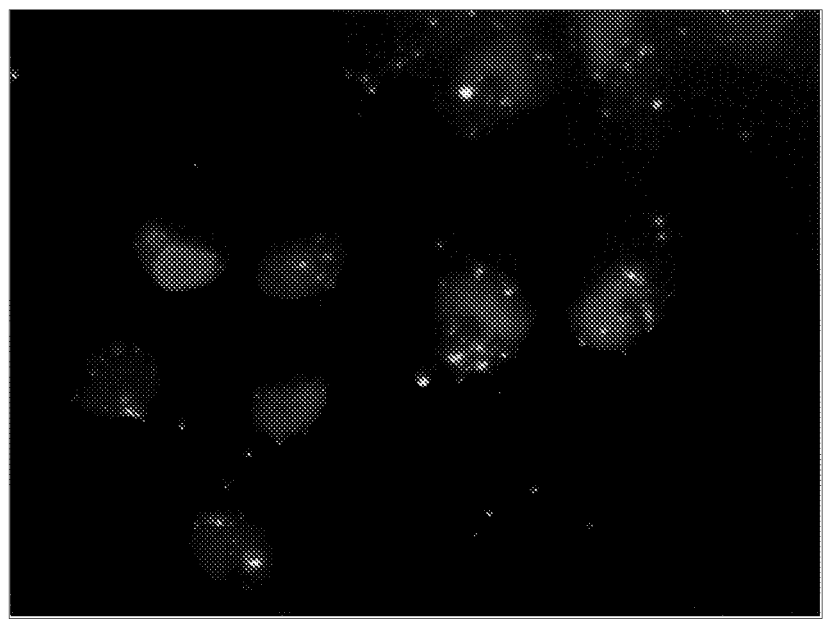
FIG. 10: An illustrative example of the fluorescence microscopy of cell uptake and intracellular distribution of polymer-siRNA complexes.
Figure 10B:
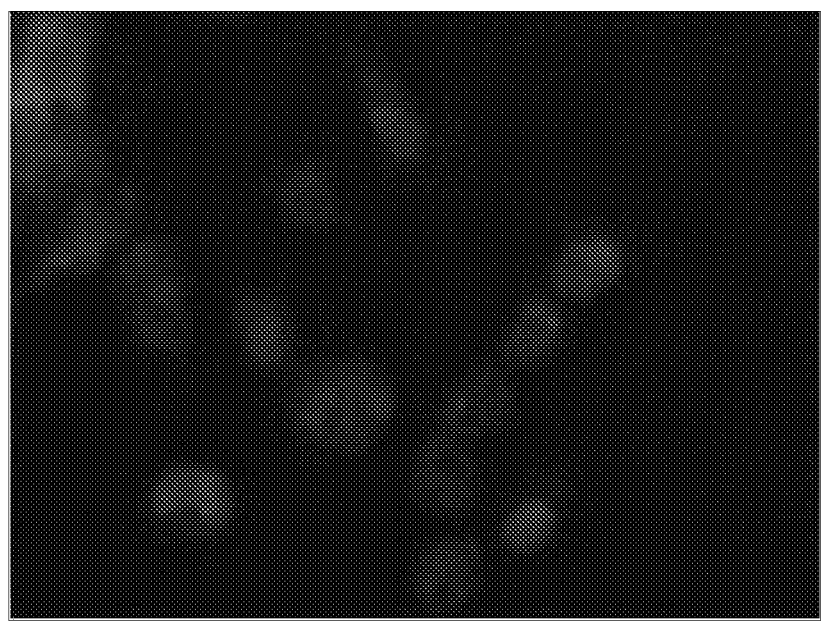

HeLa cells were plated on a Lab-Tek II chambered coverglass. Following overnight incubation, cells were transfected with either 100 nM FAM-siRNA/lipofectamine 2000 or with 100 nM FAM-siRNA at a Polymer-siRNA 4:1 charge ratio. Complexes were formed in PBS pH 7.4 for 30 minutes at a 5× concentration, added to cells for final 1× concentration, and incubated overnight. Cells were stained with DAPI (for visualization of the nucleus) for 10 minutes and then fixed in 3.7% formaldehyde-1×PBS for 5 minutes and washed with PBS. Samples were imaged with a Zeiss Axiovert fluorescent microscope. FIG. 10B shows the fluorescence microscopy of cell uptake and intracellular distribution of polymer-siRNA compared to lipofectamine (FIG. 10A). Particulate staining of lipofectamine-siRNA complexes suggest an endosomal location, while diffuse cytoplasmic staining of polymer-siRNA complexes indicate they have been released from endosomes into the cytoplasm.

Example 17

Uptake of Small Hydrophobic Molecules into Polymer PRx0729v6 Micelles

This example demonstrates that small hydrophobic molecules are taken up by the predominantly hydrophobic micelle core of polymer PRx0729v6.

The formation of polymer micelles with or without siRNA was confirmed by a fluorescence probe technique using pyrene ($C_{16}H_{10}$, MW=202), in which the partitioning of pyrene into the micellar core was determined using the ratio of 2 emission maxima of the pyrene spectrum. The fluorescence emission spectrum of pyrene in the polymer micelle solution was measured from 300 to 360 nm using a fixed excitation wavelength of 395 nm with a constant pyrene concentration of $6\times10^{-7}$ M. The polymer was varied from 0.001% to 20% (w/w) with or without 100 nM siRNA. The spectral data were acquired using a Varian fluorescence spectrophotometer. All fluorescence experiments are carried out at 25° C. The critical micelle concentration (CMC) was determined by plotting the intensity ratio $I_{336}/I_{333}$ as a function of polymer concentration. CMC values were calculated to be approximately 2 ug/ml.

Similarly, a model small molecule drug, dipyridamole (2-{[9-(bis(2-hydroxyethyl)amino)-2,7-bis(1-piperidyl)-3,5,8,10-tetrazabicyclo[4.4.0]deca-2,4,7,9,11-pentaen-4-yl]-(2-hydroxyethyl)amino}ethanol; $C_{24}H_{40}N_8O_4$, MW=505) is incorporated into the micelle core of PRx0729v6 as follows. Polymer (1.0 mg) and dipyridamole (DIP) (0.2 mg) are dissolved in THF (0.5 mL). Deionized water (10 mL) is added dropwise and the solution is stirred at 50° C. for 6 h to incorporate the drug into the hydrophobic core of the micelle. The solution (2.5 mL) is divided, and the absorbance of dipyridamole is measured at 415 nm by UV-vis spectroscopy at 25 and 37° C. Control measurements are also conducted by measuring the time-dependent reduction in dipyridamole absorbance in deionized water in the absence of copolymer. The absorbance at both 25 and 37° C. is measured for each time point, and the value is subtracted from that observed in the solution.

Example 18

Effect of pH on Polymer Structure. (FIG. 11)

This example demonstrates that the micelle structure of polymer PRx0729v6.2 is dissociated upon lowering the pH from 7.4 to 4.7.

Particle Size of polymer PRx0729v6.2 was measured by dynamic light scattering at pH 7.4 and a series of acidic pH values down to pH4.7 in PBS at 5-fold serial dilutions from 0.5 mg/ml-0.004 mg/ml. FIG. 11A shows that at pH 7.4, the polymer is stable to dilution down to 4 ug/ml where it begins to dissociate to a form that produces aggregates. FIG. 11B shows that at increasing acidic pH values down to pH 4.7 the polymer dissociation from a micelle structure is enhanced, that is, occurs at higher polymer concentrations, and produces increasing levels of polymer monomers from 1-8 nm in size.

Example 19

Methods for Conjugating Targeting Ligands and Polynucleotides to a Copolymer The following examples demonstrate methods for conjugating a targeting ligand (for example, galactose) or a polynucleotide therapeutic (for example siRNA) to a diblock copolymer. (1) The polymer is prepared using reversible addition fragmentation chain transfer (RAFT) (Chiefari et al. *Macromolecules*. 1998; 31(16):5559-5562) to form a galactose end-functionalized, diblock copolymer, using a chain transfer agent with galactose as the R-group substituent. (2) The first block of a diblock copolymer is prepared as a copolymer containing methylacrylic acid-N-hydroxy succinamide (MAA(NHS)) where a galactose-PEG-amine is conjugated to the NHS groups or where an amino-disulfide siRNA is conjugated to the NHS, or where pyridyl disulfide amine is reacted with the NHS groups to form a pyridyl disulfide that is subsequently reacted with thiolated RNA to form a polymer-RNA conjugate.

Example 19.1

Preparation of Galactose-PEG-Amine and Galactose-CTA

Scheme 1 illustrates the synthesis scheme for galactose-PEG-amine (compound 3) and the galactose-CTA (chain transfer agent) (compound 4).

Compound 1: Pentaacetate galactose (10 g, 25.6 mmol) and 2-[2-(2-Chloroethoxy)ethoxy]ethanol (5.6 mL, 38.4 mmol) were dissolved in dry $CH_2Cl_2$ (64 mL) and the reaction mixture was stirred at RT for 1 h. The $BF_3.OEt_2$ (9.5 ml, 76.8 mmol) was added to the previous mixture dropwise over 1 h in an ice bath. The reaction mixture was stirred at room temperature (RT) for 48 h. After the reaction, 30 mL of $CH_2Cl_2$ was added to dilute the reaction. The organic layer was neutralized with saturated $NaHCO_{3(aq)}$, washed by brine and then dried by $MgSO_4$. The $CH_2Cl_2$ was removed under reduced pressure to get the crude product. The crude product was purified by flash column chromatography to get final product 1 as slight yellow oil. Yield: 55% TLC ($I_2$ and p-Anisaldhyde): EA/Hex:1/1 (Rf: β=0.33; α=0.32; unreacted S.M 0.30).

Compound 2: Compound 1 (1.46 g, 2.9 mmol) was dissolved in dry DMF (35 mL) and the $NaN_3$ (1.5 g, 23.2 mmol) was added to the mixture at RT. The reaction mixture was heated to 85-90 C overnight. After the reaction, EA (15 mL) was added to the solution and water (50 mL) was used to wash the organic layer 5 times. The organic layer was dried by $MgSO_4$ and purified by flash column chromatography to get compound 2 as a colorless oil. Yield: 80%, TLC ($I_2$ and p-Anisaldhyde): EA/Hex:1/1 (Rf: 0.33).

Compound 3: Compound 2 (1.034 g, 2.05 mmol) was dissolved in MeOH (24 mL) and bubbled with $N_2$ for 10 min and then Pd/C (10%) (90 mg) and TFA (80 uL) were added to the previous solution. The reaction mixture was bubbled again with $H_2$ for 30 min and then the reaction was stirred at RT under $H_2$ for another 3 h. The Pd/C was removed by celite and MeOH was evaporated to get the compound 3 as a sticky gel. Compound 3 can be used without further purification. Yield: 95%. TLC (p-Anisaldhyde): MeOH/$CH_2Cl_2$: 1/4 (Rf: 0.05).

Compound 4: ECT (0.5 g, 1.9 mmol), NHS (0.33 g, 2.85 mmol) and DCC (0.45 g, 2.19 mmol) were dissolved in $CHCl_3$ (15 mL) at 0 C. The reaction mixture was continuously stirred at RT overnight. Compound 3 (1.13 g, 1.9 mmol) and TEA (0.28 mL, 2.00 mmol) in $CHCl_3$ (10 mL) were added slowly to the previous reaction at 0 C. The reaction mixture was continuously stirred at RT overnight. The $CH_3Cl$ was removed under reduced pressure and the crude product was purified by flash column chromatography to get the compound 4 as a yellow gel. Yield (35%). TLC: MeOH/CH$_2$Cl$_2$: 1/9 (Rf: 0.75)

Scheme 1. Synthesis of galactose-PEG-amine (cpd 3) and galactose-CTA (cpd 4)

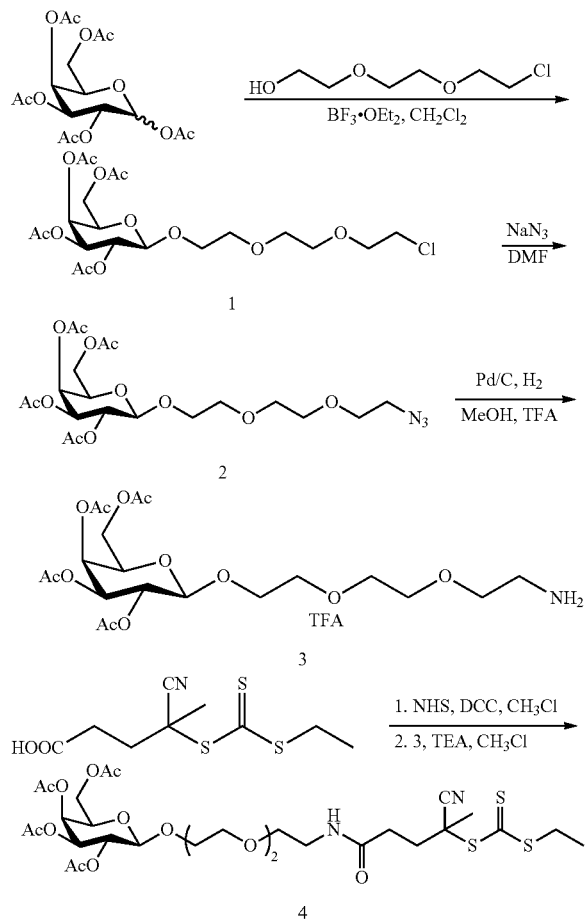

Example 19.2

Synthesis of [DMAEMA]-[BMA-PAA-DMAEMA]

A. Synthesis of DMAEMA macroCTA.

Polymerization: In a 20 mL glass vial (with a septa cap) was added 33.5 mg ECT (RAFT CTA), 2.1 mg AIBN (recrystallized twice from methanol), 3.0 g DMAEMA (Aldrich, 98%, was passed through a small alumina column just before use to remove the inhibitor) and 3.0 g DMF (high purity without inhibitor). The glass vial was closed with the Septa Cap and purged with dry nitrogen (carried out in an ice bath under stirring) for 30 min. The reaction vial was placed in a preheated reaction block at 70° C. The reaction mixture was stirred for 2 h 40 min. The septa cap was opened and the mixture was stirred in the vial in an ice bath for 2-3 minutes to stop the polymerization reaction.

Purification: 3 mL of acetone was added to the reaction mixture. In a 300 mL beaker was added 240 mL hexane and 60 mL ether (80/20 (v/v)) and under stirring the reaction mixture was added drop by drop to the beaker. Initially this produces an oil which is collected by spinning down the cloudy solution; yield=1.35 g (45%). Several precipitations were performed (e.g., 6 times) in hexane/ether (80/20 (v/v)) mixed solvents from acetone solution. Finally, the polymer was dried under vacuum for 8 h at RT; yield≈1 g.

Summary: ($M_{n,theory}$=11,000 g/mol at 45% conv.)

| Name | FW (g/mol) | Equiv. | mol | Weight | Actual weight |
|---|---|---|---|---|---|
| DMAEMA | 157.21 | 150 | 0.0191 | 3.0 g | 3.01 g |
| ECT | 263.4 | 1 | 1.2722 × 10$^{-4}$ | 33.5 mg | 33.8 mg |
| AIBN | 164.21 | 0.1 | 1.2722 × 10$^{-5}$ | 2.1 mg | 2.3 mg |

DMF=3.0 g; N$_2$ Purging: 30 min; Conduct polymerization at 70° C. for 2 h 45 min.

B. Synthesis of [BMA-PAA-DMAEMA] from DMAEMA macroCTA

All chemicals and reagents were purchased from Sigma-Aldrich Company unless specified. Butyl methacrylate (BMA) (99%), 2-(Dimethylamino) ethyl methacrylate (DMAEMA) (98%) were passed through a column of basic alumina (150 mesh) to remove the polymerization inhibitor. 2-propyl acrylic acid (PAA) (>99%) was purchased without inhibitor and used as received. Azobisisobutyronitrile (AIBN) (99%) was recrystallized from methanol and dried under vacuum. The DMAEMA macroCTA was synthesized and purified as described above (Mn~10000; PDI~1.3; >98%). N,N-Dimethylformamide (DMF) (99.99%) (Purchased from EMD) was reagent grade and used as received. Hexane, pentane and ether were purchased from EMD and they were used as received for polymer purification.

Polymerization: BMA (2.1 g, 14.7 mmoles), PAA (0.8389 g, 7.5 mmoles), DMAEMA (1.156 g, 7.35 mmoles), MacroCTA (0.8 g, 0.0816 mmoles), AIBN (1.34 mg, 0.00816 mmoles; CTA:AIBN 10:1) and DMF (5.34 ml) were added under nitrogen in a sealed vial. The CTA:Monomers ratio used was 1:360 (assuming 50% of conversion). The monomers concentration was 3 M. The mixture was then degassed by bubbling nitrogen into the mixture for 30 minutes and then placed in a heater block (Thermometer: 67° C.; display: 70-71; stiffing speed 300-400 rpm). The reaction was left for 6 hours, then stopped by placing the vial in ice and exposing the mixture to air.

Purification: Polymer purification was done from acetone/DMF 1:1 into hexane/ether 75/25 (three times). The resulting polymer was dried under vacuum for at least 18 hours. The NMR spectrum showed a high purity of the polymer. No vinyl groups were observed. The polymer was dialysed from ethanol against double de-ionized water for 4 days and then lyophilized. The polymer was analyzed by gel permeation chromatography (GPC) using the following conditions: Solvent: DMF/LiBr 1%. Flow rate: 0.75 ml/min. Injection volume: 100 µl.

Column temperature: 60° C. Poly (styrene) was used to calibrate the detectors. GPC analysis of the resulting Polymer: Mn=40889 g/mol. PDI=1.43. do/dc=0.049967.

Example 19.3

Synthesis of gal-[DMAEMA]-[BMA-PAA-DMAEMA]

Figure 13:
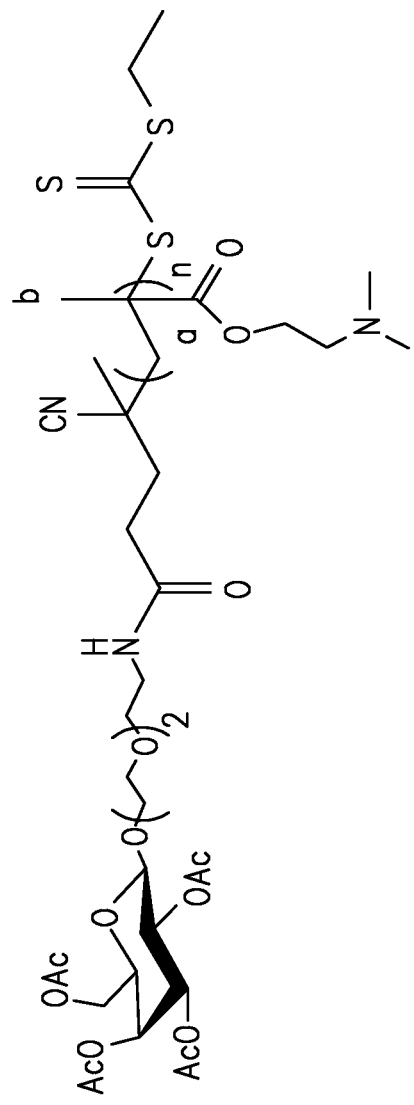
FIG. 13: An illustrative example of the galactose end functionalized poly[DMAEM]-macro CTA

Synthesis was carried out as described in example 19.2. First, a galactose-DMAEMA macro-CTA was prepared (example 19.2.A.) except that galactose-CTA (example 19.1, cpd 4) was used in place of ECT as the chain transfer agent. This resulted in the synthesis of a polyDMAEMA with an end functionalized galactose (FIG. 13). The galactose-[DMAEMA]-macro-CTA was then used to synthesize the second block [BMA-PAA-DMAEMA] as described in example 19.2.B. Following synthesis, the acetyl protecting groups on the galactose were removed by incubation in 100 mM sodium bicarbonate buffer, pH 8.5 for 2 hrs, followed by dialysis and lyophilization. NMR spectroscopy was used to confirm the presence of the deprotected galactose on the polymer.

Example 19.4

Figure 14:
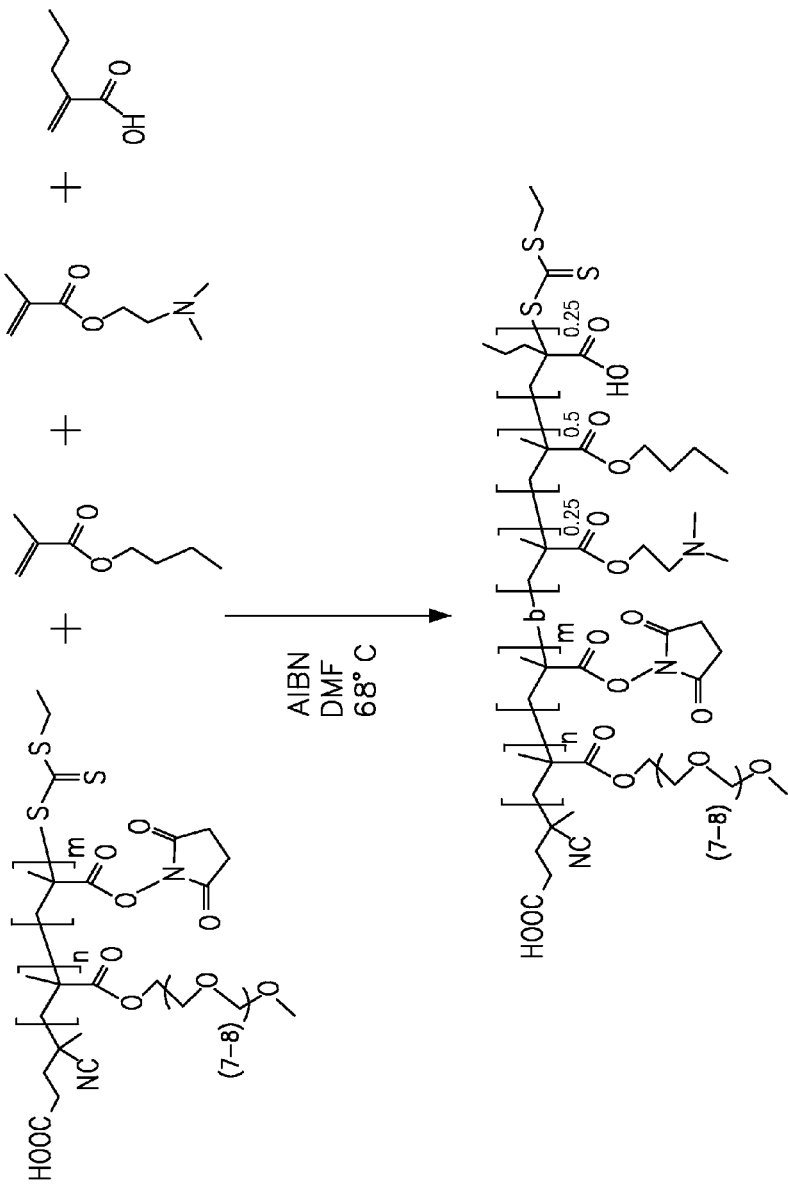
FIG. 14: An illustrative example of the synthesis of [PEGMA-MAA(NHS)]-[B-P-D]

Preparation and Characterization of [PEGMA-MAA (NHS)]-[B-P-D] and DMAEMA-MMA(NHS)-[B-P-D] Diblock Co-polymers FIG. 14 summarizes the synthesis of [PEGMA-MAA (NHS)]-[B-P-D] polymer where the co-polymer ratio of monomers in the $1^{st}$ block is 70:30 and FIG. 15 summarizes the characterization of [PEGMA-MAA(NHS)]-[B-P-D] polymer where the co-polymer ratio of monomers in the $1^{st}$ block is 70:30.

Example 19.5

Figure 16:
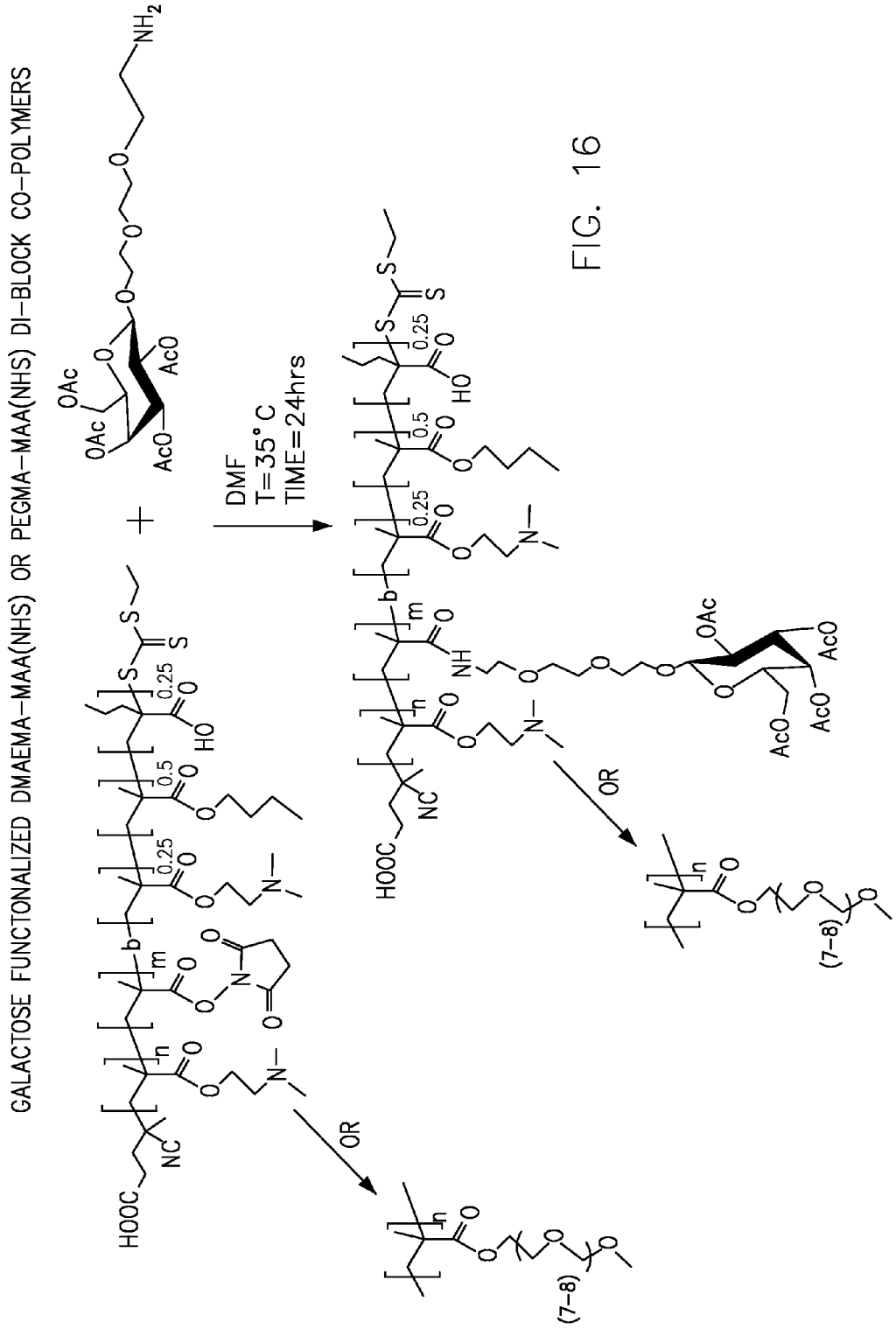
FIG. 16: An illustrative example of the galactose functionalized DMAEMA-MAA(NHS) or PEGMA-MAA(NHS) diblock co-polymers

Conjugation of Galactose-Peg-Amine to PEGMA-MAA(NHS) to Produce [PEGMA-MAA(Gal)]-[B-P-D] Polymer FIG. 16 illustrates the preparation of galactose functionalized DMAEMA-MAA(NHS) or PEGMA-MAA(NHS) diblock co-polymers. Polymer [DMAEMA-MAA(NHS)]-[B-P-D] or [PEGMA-MAA(NHS)]-[B-P-D] was dissolved in DMF at a concentration between 1 and 20 mg/ml. Galactose-PEG-amine prepared as described in example 19.1 (cpd 3) was neutralized with 1-2 equivalents of triethylamine and added to the reaction mixture at a ratio of 5 to 1 amine to polymer. The reaction was carried at 35° C. for 6-12 hrs, followed by addition of an equal volume of acetone, dialysis against deionized water for 1 day and lyophilization.

Example 19.6

Figure 17A:
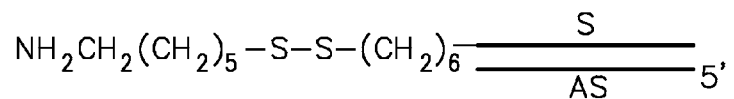
FIG. 17: An illustrative example of the structures of conjugatable siRNAs, peptides and pyridyl disulfide amine
Figure 17B:
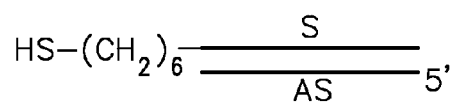
Figure 17C:
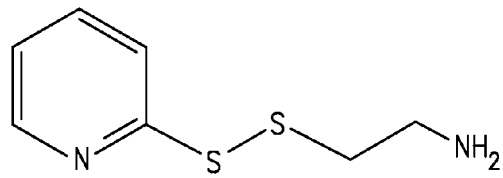
Figure 17D:
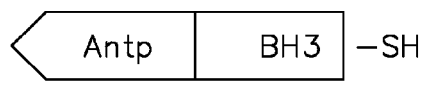

Conjugation of siRNA to [PEGMA-MAA(NHS)]-[B-P-D] to Produce [PEGMA-MAA(RNA)]-[B-P-D] Polymer FIG. 17A and FIG. 17B show the structures of 2 modified siRNAs that can be conjugated to NHS containing polymers. siRNAs were obtained from Agilent (Boulder, Colo.). FIG. 17C shows the structure of pyridyl disulfide amine used to derivatize NHS containing polymers to provide a disulfide reactive group for the conjugation of thiolated RNA (FIG. 17B).

Reaction of NHS containing polymer with amino-disulfide-siRNA. The reaction is carried out under standard conditions consisting of an organic solvent (for example, DMF or DMSO, or a mixed solvent DMSO/buffer pH 7.8.) at 35° C. for 4-8 hrs, followed by addition of an equal volume of acetone, dialysis against deionized water for 1 day and lyophilization.

Reaction of NHS containing polymer with pyridyl-disulfide-amine and reaction with thiolated siRNA. Reaction of pyridyl disulfide amine with NHS containing polymers is carried out. Subsequently the lyophilized polymer is dissolved in ethanol at 50 mg/ml and diluted 10-fold in sodium bicarbonate buffer at pH 8. Thiolated siRNA (FIG. 16B) is reacted at a 2-5 molar excess over polymer NHS groups at 35° C. for 4-8 hrs, followed by dialysis against phosphate buffer, pH 7.4.

Example 21.7

Conjugation of a Therapeutic Peptide to a Pyridyl-disulfide Modified Polymer

The pyridyl-disulfide modified polymer described in Example 21.6, [PEGMA-MAA(NHS)]-[B-P-D], can also be used for conjugation to a therapeutic peptide (FIG. 17 D). The peptide is synthesized, prepared for conjugation, and the conjugation reaction carried out as described below. to produce [PEGMA-MAA(Peptide)]-[B-P-D] polymer.

Fusion with the peptide transduction domain peptide transportin (also know as the Antennapedia peptide (Antp) sequence is utilized to synthesize a cell internalizing form of the Bak-BH3 peptide (Antp-BH3) containing a carboxy-terminal cysteine residue (NH2-RQIKIWFQNRRMKWKK-MGQVGRQLAIIGDDINRRYDSC-COOH). To ensure free thiols for conjugation, the peptide is reconstituted in water and treated for 1 hour with the disulfide reducing agent TCEP immobilized within an agarose gel. The reduced peptide (400 µM) is then reacted for 24 hours with the pyridyl disulfide end-functionalized polymer in phosphate buffer (pH 7) containing 5 mM ethylenediaminetetraacetic acid (EDTA).

Reaction of the pyridyl disulfide polymer end group with the peptide cysteine creates 2-pyridinethione, which can be spectrophotometrically measured to characterize conjugation efficiency. To further validate disulfide exchange, the conjugates are run on an SDS-PAGE 16.5% tricine gel. In parallel, aliquots of the conjugation reactions are treated with immobilized TCEP prior to SDS-PAGE to verify release of the peptide from the polymer in a reducing environment.

Conjugation reactions are conducted at polymer/peptide stoichiometries of 1, 2, and 5. UV spectrophotometric absorbance measurements at 343 nm for 2-pyridinethione release indicates conjugation efficiency. An SDS PAGE gel is utilized to further characterize peptide-polymer conjugates. At a polymer/peptide molar ratio of 1, a detectable quantity of the peptide forms dimers via disulfide bridging through the terminal cysteine. However, the thiol reaction to the pyridyl disulfide is favored, and the free peptide band is no longer visible at polymer/peptide ratios equal to or greater than 2. By treating the conjugates with the reducing agent TCEP, it is possible to cleave the polymer-peptide disulfide linkages as indicated by the appearance of the peptide band in these samples.

What is claimed is:

1. A polymeric carrier comprising:
   (a) a plurality of polymers that are block copolymers assembled into a polymeric carrier, the polymeric carrier comprising a core and a shell, the block copolymers having the chemical Formula I:

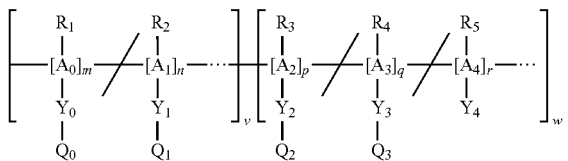

(I)

wherein
   each of $A_0, A_1, A_2, A_3$ and $A_4$ is —C—C—;
   $Y_0$ is —C(O)O(1C-10C)alkyl-, optionally substituted with one or more fluorine groups;
   $Y_1$ is —C(O)O(2C-10C)alkyl-;
   $Y_2$ is —C(O)OCH$_2$CH$_2$—;
   $Y_3$ is a covalent bond;
   $Y_4$ is —C(O)O(CH$_2$)$_3$CH$_3$;
   wherein tetravalent carbon atoms of $A_0$-$A_4$ that are not fully substituted with $R_1$-$R_5$ and $Y_0$-$Y_4$ are completed with an appropriate number of hydrogen atoms;
   $R_1$ is (1C-3C)alkyl;
   each of $R_2$, $R_3$, and $R_5$ is —CH$_3$;
   $R_4$ is —CH$_2$CH$_2$CH$_3$;
   $Q_0$ is a pyridyl disulfide residue;
   $Q_1$ is a residue selected from the group consisting of polyoxylated alkyl, polyethylene glycol, and polypropylene glycol;
   $Q_2$ is a dimethylamino residue;
   $Q_3$ is a carboxyl residue;
   m is greater than 0 to less than 1.0;
   n is greater than 0 to less than 1.0, wherein m+n=1;
   p is 0.1 to 0.9;
   q is 0.1 to 0.9;
   r is 0 to 0.8 wherein p+q+r=1;
   v is 1 to 25 kDa; and
   w is 1 to 50 kDa; and
   (b) at least one polynucleotide,
wherein the polynucleotide is not in the core of the polymeric carrier.

2. The polymeric carrier of claim 1, wherein the at least one polynucleotide is an oligonucleotide.

3. The polymeric carrier of claim 1, further comprising a targeting moiety.

4. The polymeric carrier of claim 1, wherein the targeting moiety is attached to the shell portion by a covalent bond to a polymer.

5. The polymeric carrier of claim 1, wherein the plurality of polymers have spontaneously self-assembled into the polymeric carrier.

6. The polymeric carrier of claim 1, wherein the shell of the polymeric carrier comprises the polynucleotide.

7. The polymeric carrier of claim 1, wherein the at least one polynucleotide is attached to the block copolymer by a covalent bond, a non-covalent interaction, or a combination thereof.

8. The polymeric carrier of claim 1, wherein the polynucleotide is an siRNA.

9. A composition comprising the polymeric carrier of claim 1.

10. The polymeric carrier of claim 1, wherein $Q_1$ is a polyethylene glycol residue.

11. The polymeric carrier of claim 1, wherein
    $Y_1$ is —C(O)OCH$_2$CH$_2$—.

12. The polymeric carrier of claim 1, wherein
    $Y_0$ is —C(O)OCH$_2$CH$_2$—.

13. The polymeric carrier of claim 1, wherein v is 5 to 25 kDa.

* * * * *